(12) United States Patent
White

(10) Patent No.: US 11,458,282 B2
(45) Date of Patent: Oct. 4, 2022

(54) CATHETER ASSEMBLY WITH DISTINCT INFLATION AND DRUG DELIVERY CHANNELS AND OVERLAPPING BALLOON LAYERS

(71) Applicant: PATIENT SHIELD CONCEPTS, LLC, Denver, CO (US)

(72) Inventor: Lynn Rosen White, Denver, CO (US)

(73) Assignee: Patient Shield Concepts, LLC, Denver, CO (US)

( * ) Notice: Subject to any disclaimer, the term of this patent is extended or adjusted under 35 U.S.C. 154(b) by 976 days.

(21) Appl. No.: 16/075,506

(22) PCT Filed: Jul. 25, 2016

(86) PCT No.: PCT/US2016/043920
§ 371 (c)(1),
(2) Date: Aug. 3, 2018

(87) PCT Pub. No.: WO2017/135993
PCT Pub. Date: Aug. 10, 2017

(65) Prior Publication Data
US 2019/0030282 A1 Jan. 31, 2019

Related U.S. Application Data

(60) Provisional application No. 62/291,372, filed on Feb. 4, 2016.

(51) Int. Cl.
*A61M 29/00* (2006.01)
*A61M 25/00* (2006.01)
*A61M 25/10* (2013.01)

(52) U.S. Cl.
CPC .... *A61M 25/0017* (2013.01); *A61M 25/1011* (2013.01); *A61M 25/1027* (2013.01);
(Continued)

(58) Field of Classification Search
CPC .... A61M 2025/1013; A61M 2025/105; A61M 2025/1086; A61M 25/0017;
(Continued)

(56) References Cited

U.S. PATENT DOCUMENTS 3,625,793 A * 12/1971 Sheridan ................. B29C 57/00
156/229
5,286,254 A * 2/1994 Shapland ............ A61M 25/104
604/103.01

(Continued)

*Primary Examiner* — Rebecca E Eisenberg
(74) *Attorney, Agent, or Firm* — Holzer Patel Drennan

(57) ABSTRACT

A catheter 100 is comprised of a shaft 120 having a distal end and a proximal end, the distal end being the end an end of the catheter 100 to be placed within the bladder 105, the proximal end being the end of the catheter 100 to be coupled to the inputs outside of the body, the shaft 120 having at least three discrete lumens, the at least three lumens including an inflation lumen 124, the inflation lumen 124 in fluid communication with an inflation side hole 130 in the shaft 120. The shaft has a drug delivery lumen 122, the drug delivery lumen 122 in fluid communication with a drug fluid side hole 128 in the shaft 120. The shaft has a bladder fluid lumen 126, the bladder fluid lumen 126 in fluid communication with a bladder drainage aperture 132 in the shaft 120, wherein distally refers to a distal reference direction 101 towards the elements to be placed in the bladder, and proximally refers to a proximal reference direction 103 towards inputs that remain outside of the body, wherein drug delivery lumen 122, the inflation lumen 124, and the bladder fluid lumen 126 are not in fluid communication.

20 Claims, 26 Drawing Sheets

(52) U.S. Cl.
CPC ............... *A61M 2025/105* (2013.01); *A61M 2025/1013* (2013.01); *A61M 2025/1086* (2013.01)

(58) Field of Classification Search
CPC .......... A61M 25/1011; A61M 25/1002; A61M 25/0029; A61M 25/10; A61M 25/0009; A61M 25/1027
See application file for complete search history.

(56) References Cited

U.S. PATENT DOCUMENTS

| | | | | |
|---|---|---|---|---|
| 5,417,657 A | * | 5/1995 | Hauer ............... | A61M 25/0017 604/103.02 |
| 2015/0209558 A1 | * | 7/2015 | Charlebois ........ | A61M 25/0155 604/101.02 |

* cited by examiner

CATHETER ASSEMBLY WITH DISTINCT INFLATION AND DRUG DELIVERY CHANNELS AND OVERLAPPING BALLOON LAYERS

CROSS-REFERENCE TO RELATED APPLICATION

This International Application claims the benefit of U.S. Provisional Application No. 62/291,372, filed Feb. 4, 2016.

FIELD

This specification generally relates to catheter devices and methods for making and using the catheter devices. The specification more particularly relates to drug-delivery capable urinary catheters.

BACKGROUND

The subject matter discussed in the background section should not be assumed to be prior art merely as a result of the subject matter's mention in the background section. Similarly, a problem and the understanding of the causes of a problem mentioned in the background section or associated with the subject matter of the background section should not be assumed to have been previously recognized in the prior art. The subject matter in the background section may merely represent different approaches, which in and of themselves may also be inventions.

A common issue with urinary catheters is that bladder spasms cause great discomfort when inserted and for the duration of the effective use of a urinary catheters. Catheters irritate the interior of the bladder, including the smooth muscle of the trigone, causing uncomfortable bladder spasms. Bladder spasms can cause kinking of the catheter bodies and eventually inconvenient leaks. Few drug delivery catheters exist, and fewer if any exist for urinary catheters to alleviate the spasms and inconvenient leaks.

Unlike perfusion catheters, for which drug delivery is more common, urinary catheters are larger and require greater inflation. Inflating the interior balloons with drug-containing fluids is practical for perfusion catheters, but inflating a urinary catheter balloon with drug containing substances is wasteful and inefficient, as much of the drug substances will simply remain in the balloon. Also, should that balloon inflated with drug-containing fluid burst or leak, the balloon may cause serious drug toxicity. The same issue of drug toxicity applies to an open irrigating catheter used for rectal irrigation.

Existing drug delivery perfusion catheters deliver drugs in all directions, which is appropriate for uniform surfaces, but the surface where the bladder interacts with the balloon of a catheter is not uniformly shaped. Erratic injection of drugs into the bladder can lead to aggregation of drug fluid and possible toxicity. Without a controlled release of drug at the specific sites and without separate passageways for inflation and drug delivery, the patients will have to deal with bills for wasted drugs and the possibility of toxicity or sufficiently strong dosage to render the bladder temporary ineffective for longer than is necessary.

BRIEF DESCRIPTION OF THE FIGURES

In the following drawings, like-reference numbers refer to like elements. Although the following figures depict various examples of the invention, the invention is not limited to the examples depicted in the figures.

DETAILED DESCRIPTION

Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just address one deficiency that may be discussed in the specification, and some embodiments may not address any of these deficiencies.

In general, at the beginning of the discussion of each of FIGS. 1-26 is a brief description of each element, which may have no more than the name of each of the elements in the one of FIGS. 1-26 that is being discussed. After the brief description of each element, each element is further discussed in numerical order. In general, each of FIGS. 1-26 is discussed in numerical order and the elements within FIGS. 1-26 are also usually discussed in numerical order to facilitate easily locating the discussion of a particular element. Nonetheless, there is no one location where all of the information of any element of FIGS. 1-26 is necessarily located. Unique information about any particular element or any other aspect of any of FIGS. 1-16 may be found in, or implied by, any part of the specification. FIGS. 1-16 are not drawn to scale unless specified otherwise.

A urinary catheter that may have a drug delivery channel, an inflation channel and a urinary transfer channel is disclosed. The inflation channel may lead to a specific inflation balloon. The drug delivery channel may lead to a separate and membranous inflation balloon with pores situated at least partially on the inflation balloon. The catheter may be a Foley catheter of any size.

Figure 1:
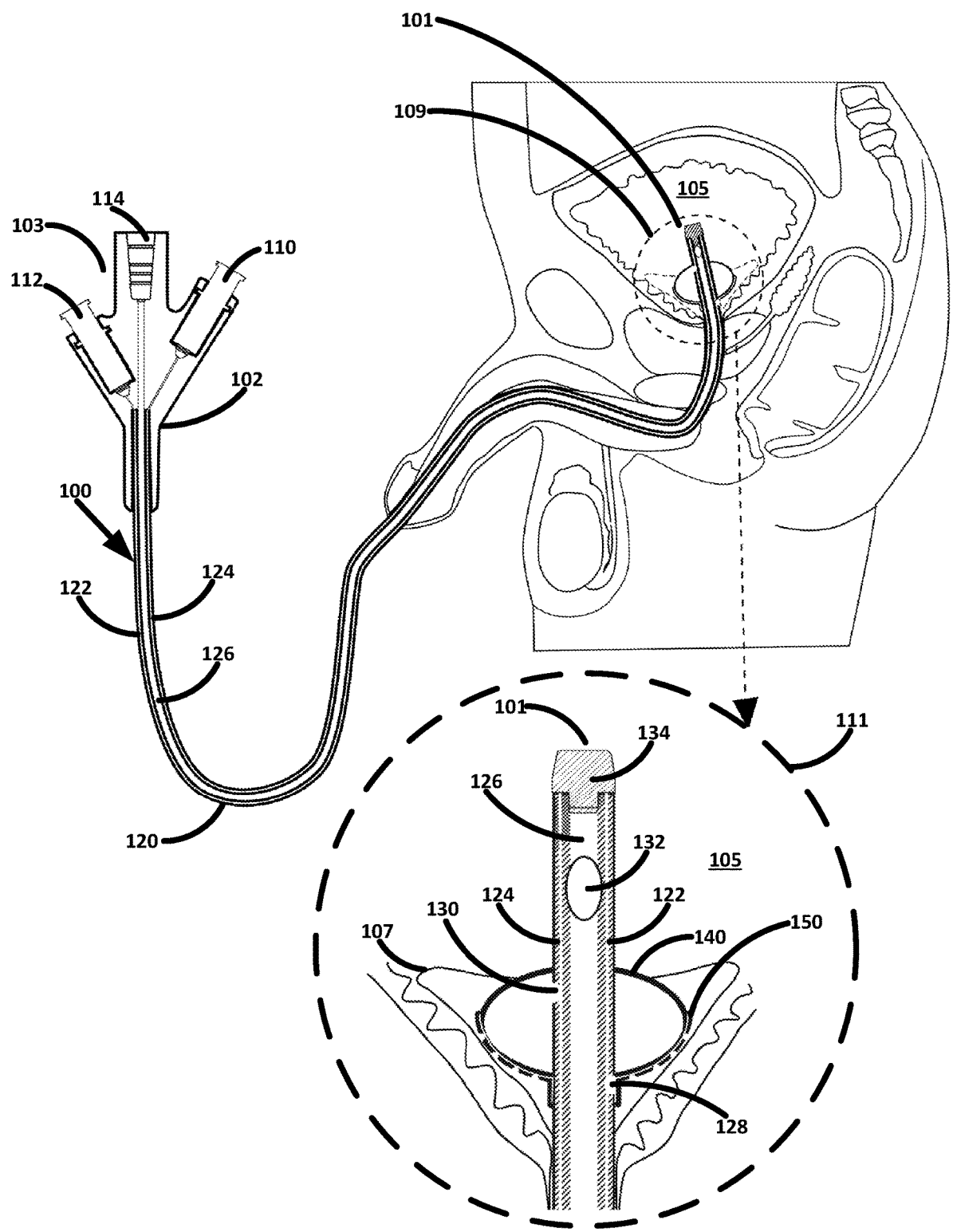
FIG. 1 shows a block diagram of a bisected side view of an embodiment of a catheter system for drug delivery to a patient's bladder.

FIG. 1 shows a block diagram of a bisected side view of an embodiment of a catheter system for drug delivery to a patient's bladder. The catheter system 100 may include an input manifold 102, a shaft 120, an inflation balloon 140, a drug delivery balloon 150, a distal side 101, a proximal side 103, a bladder 105, a trigone area 107, a focus circle 109, and a zoom view of the focus circle 111. In other embodiments, the catheter system 100 may not have all of the elements or features listed and/or may have other elements or features instead of or in addition to those listed.

The distal side 101 is a reference direction, which points towards the end of the catheter system 100 within the bladder. The distal side 101 is the side of the human body receiving the catheter and away from the location in the catheter system 100 where drug and inflation fluids are introduced in the input manifold. The proximal side 103 is a reference direction, which points towards the end of the catheter system 100 with the input manifold. The proximal side 103 is the side away from the human body receiving the catheter system 100 and towards the input manifold in the catheter system 100 where drug and inflation fluids are introduced. The proximal side 103 is opposite the distal side. The focus circle 109 is a hypothetical circle marking an area over which a zoom view may be used. The zoom view of the focus circle 111 is a zoomed view of the elements present in the focus circle 109.

The input manifold 102 is a component that receives input fluids such as inflation and drug fluid from a source and depletes drainage from the bladder and deflating inflation fluids, received by the input manifold 102 from the shaft 120. The input manifold 102 is a component that is situated at a proximal end of a catheter assembly. The fluid input manifold and its components, including the drug fluid input 112, the inflation fluid input 110, and/or the bladder drainage output 114, may be composed of any materials including, for instance, all, some, or one of poly-vinyl chloride, polytetrafluoroethylene (also known as "PTFE" or "Teflon"), latex rubber, silicone, silicone-elastomer coated latex, hydrophilic polymer coated latex, silver alloy coated polymer, hydrogel, polyether block amide, nitinol, nylon, polyethylene terephthalate, thermoplastic elastomers, ethylene vinyl acetate, polyetheretherketone, polyethene, polypropylene, and polyurethane. The input manifold 102 may have a drug fluid input 112, an inflation fluid input 110, and a bladder drainage output 114.

The drug fluid input 112 is an input, which receives drug-containing fluids (hereinafter "drug fluids") from a source. The drug fluid input 112 may be in fluid communication with a drug delivery lumen in the catheter shaft.

The drug fluid input 112 may be configured to receive any standard medical fluid input devices, such as syringes, lines from a drug delivery pump, and anything else that can inject fluids or withdraw. Drugs may be delivered in bolts via a syringe. The drugs may be delivered via an On-Q pain pump to deliver a continuous infusion. The drug fluid input 112 may be in fluid communication with a drug delivery lumen in a catheter shaft.

The drug fluid input 112 may be fashioned with a Luer taper to accept standard Luer-Lok and Luer-Slip devices in the slipping and locking configurations. The drug fluid input 112 may use either the male or female configurations of the Luer taper in order to facilitate a seal with other complimentary male or female Luer taper injectors. The drug fluid input 112 may be of any standard size for receiving common injectors, including, for example, an interior diameter at the most distal point of interaction of 0.1", 0.9", 0.14", 1", 0.19", 1.10", 0.24", 0.25", 0.26", 11/32", 13/32", 16/32", 17/32", 5/8", 9/16", 13/16", 3/4", 29/32", 39/32", 9/8", 1.55 mm, 1.81 mm, 0.41 mm, 0.71 mm, 0.61 mm, 0.91 mm, 0.33 mm, 0.63 mm, 0.2 mm, and 0.41 mm. For the purposes of this specification, when referencing a measurement, the quotation mark is used to denote inches, and the abbreviation, "mm" is used to denote millimeters.

Drug fluids to be used in the drug fluid input include, for instance lidocaine, bupivacaine, diazepam, oxybutlynin, flavoxate, dicyclomine, hyoscyamine sulfate, and tolterodine. Lidocaine may be used at a variety of concentrations, including, for instance, 8 mg/cc (where "cc" denotes milliliters or cubic centimeters and "mg" denotes milligrams), 9 mg/cc, 10 mg/cc, 11 mg/cc, 12 mg/cc, 13 mg/cc, 14 mg/cc, 15 mg/cc, 16 mg/cc, 17 mg/cc, 18 mg/cc, 19 mg/cc, 20 mg/cc, 21 mg/cc, 22 mg/cc, 23 mg/cc, 24 mg/cc, 25 mg/cc, 26 mg/cc, 27 mg/cc, 28 mg/cc, 29 mg/cc, 30 mg/cc, 31 mg/cc, and the like. Lidocaine may also be used in ranges of concentration from 9 mg/cc-15 mg/cc, 10 mg/cc-20 mg/cc, 9 mg/cc-21 mg/cc, 9 mg/cc-31 mg/cc and the like. Diazepam may be used in standard concentrations of, for instance, 1 mg/cc, 1.25 mg/cc, 2.5 mg/cc, 5 mg/cc, or 6 mg/cc. Diazepam may also be used in concentration ranges from 1.25 mg/cc-2.5 mg/cc, 1.25 mg/cc-5 mg/cc, 1 mg/cc-5 mg/cc, 1 mg/cc-6 mg/cc, and the like. Drug fluids may also incorporate anti-spasmodic drugs, for instance, valium.

The inflation fluid input 110 is an input and output, through which inflation fluid is added or removed for the purposes of inflating or deflating an inflation balloon. The inflation fluid input 110 may be in fluid communication with an inflation lumen in a shaft of a catheter.

The inflation fluid input 110 may be configured to receive any standard medical fluid input or output devices, such as syringes, lines from an inflation pump, and anything else that can inject or remove fluids. The inflation fluid input 110 may be in fluid communication with an inflation lumen of a catheter.

The inflation fluid input 110 may be fashioned with a Luer taper to accept standard Luer-Lok and Luer-Slip devices in the slipping and locking configurations. The inflation fluid input 110 may use either the male or female configurations of the Luer taper in order to facilitate a seal with other complimentary male or female Luer taper injectors. Both inflation and deflation may be achieved by passing an inflation fluid to or from the inflation fluid input. Examples of inflation fluid include air, water or saline. The inflation fluid input 110 may be of any standard size for receiving, including, for example, an interior diameter at the most distal point of interaction of 0.1", 0.9", 0.14", 1", 0.19", 1.10", 0.24", 0.25", 0.26", 11/32", 13/32", 16/32, 17/32", 5/8", 9/16", 13/16", 3/4", 29/32", 39/32", 9/8", 1.55 mm, 1.81 mm, 0.41 mm, 0.71 mm, 0.61 mm, 0.91 mm, 0.33 mm, 0.63 mm, 0.2 mm, and 0.41 mm.

The bladder drainage output 114 is the output through which urinary bladder fluids and drainage are expelled from the catheter system. The bladder drainage output 114 may be in fluid communication with a bladder fluid lumen in a shaft of a catheter to transfer bladder fluids and drainage from the bladder to an external reservoir. The output from the bladder drainage output 114 may be released into a separably couplable line, which then may be coupled to a bladder fluid and drainage reservoir.

The shaft 120 is an elongate, hollow body with a number of lumens and orifices for transfer of various fluids. The shaft 120 may have a drug delivery lumen 122, an inflation lumen 124, a bladder fluid lumen 126, a drug fluid side hole 128, an inflation side hole 130, a drainage 132, and an end cap 134.

The shaft 120 and its components, including the drug delivery lumen 122, an inflation lumen 124, a bladder fluid lumen 126, a drug fluid side hole 128, an inflation side hole 130, a drainage aperture 132, and/or an end cap 134 may be fashioned from any materials including, for instance, all, some, or one of poly-vinyl chloride, polytetrafluoroethylene (also known as "PTFE" or "Teflon"), latex rubber, silicone, silicone-elastomer coated latex, hydrophilic polymer coated latex, silver alloy coated polymer, hydrogel, nitinol, nylon, polyethylene terephthalate, thermoplastic elastomers, polyether block amide, ethylene vinyl acetate, polyetheretherketone, polyethene, polypropylene, and polyurethane. In an embodiment, the lumens may contain no sensors. In an embodiment, the lumens may contain no electronic wires. In still another embodiment, the drug delivery lumen 122, does not have an electronic wire. In still another embodiment, the inflation lumen 124 does not have an electronic wire. In still another embodiment, the bladder fluid lumen has no electronic wire. An electronic wire is distinct from a guiding wire used to place the catheter in the bladder, which is a standard component of a catheter and may be placed in any lumen. An electronic wire is a wire configured to carry an electronic signal, which may carry digital information. The shaft 120 may be coupled to the input manifold 102 at the proximal end of the shaft 120 and the distal end of the input manifold 102.

The shaft 120 may be of any external diameter, including, for instance, 1 Fr, 2 Fr, 3 Fr, 4 Fr, 5 Fr, 6 Fr, 7 Fr, 8 Fr, 9 Fr, 10 Fr, 11 Fr, 12 Fr, 13 Fr, 14 Fr, 15 Fr, 16 Fr, 17 Fr, 18 Fr, 19 Fr, 20 Fr, 21 Fr, 22 Fr, 23 Fr, 24 Fr, 25 Fr, 26 Fr, 27 Fr, 28 Fr, 29 Fr, 30 Fr, 31 Fr, 32 Fr, 33 Fr, 24 Fr, where "Fr" denotes the French measurement, in which a single Fr is equivalent to a third of a millimeter. The drug delivery lumen 122 may also be within certain external diameter ranges, for instance, 1 Fr-3 Fr, 3 Fr-6 Fr, 4 Fr-6 Fr, 10 Fr-48 Fr, 10 Fr-20 Fr, 10 Fr-15 Fr, 10 Fr-14 Fr, 12 Fr-14 Fr, and the like.

The drug delivery lumen 122 is a channel within the shaft 120 for communicating drug containing fluids from a drug fluid input 112 to a drug delivery balloon 150. The drug delivery lumen 122 may be in fluid communication with the drug fluid input 112. The drug delivery lumen 122 may also be in fluid communication with the space between the interior of the drug delivery balloon 150 and the exterior of the inflation balloon 140 via the drug fluid side hole 130. The drug delivery lumen 122 may have an internal diameter of, for example, 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, and the like. The diameter of a drug delivery lumen 122 may be in a range of, for instance, 0.005"-0.02", 0.011"-0.0147", 0.01"-0.05", 0.01"-0.06", 0.02"-0.04", 0.02"-0.05", 0.03"-0.044", 0.04"-0.053", 0.02"-0.06", 0.02"-0.053", 0.2 mm-0.4 mm, 0.1 mm-0.5 mm, 0.27 mm-0.44 mm, 0.5 mm-0.8 mm, 0.5 mm-1.5 mm, 0.5 mm-1 mm, 0.7 mm-1 mm, 0.7 mm-1.5 mm, or 0.7 mm-1.6 mm.

The inflation lumen 124 is a channel within the shaft 120 for communicating inflation fluids from an inflation fluid input 110 to the inflation balloon 140. The inflation lumen 124 may be in fluid communication with the inflation fluid input. The inflation may be also be in fluid communication with the space between the interior surface of the inflation balloon 140 and the exterior surface of the shaft via the inflation side hole 130. The inflation lumen 124 may have an internal diameter of, for example, 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, and the like. The diameter of an inflation lumen 124 may be in a range of, for instance, 0.005"-0.02", 0.011"-0.0147", 0.01"-0.05", 0.01"-0.06", 0.02"-0.04", 0.02"-0.05", 0.03"-0.044", 0.04"-0.053", 0.02"-0.06", 0.02"-0.053", 0.2 mm-0.4 mm, 0.1 mm-0.5 mm, 0.27 mm-0.44 mm, 0.5 mm-0.8 mm, 0.5 mm-1.5 mm, 0.5 mm-1 mm, 0.7 mm-1 mm, 0.7 mm-1.5 mm, or 0.7 mm-1.6 mm.

The bladder fluid lumen 126 is a lumen within the shaft 120 that allows fluid communication of bladder fluids between the bladder An and an external bladder fluid reservoir. These bladder fluids may include urine in the bladder as well as other forms of drainage, irrigation fluids, and excess drug fluids, for instance. The bladder fluid lumen 126 may be in fluid communication with the bladder fluid output 114 and the drainage aperture 132. The bladder fluid lumen 126 may not have a circular cross section, so the internal diameter may be dynamic and may have a widest diameter width and a narrowest diameter width. The bladder fluid lumen 126 may have a narrowest diameter width of any diameter width, for instance, 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.11", 0.12", 0.13", 0.14", 0.15", 0.16", 0.17", 0.18", 0.19", 0.2", 0.3", 0.4", 0.5", 0.6", 0.7", or 0.8". The narrowest diameter width of the bladder fluid lumen 126 may be within any range of diameter width, for instance, 0.08"-0.5", 0.07"-0.5", 0.08"-0.1", 0.07"-0.1", 0.07"-0.2", 0.09"-0.12", or 0.093"-0.118". The widest diameter width of a bladder fluid lumen 126 may be any diameter width, for instance, 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.101", 0.102", 0.103", 0.104", 0.105", 0.106", 0.107", 0.108", 0.109", 0.11", 0.11", 0.112", 0.113", 0.114", 0.115", 0.116", 0.117", 0.118", 0.119", 0.12", 0.13", 0.14", 0.15", 0.16", 0.17", 0.18", 0.19", 0.2", 0.3", 0.4", 0.5", 0.6", 0.7", or 0.8". The widest diameter width of the bladder fluid lumen 508 may be within any range of diameter width, for instance, 0.08"-0.5", 0.07"-0.5", 0.08"-0.1", 0.07"-0.1", 0.07"-0.2", 0.095"-0.2", 0.1"-0.2", 0.105"-0.2", 0.1"-0.12", 0.09"-0.12", or 0.099"-0.111".

The distance between the bladder delivery lumen 126 and the interior surface of the drug delivery lumen 122 may be, for instance 0.005", 0.006", 0.007", 0.008", 0.009", 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, and the like. The distance between the internal surface of the drug delivery lumen 122 and the interior surface of the bladder fluid lumen 126 may be within any range of distances, for instance, 0.005"-0.1", 0.005"-0.025", 0.005"-0.06", 0.011"-0.017", or 0.01"-0.02". The distance between the internal surface of the drug delivery lumen 122 and the interior surface of the bladder fluid lumen 126 may be the same as the distance between the internal surface of the inflation lumen 124 and the interior surface of the bladder fluid lumen 126 symmetrically.

The shortest distance between the interior of the bladder fluid lumen 126 and the exterior of the shaft 120 is the shortest distance between the exterior of the shaft 120 and the interior of the bladder fluid lumen 126. The shortest distance between the interior of the bladder fluid lumen 126 and the exterior of the shaft 120 may be any distance, for instance, 0.025", 0.026", 0.027", 0.028", 0.029", 0.03", 0.031", 0.032", 0.033", 0.034", 0.035", 0.036", 0.037", 0.038", 0.039", 0.04", 0.05", 0.06", 0.07", 0.08", 0.09", or 0.1". The shortest distance between the interior of the bladder fluid lumen 126 and the exterior of the shaft 120 may be within a range of distances, for instance, 0.025"-0.04", 0.025"-0.1", 0.029"-0.035", or 0.025"-0.1".

The drug fluid side hole 128 is a hole in the shaft 120, which provides open fluid access to the drug delivery lumen 122. The drug fluid side hole 128 may be in fluid communication with the drug delivery lumen 122 and the space between the interior surface of the drug delivery balloon 150 and the exterior of the inflation balloon 140. The drug fluid side hole 128 may provide fluid access for drugs fluids to transfer between the drug delivery lumen 122 and the drug delivery balloon 150. The drug fluid side hole may 128 be of any diameter at its widest point on the arcuate surface of the shaft, for instance, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", ⅛", ¼", 0.5", ¾", 1", 1.5", 2", and the like. The drug fluid side hole 128 may be one of any range of diameters at its widest point on the arcuate surface of the shaft, for instance, 0.071"-0.091", 0.085"-0.1", 0.1 mm-2 mm, 0.2 mm-0.5 mm, 0.5 mm-1 mm, 0.1 mm-5 mm, 1 mm-10 mm, 5 mm-15 mm, 5 mm-34 mm, 10 mm-15 mm, 12 mm-34 mm, 0.1 mm-34 mm, and the like.

The drug fluid side hole 128 may be located between the inflation fluid side hole 130 and the proximal end of the shaft 120, the drug fluid side hole 128 being proximal to the inflation fluid side hole 130. The drug fluid side hole 128 may be located substantially distally on the shaft such that the distance between the drug fluid side hole 128 and the distal end of the shaft 120 where the end cap 134 is placed represents less than, for instance 1%, 2%, 3%, 4%, 5%, 6%, 7%, 8%, 9%, 10%, 11%, 12%, 13%, 14%, 15%, 16%, 17%, 18%, 19%, or 20% of the total length of the shaft 120. The drug fluid side hole 128 may be located substantially distally on the shaft such that the distance between the drug fluid side hole 128 and the distal end of the shaft 120 where the end cap 134 is placed represents as little as, for instance a range of 1%-4%, 5%-8%, 5%-10%, 1%-10%, or 1%-20% of the total length of the shaft 120. The drug fluid side hole 128 may be located substantially distally on the shaft 120 such that the distance along the shaft 120 between the center of the drug fluid side hole 128 and the distal end of the shaft 120 where the end cap 134 is placed may be, for instance, 1 mm, 2 mm, 3 mm, 4 mm, 5 mm, 6 mm, 7 mm, 8 mm, mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, ¾", ½", ¾", 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1", 1.1", 1.11", 1.12", 1.13", 1.14", 1.15", 1.16", 1.17", 1.18", 1.19", 1.2", 1.21", 1¼", 1½", 1¾", 2", 3", 4", 5", 6", 7", 8", 9", 10" and the like. The drug fluid side hole 128 may be located substantially distally on the shaft such that the distance along the shaft between the center of the drug fluid side hole 128 and the distal end of the shaft 120 where the end cap 134 is placed may be within a range of distances, for instance, 0.25"-0.75", 0.5"-0.7", 0.5"-1", 0.25"-1.5", 0.9"-1.5", 0.5"-2", 0.25"-10", 0.3"-0.55", 0.3"-1.21", 0.3"-5", 0.8"-1.2", 0.8"-2", 0.8"-3", 0.6"-3", or 0.8"-4".

The inflation fluid side hole 130 is a hole in the shaft 120, which provides open fluid access to the inflation lumen 124. The inflation fluid side hole 130 may be in fluid communication with the inflation lumen 124 and the space between the interior surface of the inflation balloon 140 and the exterior surface of the shaft 120. The inflation fluid side hole 130 may provide fluid access for inflation fluids to transfer between the inflation lumen 124 and the inflation balloon 140. The inflation fluid side hole 130 may be of any diameter at its widest point on the arcuate surface of the shaft, for instance, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", ⅛", ½", 0.5", ¾", 1", 1.5", 2", and the like. The inflation fluid side hole 130 may be one of any range of diameters at its widest point on the arcuate surface of the shaft, for instance, 0.071"-0.091", 0.085"-0.1", 0.1 mm-2 mm, 0.2 mm-0.5 mm, 0.5 mm-1 mm, 0.1 mm-5 mm, 1 mm-10 mm, 5 mm-15 mm, 5 mm-34 mm, 10 mm-15 mm, 12 mm-34 mm, 0.1 mm-34 mm, and the like.

The inflation fluid side hole 130 may be located between the input the drug fluid side hole 128 and the drainage aperture 132. The inflation fluid side hole 130 may be located substantially distally on the shaft such that the distance between the inflation fluid side hole 130 and the distal end of the shaft 120 where the end cap 134 is placed represents as little as, for instance 1%, 2%, 3%, 4%, 5%, 6%, 7%, 8%, 9%, 10%, 11%, 12%, 13%, 14%, 15%, 16%, 17%, 18%, 19%, or 20% of the total length of the shaft. The inflation fluid side hole 130 may be located substantially distally on the shaft such that the distance between the inflation fluid side hole 130 and the distal end of the shaft 120 where the end cap 134 is placed represents as little as, for instance a range of 1%-4%, 5%-8%, 5%-10%, 1%-10%, or 1%-20% of the total length of the shaft. The inflation fluid side hole 130 may be located substantially distally on the shaft such that the distance along the shaft between the center of the inflation fluid side hole 130 and the distal end of the shaft 120 where the end cap 134 is placed may be, for instance, 1 mm, 2 mm, 3 mm, 4 mm, 5 mm, 6 mm, 7 mm, 8 mm, mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, ½", ½", 0.55", 0.56", 0.57", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", ¾", 1", 1¼", 1½", 1¾", 2", 3", 4", 5", 6", 7", 8", 9" or the like. The inflation fluid side hole 130 may be located substantially distally on the shaft 120 such that the distance along the shaft 120 between the center of the inflation fluid side hole 130 and the distal end of the shaft 120 where the end cap 134 is placed may be within a range of distances, for instance, 0.25"-0.75", 0.5"-0.7", 0.5"-1", 0.25"-1.5", or 0.25"-9".

The distance between the drug fluid side hole 128 and the inflation fluid side hole 130 along the shaft 120 may be, for instance, 1 mm, 2 mm, 3 mm, 4 mm, 5 mm, 6 mm, 7 mm, 8 mm, mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21", 2", 3", 4", 5", 6", 7", 8", or 9". The distance between the drug fluid side hole 128 and the inflation fluid side hole 130 along the shaft 120 may be within any range of distances, including, for instance, 0.2"-10", 0.2"-0.39", 0.3"-0.4", 0.3"-0.55", 0.3"-1.21", 0.3"-5", 0.8"-1.2", 0.8"-2", 0.8"-3", 0.6"-3", or 0.8"-4".

The drainage aperture 132 is a hole in the shaft 120, which provides bladder fluid access from the bladder to the shaft 120, and eventually an external bladder fluid reservoir. The drainage aperture 132 may be in fluid communication with the fluids in the bladder and the bladder fluid lumen 126. The fluids in the bladder may enter the bladder fluid lumen 126 via the drainage aperture 132, travel through the bladder fluid lumen 126, exit the bladder fluid output 114, and finally exit the system into a bladder fluid reservoir. The drainage aperture 132 may be of any diameter at the drainage aperture's 132 widest point on the arcuate surface of the shaft, for instance, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 0.07", 0.08", 0.09", 0.1", 0.11", 0.12", 0.13", 0.14", 0.15", 0.16", 0.17", 0.18", 0.19", 0.2", 0.21", 0.22", 0.23", 0.24", 0.25", 0.26", ⅛", ¾", 0.5", ¾", 1", 1.5", 2", and the like. The drainage aperture 132 may be one of any range of diameters at the drainage aperture's 132 widest point on the arcuate surface of the shaft, for instance, 0.1 mm-2 mm, 0.2 mm-0.5 mm, 0.5 mm-1 mm, 0.1 mm-5 mm, 1 mm-10 mm, 5 mm-15 mm, 5 mm-34 mm, 10 mm-15 mm, 12 mm-34 mm, 0.1 mm-34 mm, and the like. The drainage aperture 132 may be of any diameter at the drainage aperture's 132 narrowest point on the arcuate surface of the shaft, for instance, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 0.1", 0.11", 0.12", 0.13", 0.14", 0.15", 0.16", 0.17", 0.18", 0.19", 0.2", 0.21", 0.22", 0.23", 0.24", 0.25", 0.26", 0.27", 0.28", 0.29", 0.3", 0.31", 0.32", 0.4", ⅛", ¾", 0.5", ¾", 1", 1.5", 2", and the like. The drainage aperture 132 may be one of any range of diameters at the drainage aperture's 132 narrowest point on the arcuate surface of the shaft, for instance, 0.1"-0.25", 0.1"-0.3", 0.1"-0.5", 0.1 mm-2 mm, 0.2 mm-0.5 mm, 0.5 mm-1 mm, 0.1 mm-5 mm, 1 mm-10 mm, 5 mm-15 mm, 5 mm-34 mm, 10 mm-15 mm, 12 mm-34 mm, 0.1 mm-34 mm, and the like. The drainage aperture may be a Murphy Eye (sized +/−0.020").

The end cap 134 is a cap, which abuts the distal end of the shaft 120. The end cap 134 may have molded channel plugs to plug the lumens and prevent fluids from flowing out of the lumens at the distal end of the shaft 120. The end cap 134 may have plugs of the same diameters of the lumens that the plugs will block. In one embodiment, the end cap 134 may have a single plug only to fill the bladder fluid lumen 126. The end cap 134 may have substantially the same external diameter as the shaft 120.

The inflation balloon 140 is a balloon situated circumferentially around the shaft 120, which is inflated within the bladder to hold the catheter assembly system 100 in place by applying pressure on the bladder wall. The inflation balloon 140 may be a cylindrical sheet which can be situated about the shaft and coupled at different ends to create a fluid-tight seal for inflation. The space between the interior surface of the inflation balloon 140 and the shaft 120 may be in fluid communication with the inflation lumen 124 via the inflation side hole 130. The inflation balloon 140 may be inflated with an inflation fluid by an inflation device injecting inflation fluid into the inflation fluid input 110, the fluid travelling through the inflation lumen 124 through the inflation fluid side hole 130 to the inflation balloon 140. The inflation fluid may be any fluid, including, for instance, sterile saline, water, air, and the like. A drug fluid may be delivered to the space between the inflation balloon 140 and the drug delivery balloon. The inflation balloon 140 may be coupled to the shaft 120 along a distance of the shaft between a proximal point of coupling and a distal point of coupling, the distal point of coupling being between the drainage aperture 132 and the inflation fluid side hole 130 and the proximal point of coupling at a point between the drug fluid side hole 128 and the inflation fluid side hole 130.

The inflation balloon 140 may be partially covered by the drug delivery balloon 150, the portion of the drug deliver balloon 150 covering the inflation balloon 140 externally, such that inflating the inflation balloon 140 pushes the portion of the drug delivery balloon 150 covering the inflation balloon 140 outwards towards the bladder wall where drugs may be delivered by the drug delivery balloon 150. The portion of the inflation balloon 140 covered by the drug delivery balloon 150 may be on the proximal end of the inflation balloon 140. The drug delivery balloon 150 may cover any percentage of the surface of the drug delivery balloon 130 by surface area when the inflation balloon is inflated, including, 5%, 10%, 15%, 20%, 30%, 35%, 40%, 45%, 50%, 55%, 60%, 65%, 70%, 75%, 80%, 85%, greater than 5% but less than 95%, greater than 10% but less than 95%, greater than 15% but less than 80%, greater than 20% but less than 80%, greater than 20% but less than 70%, greater than 25% but less than 90%, less than 95%, less than 90%, less than 80%, less than 85%, less than 75%, less than 70%, less than 67%, less than 65%, less than 60%, less than 55%, less than 50%, less than 45%, less than 40%, less than 35%, less than 30%, less than 25%, less than 20%, when the inflation balloon is inflated at a pressure of 2.5 atm (where "atm" means atmospheres of pressure), the area of the drug delivery balloons with the holes located on a proximal portion of the drug delivery balloon, the proximal portion of the balloon representing the distal 5%, 10%, 15%, 20%, 30%, 35%, 40%, 45%, 50%, 55%, 60%, 65%, 70%, 75%, 80%, 85%, greater than 5% but less than 95%, greater than 10% but less than 95%, greater than 15% but less than 80%, greater than 20% but less than 80%, greater than 20% but less than 70%, greater than 25% but less than 90%, less than 95%, less than 90%, less than 80%, less than 85%, less than 75%, less than 70%, less than 67%, less than 65%, less than 60%, less than 55%, less than 50%, less than 45%, less than 40%, less than 35%, less than 30%, less than 25%, or less than 20% when the inflation balloon 140 is inflated to a pressure of 2.5 atm of the proximal surface area of the drug delivery balloon when inflated. The rows of holes on the drug delivery balloon 150 may overlap a percentage of surface area of the inflation balloon 140 of 5%, 10%, 15%, 20%, 30%, 35%, 40%, 45%, 50%, 55%, 60%, 65%, 70%, 75%, 80%, 85%, greater than 5% but less than 95%, greater than 10% but less than 95%, greater than 15% but less than 80%, greater than 20% but less than 80%, greater than 20% but less than 70%, greater than 25% but less than 90%, less than 95%, less than 90%, less than 80%, less than 85%, less than 75%, less than 70%, less than 67%, less than 65%, less than 60%, less than 55%, less than 50%, less than 45%, less than 40%, less than 35%, less than 30%, less than 25%, or less than 20% when the inflation balloon 140 is fully inflated at a pressure of 2.5 atm.

The inflation balloon 140 may have raised ridges, the ridges preventing the internal inflation balloon 140 surface from sticking to the shaft 120. The raised ridges may be located along the circumference of the interior of the inflation balloon 140 with ridges spaced every few distance increments along the length of the inflation balloon 140, such that the ridges may be concentric with the shaft 120. The inflation balloon 140 may also have ridges on its interior circumference in order to prevent sticking to the shaft 120. The raised ridges may be of any height or width, including, for instance, 0.005", 0.006", 0.007", 0.008", 0.009", 0.01", 0.011", 0.012", 0.013", 0.014", 0.04", 0.015", 0.016", 0.017", 0.018", 0.019", 0.02", 0.1 mm, 0.2 mm, 0.3 mm, 0.4 mm, 0.5 mm, 0.6 mm, 0.7 mm, 0.8 mm, 0.9 mm and the like. The ridge height or width may fall into ranges of height or width, for instance, 0.008"-0.02", 0.009"-0.02", 0.005"-0.02", or 0.1 mm-0.9 mm. In an embodiment, the ridge height and width is the same.

The inflation balloon 140 may be of any thickness, for instance, 0.008", 0.009", 0.01", 0.011", 0.012", 0.013", 0.014", 0.015", 0.2 mm, 0.21 mm, 0.22 mm, 0.23 mm, 0.24 mm, 0.25 mm, 0.254 m, 26 mm, 0.27 mm, and the like. The inflation balloon 140 thickness may be, for instance, in the ranges 0.005"-0.015", 0.009"-0.011", 0.008"-0.012", 0.2 mm-0.3 mm, and the like.

The drug delivery balloon 150 is a balloon situated circumferentially about the shaft 120, which distributes drug fluids to the surfaces of the bladder 105. The drug delivery balloon 150 may be a cylindrical sheet which can be situated about the shaft 120 and coupled at ends to the shaft 120 or the inflation balloon 140, in order to create a fluid-tight seal for drug delivery. The drug delivery balloon 150 may be a cylindrical sheet which can be situated about the shaft and/or the inflation balloon 140 and coupled at different ends to create a tight seal for drug delivery through holes in the drug delivery balloon 150. The space between the interior of the drug delivery balloon 150 and the exterior of the inflation balloon 140 may be in fluid communication with the drug delivery lumen 122 via the drug delivery hole 128. A drug fluid may be injected through the drug fluid input 112, travel through the drug delivery lumen 122, through the drug fluid side hole 128, through the space between the drug delivery balloon 150 and the inflation balloon 140 and through holes located on the drug delivery balloon 150.

The proximal end of a drug delivery balloon 150 may be affixed to the shaft 120 at a proximal coupling site located between the proximal end of the shaft and the drug fluid side hole 128. The drug deliver balloon 150 may be coupled to the inflation balloon's 140 external surface at a distal point of drug delivery balloon 150 coupling on the external surface of the inflation balloon 140. Alternatively, the drug delivery balloon's 150 distal coupling site may be distal to or coincident with the inflation balloon's 140 distal coupling site along the shaft or may be coupled to a coupling site between the drainage aperture 132 and the inflation fluid side hole 130. The distance along the shaft 120 between the distal point of coupling of the drug delivery balloon 150 and the inflation balloon's 140 distal coupling site may be, for instance, 1 mm, 2 mm, 3 mm, 4 mm, 5 mm, 6 mm, 7 mm, 8 mm, mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, ¼", ½", ¾", 1", 1¼", 1½", 1¾", 2", 3", 4", 5", 6", 7", 8", 9", 10", between 0.1 mm and 10 mm, between 0.1 mm and 1 mm, less than 10 mm, less than 1 mm, less than 5 mm, and the like.

The drug delivery balloon 150 may have raised ridges on the interior of the drug delivery balloon 150, the ridges preventing the internal drug delivery balloon 150 and external inflation balloon 140 surfaces from sticking together. The raised ridges may be located along the circumference of the interior of the drug delivery balloon 150 with ridges spaced every few distance increments along the length of the drug delivery balloon balloon 150, such that the ridges may be concentric with the shaft 120. The raised ridges may be of any height or width, including, for instance, 0.005", 0.006", 0.007", 0.008", 0.009", 0.01", 0.011", 0.012", 0.013", 0.014", 0.04", 0.015", 0.016", 0.017", 0.018", 0.019", 0.02", 0.1 mm, 0.2 mm, 0.3 mm, 0.4 mm, 0.5 mm, 0.6 mm, 0.7 mm, 0.8 mm, 0.9 mm and the like. The ridge height or width may fall into ranges of height or width, for instance, 0.008"-0.02", 0.009"-0.02", 0.005"-0.02", or 0.1 mm-0.9 mm. In an embodiment, the ridge height and width is the same.

The drug delivery balloon 150 may be of any thickness, for instance 0.007", 0.008", 0.009", 0.01", 0.011", 0.012", 0.013", 0.014", 0.015", 0.2 mm, 0.21 mm, 0.22 mm, 0.23 mm, 0.24 mm, 0.25 mm, 0.254 m, 26 mm, 0.27 mm, and the like. The drug delivery balloon 150 thickness may be, for instance, in the ranges 0.005"-0.015", 0.009"-0.011", 0.008"-0.012", 0.2 mm-0.3 mm, and the like.

The holes of the drug delivery balloon 150 may be of any diameter, including, for instance, 0.02", 0.03", 0.031", 0.032", 0.033", 0.034", 0.035", 0.036", 0.037", 0.038", 039", 0.04", 0.041", 0.042", 0.043", 0.044", 0.045", 0.046", 0.047", 0.048", 0.049", 0.05", 0.06", 0.07" 1 mm, 0.2 mm, 0.3 mm, 0.4 mm, 0.5 mm, 0.6 mm, 0.7 mm, 0.8 mm, 0.9 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.4 mm, 3.5 mm, 3.6 mm, 3.7 mm, 3.8 mm 3.9 mm, or 4 mm. The holes may be arranged in circumferential rows. The number of rows of holes may be, for instance, 1, 2, 3, 4, 5, 6, 7, 8, 9, 10, 11, 12, 13, 14, 15, 16, 17, 18, 19, 20 or 21 rows. The distance between rows (measured perpendicular to the rows along the balloon), may be, for instance, 0.1 mm, 0.2 mm, 0.3 mm, 0.4 mm, 0.5 mm, 0.6 mm, 0.7 mm, 0.8 mm, 0.9 mm, 1 mm, and the like. The shortest distance between the center of a hole in one row and the center of a hole in a nearest row may be 0.01", 0.02", 0.03", 0.031", 0.032", 0.033", 0.034", 0.035", 0.035", 0.036", 0.037", 0.038", 0.039", 0.04", 0.041", 0.042", 0.043", 0.044", 0.045", 0.046", 0.047", 0.048", 0.049", 0.05", 0.051", 0.052", and the like. The distances between rows of holes may be within ranges of distances, for instance, 0.03"-0.05", 0.035"-0.045", 0.01"-0.052", or 0.01"-0.05". The number of holes per row may be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 holes.

The drug balloon 150 may have an interior diameter, when completely deflated, that is substantially the same or slightly larger than the external diameter of the inflation balloon 140, in order to allow the drug balloon to easily conform above the surface of the deflated inflation balloon 140. For instance, the external diameter of the inflation balloon when deflated may be 0.15", 0.16", 0.17", 0.18", 0.19", 0.2", 0.21", 0.22" or 0.23". The diameter of the drug delivery balloon 150 may be 0.17", 0.18", 0.19", 0.2", 0.21", 0.22", 0.23", 0.24", or 0.25". The interior diameter of the drug delivery balloon 150 may be 0.19" or 0.2" in order to conform to an external diameter of the inflation balloon 140 of 0.19". The difference between the interior diameter of the drug delivery balloon 150 and the inflation balloon 140 may be accounted for by including the raised ridges on the interior of the drug delivery balloon.

The bladder 105 is an organ that collects and excretes urine from the human body. The bladder 105 may require a catheter for draining of fluids in certain circumstances. The bladder 105 may have a trigone area 107 comprising two ureteral orifices and the internal urethral orifice. The trigone area 107, when irritated can cause bladder 105 spasms. These spasms may be uncomfortable and may cause kinking in a bladder assembly. Elements of the catheter system 100 may be placed in a bladder 105 to allow fluids in the bladder 105 to flow through the catheter system 100. The bladder 105 may receive a drug solution from the catheter system 100 in order to limit spasms. The drug solution from the catheter system 100 may be exposed to the trigone in order to limit bladder spasm. Site-specific delivery of drug solutions to the trigone may be accomplished by administering the drug solutions via small holes in a drug inflation balloon 150 located at the site of the trigone when the inflation balloon 140 is inflated.

Drug fluid channel elements, such as the drug fluid input 112, the drug delivery lumen 122, the drug fluid side hole 128, and the space between the interior of the drug balloon 150 and the exterior of the inflation balloon 140, may all be in fluid communication. Bladder fluid channel elements, such as the bladder fluid input 114, bladder fluid lumen 126, and drainage aperture 132, may all be in fluid communication. Inflation fluid elements, such as the inflation input 110, the inflation fluid lumen 124, the inflation fluid side hole 130, and the space between the interior of the inflation fluid balloon 140 and the shaft 120, may all be in fluid communication. The drug fluid channel elements may not be in fluid communication with the bladder fluid channel elements or the inflation fluid channel elements. The bladder fluid channel elements may not be in fluid communication with the drug fluid channel elements and the inflation fluid channel elements. The inflation fluid channel elements may not be in fluid communication with the drug fluid channel elements and the bladder fluid channel elements.

Figure 2:
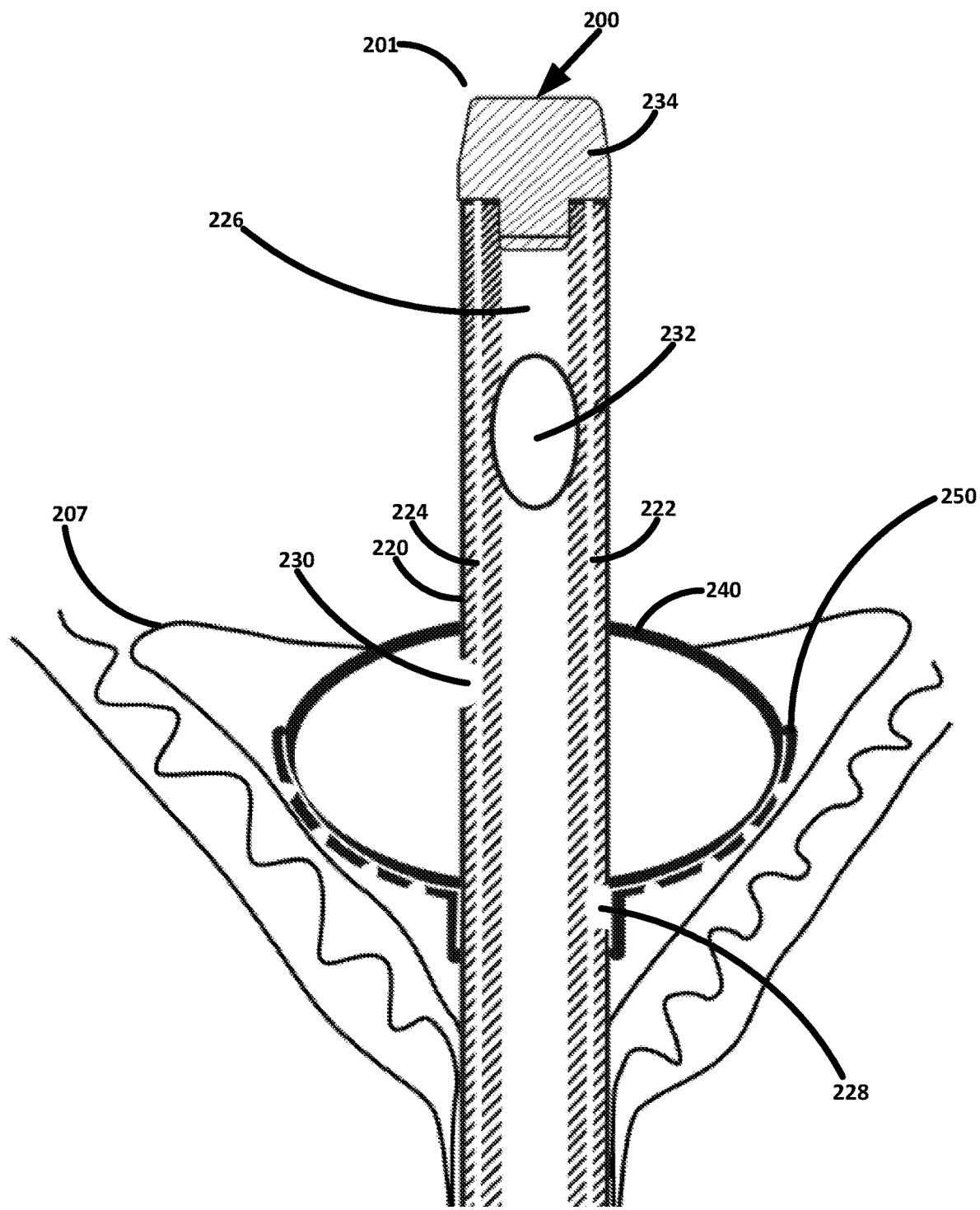
FIG. 2 shows a diagram of an interior bladder view of an embodiment of a distal portion of the catheter system 100 for drug delivery to a patient's bladder.

FIG. 2 shows a diagram of an interior bladder view of an embodiment of a distal portion of a catheter system 100 for drug delivery to a patient's bladder. The distal portion of a catheter system 200 may include a distal portion of the shaft 220, an end cap 234, an inflation balloon 240, a drug delivery balloon 250, a distal side 201, a bladder 205, and a trigone area 207. In other embodiments, the distal portion of a catheter system 200 may not have all of the elements or features listed and/or may have other elements or features instead of or in addition to those listed.

The distal portion of the shaft 220 is the distally located portion of a shaft. In an embodiment, the shaft may be, for instance, the shaft 120. The distal portion of the shaft 202 may include a drug delivery lumen 222, an inflation lumen 224, a bladder fluid lumen 226, a drug fluid side hole 228, an inflation side hole 230, a drainage aperture 232, and an end cap 234.

The drug delivery lumen 222 is a channel within the shaft 220 for communicating drug containing fluids from a drug fluid input to a drug delivery balloon 250. The drug delivery lumen 222 may be an embodiment of the drug delivery lumen 122. The inflation lumen 224 is a channel within the shaft 220 for communicating inflation fluids from an inflation fluid input to the inflation balloon 240. The inflation lumen 224 may be an embodiment of the inflation lumen 124. The bladder fluid lumen 226 is a lumen within the shaft 220 that allows fluid communication of bladder fluids between the bladder and an external bladder fluid reservoir. The bladder fluid lumen 226 may be an embodiment of the bladder fluid lumen 126. The drug fluid side hole 228 is a hole in the shaft 220, which provides open fluid access to the drug delivery lumen 222. The drug fluid side hole 228 may be an embodiment of the fluid side hole 128. The inflation fluid side hole 230 is a hole in the shaft 220, which provides open fluid access to the inflation lumen 224. The inflation fluid side hole 230 may be an embodiment of the inflation fluid side hole 130. The drainage aperture 232 is a hole in the shaft 220, which provides bladder fluid access from the bladder 205 to the shaft 220, and eventually an external bladder fluid reservoir. The drainage aperture may be an embodiment of the drainage aperture 132.

The end cap 234 is a cap, which abuts the distal end of the shaft 220. The end cap 234 may be an embodiment of the end cap 134.

The inflation balloon 240 is a balloon, which is inflated within the bladder to hold the catheter assembly system 100 in place by applying pressure on the bladder wall. The inflation balloon 240 may be an embodiment of the inflation balloon 140.

The drug delivery balloon 250 is a balloon, which distributes drug fluids to the surfaces of the bladder 205. The drug delivery balloon 250 may be an embodiment of the drug delivery balloon 150.

Figure 3:
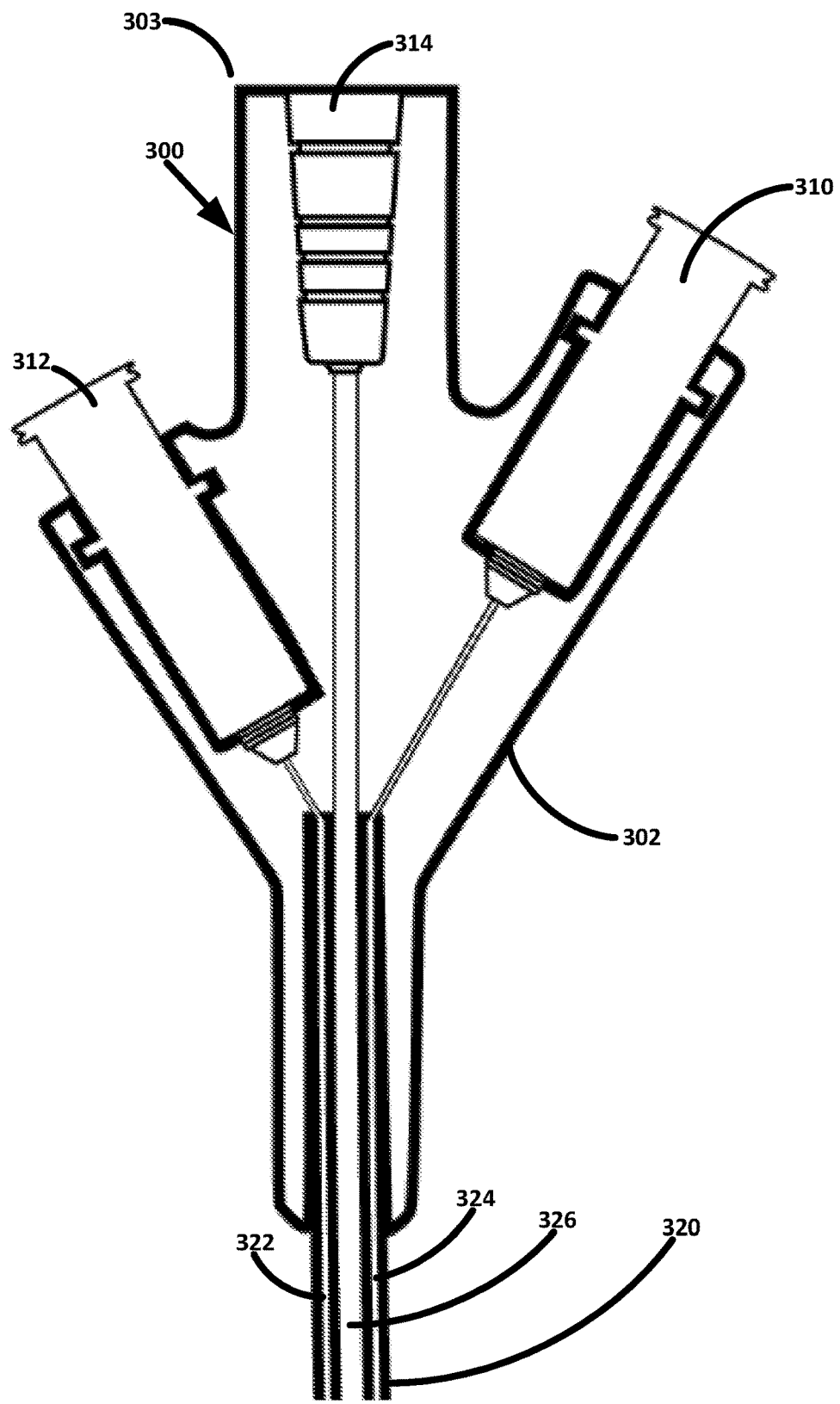
FIG. 3 shows a diagram of an embodiment of a proximal portion of the catheter system 100 for drug delivery to a patient's bladder.

FIG. 3 shows a diagram of an embodiment of a proximal portion of a catheter system 100 for drug delivery to a patient's bladder. The proximal portion of the catheter system 300 may include an input manifold 302 having a drug fluid input 312, an inflation fluid input 310, a bladder drainage output 314, a shaft 320, a drug delivery lumen 322, an inflation fluid lumen 324, a bladder fluid lumen 326, and a proximal side 303. The input manifold 302 may be an embodiment of the input manifold 102. In other embodiments, the proximal portion of the catheter system 300 may not have all of the elements or features listed and/or may have other elements or features instead of or in addition to those listed.

The drug fluid input 312 is an input, which receives drug-containing fluids (hereinafter "drug fluids") from a source. The drug fluid input 312 may be an embodiment of the drug fluid input 112. The inflation fluid input 310 is an input and output, through which inflation fluid is added or removed for the purposes of inflating or deflating an inflation balloon. The inflation input 312 may be an embodiment of the inflation fluid input 110. The bladder drainage output 314 is the output through which urinary bladder fluids and drainage are expelled from the catheter system. The bladder drainage output 314 may be an embodiment of the bladder drainage output 114. The proximal side 303 is a proximal side of the catheter 300. The proximal side 303 may be an embodiment of the proximal side 103. The shaft 320 is an elongate member with channels and holes to allow fluids to flow through to inflation and medication balloons. The shaft 320 may be an embodiment of the shaft 120. The drug delivery lumen 322 is a channel in the shaft 320 that allows drug fluids to flow through the shaft 320. The drug delivery lumen 322 may be an embodiment of the drug delivery lumen 122. The inflation lumen 324 is a channel in the shaft 320 that allows inflation fluid to flow through the shaft 320.

The inflation fluid lumen 324 may be an embodiment of the inflation fluid lumen 124. The bladder fluid lumen 326 is a channel in the shaft 320 that allows the flow of bladder fluids through the shaft 320. The bladder fluid lumen 326 may be an embodiment of the bladder fluid lumen 126.

Figure 4:
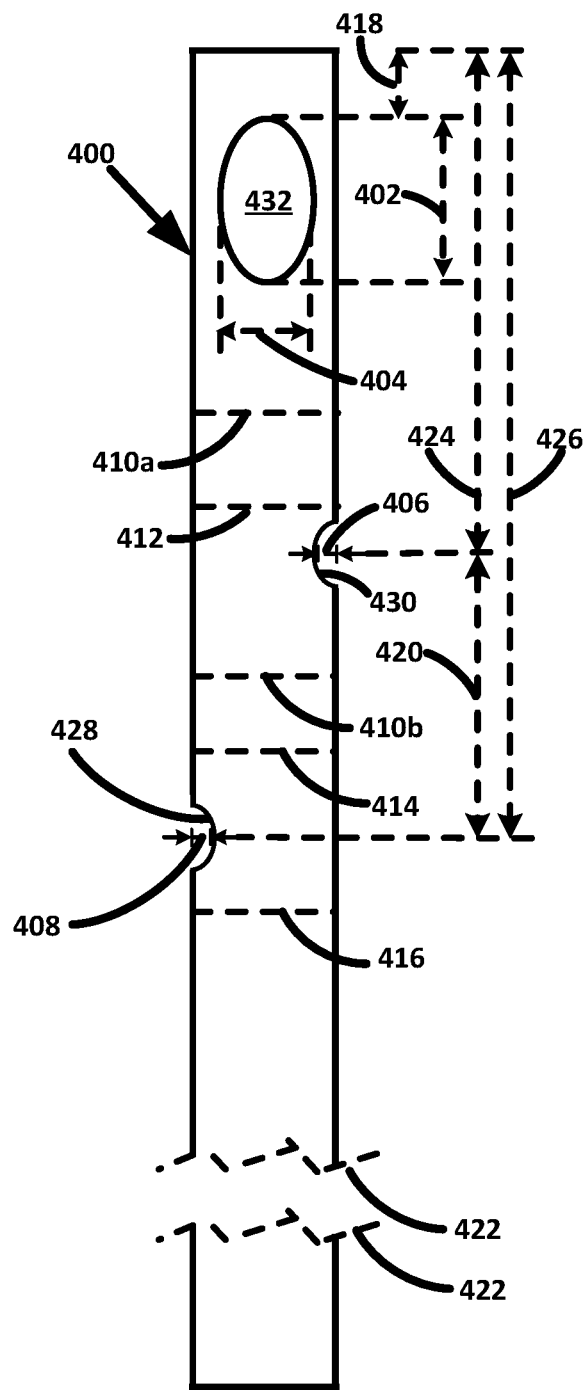
FIG. 4 shows a diagram of an embodiment of a distal portion of a shaft of the catheter system 100.

FIG. 4 shows a diagram of an embodiment of a distal portion of a shaft of the catheter system 100. The distal portion of the shaft of a catheter system 400 may include a widest diameter of a drainage aperture 402, narrowest diameter of a drainage aperture 404, a maximum depth of drug fluid side hole 406, a maximum depth of inflation fluid side hole 408, a distal drug balloon coupling site 410, a distal inflation balloon coupling site 412, a proximal inflation balloon coupling site 414, a drug delivery balloon proximal coupling site 416, a distance from the distal end of the shaft to the distal end of the drainage aperture 418, a distance between the drug fluid side hole and the inflation fluid side hole along the shaft 420, a cutoff 422, a distance from the distal end of the shaft to the center of the inflation fluid side hole 424, a distance from the distal end of the shaft to the center of the drug fluid side hole 426, a drug fluid side hole 428, an inflation fluid side hole 430, and a drainage aperture 432. In other embodiments, the distal portion of a shaft of a catheter system 400 may not have all of the elements or features listed and/or may have other elements or features instead of or in addition to those listed. The shaft 400 may be an embodiment of the shaft 120.

For the purposes of this section, the distal end of the shaft 400 may not include an end cap, so the measurements may be taken from the distal edge of the shaft 400 itself absent the end cap 134.

The drainage aperture 432 is an orifice in a catheter system shaft 400, which allows urine to flow from the bladder to the catheter system. The widest diameter of a drainage aperture 402 is the largest diameter of a drainage aperture on the surface of the shaft 400. The drainage aperture 432 may be of any diameter at the drainage aperture's 432 widest point on the arcuate surface of the shaft, for instance, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 0.07", 0.08", 0.09", 0.1", 0.11", 0.12", 0.13", 0.14", 0.15", 0.16", 0.17", 0.18", 0.19", 0.2", 0.21", 0.22", 0.23", 0.24", 0.25", 0.26", ⅛", ¼", 0.5", ¾", 1", 1.5", 2", and the like. The drainage aperture 132 may be one of any range of diameters at the drainage aperture's 132 widest point on the arcuate surface of the shaft, for instance, 0.1 mm-2 mm, 0.2 mm-0.5 mm, 0.5 mm-1 mm, 0.1 mm-5 mm, 1 mm-10 mm, 5 mm-15 mm, 5 mm-34 mm, 10 mm-15 mm, 12 mm-34 mm, 0.1 mm-34 mm, and the like.

The narrowest diameter of a drainage aperture 404 is the narrowest diameter of a drainage aperture along the length of the shaft. The drainage aperture 432 may be of any diameter at the drainage aperture's 432 narrowest point on the arcuate surface of the shaft, for instance, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 0.1", 0.11", 0.12", 0.13", 0.14", 0.15", 0.16", 0.17", 0.18", 0.19", 0.2", 0.21", 0.22", 0.23", 0.24", 0.25", 0.26", ⅛", ¼", 0.5", ¾", 1", 1.5", 2", and the like. The drainage aperture 132 may be one of any range of diameters at the drainage aperture's 132 narrowest point on the arcuate surface of the shaft, for instance, 0.1 mm-2 mm, 0.2 mm-0.5 mm, 0.5 mm-1 mm, 0.1 mm-5 mm, 1 mm-10 mm, 5 mm-15 mm, 5 mm-34 mm, 10 mm-15 mm, 12 mm-34 mm, 0.1 mm-34 mm, and the like.

The maximum depth of inflation fluid side hole 406 is the maximum depth of the hole measured from the surface of the shaft 400 closest to the inflation fluid lumen, to the internal surface of the inflation fluid lumen that is furthest from the surface of the shaft 400 closest to the inflation fluid lumen. The maximum depth of inflation fluid side hole 406 may be any depth, for instance, 0.06", 0.07", 0.071", 0.072", 0.073", 0.074", 0.075", 0.076", 0.077", 0.078", 0.079", 0.08", 0.081", 0.082", 0.083", 0.084", 0.085", 0.086", 0.087", 0.089", 0.09", 0.1", 0.15" or 0.2". The maximum depth of inflation fluid side hole 406 may be within any range of depth, for instance, 0.06"-0.1", 0.07"-0.2", 0.071"-0.1", 0.071"-0.089", 0.06"-0.2", 0.06"-3", 0.06"-0.4" or the like.

The maximum depth of drug fluid side hole 408 is the maximum depth of the hole measured from the surface of the shaft 400 closest to the drug delivery lumen, to the internal surface of the drug delivery lumen that is furthest from the surface of the shaft 400 closest to the drug delivery lumen. The maximum depth of drug fluid side hole 408 may be any depth, for instance, 0.06", 0.07", 0.071", 0.072", 0.073", 0.074", 0.075", 0.076", 0.077", 0.078", 0.079", 0.08", 0.081", 0.082", 0.083", 0.084", 0.085", 0.086", 0.087", 0.089", 0.09", 0.1", 0.15" or 0.2". The maximum depth of drug fluid side hole 408 may be within any range of depth, for instance, 0.06"-0.1", 0.07"-0.2", 0.071"-0.1", 0.071"-0.089", 0.06"-0.2", 0.06"-3", 0.06"-0.4" or the like.

The distal drug balloon coupling site 410 is the most distal site along the shaft at which the inflation balloon is coupled. The distal drug balloon coupling site 410 may be on the shaft between the drainage aperture 432 and the drug fluid side hole 428 in embodiment 410a. Alternatively or additionally, the distal drug balloon coupling site 410 may be between along the inflation balloon 410b, for instance, between the distal inflation balloon coupling and the proximal inflation balloon coupling. The distal drug balloon coupling site 410 may be any distal drug balloon coupling distance from the distal end of the shaft 424, for instance, 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1", 1.1", 1.2", 1.3", 1.4", 1", 2", 3", 4", or 5". The distal drug balloon coupling site 410 may be in any range of distances from the distal end of the shaft, for instance, 0.3"-0.6", 0.3"-0.5", 0.3"-0.4", 0.4"-0.6", 0.2"-0.6", 0.2"-1.4", 0.2"-5", or 0.55"-1.4".

The distal inflation balloon coupling site 412 is the distal most site along the shaft at which the inflation balloon is coupled to the shaft. The distal inflation balloon coupling site 412 may be on the shaft between the drainage aperture 432 and the inflation side hole 430. The distal inflation balloon coupling site 412 may be any distance from the distal end of the shaft, for instance, 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1", 1.1", 1.2", 1.3", 1.4", 2", 3", 4", or 5". The distal inflation balloon coupling site 412 may be any range of distances from the distal end of the shaft, for instance, 0.3"-0.6", 0.3"-1", 0.3"-1.4", 0.55"-1", 0.6"-1", 0.6"-0.95", 0.6"-2", 0.6"-3", 0.6"-4" and the like.

A proximal inflation balloon coupling site 414 is the proximal most site along the shaft 120 at which the inflation balloon is coupled to the shaft. The proximal inflation balloon coupling site 414 may be on the shaft between the inflation side hole 430 and the drug fluid side hole 428. The proximal inflation balloon coupling site 414 may be any distance from the distal end of the shaft, for instance, 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21", 2", 3", 4", or 5". The proximal inflation balloon coupling site 414 may be within any range of distances from the distal end of the shaft, for instance, 0.3"-0.55", 0.3"-1.21", 0.3"-5", 0.8"-1.2", 0.8"-2", 0.8"-3", 0.6"-3", or 0.8"-4".

A drug delivery balloon proximal coupling site 416 is the proximal most site of coupling for the drug delivery balloon in the catheter system. The drug delivery balloon coupling site proximal coupling site 416 may be between the proximal end of the shaft 120 and the drug fluid side hole 128. The drug delivery balloon proximal coupling site 416 may be any distance from the distal end of the shaft, for instance, 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21", 2", 3", 4" or 5". The drug delivery balloon proximal coupling site 416 may be within any range of distances from the distal end of the shaft, for instance, 0.3"-1.21", 0.3"-5", 0.55"-1", 0.6"-1", 0.6"-0.95", 0.6"-2", 0.6"-3", 0.6"-4", 0.8"-1.2", 0.8"-2", 0.8"-3", 0.6"-3", 0.8"-4", 0.55"-4", or 0.55"-5".

The distance from the distal end of the shaft to the distal end of the drainage aperture 418 is the distance from the distal end of the shaft to the drainage aperture 432. The distance from the distal end of the shaft to the distal end of the drainage aperture 418 may be, for instance, 0.07", 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.11", 0.12", 0.13", 0.14", 0.15", 0.16", 0.17", 0.18", 0.19", 0.2", 0.3", 0.4", 0.5", 0.6", 0.7", 0.8", or within a range of 0.07"-0.8", 0.07"-0.12", 0.07"-0.09", or 0.07"-0.1".

The distance between the drug fluid side hole and the inflation fluid side hole along the shaft 420 is a distance between the center of the drug fluid side hole 428 and the center of the inflation fluid side hole 430 as if the two were on the same side. The distance is parallel to the length of the shaft 400. The distance between the drug fluid side hole and the inflation fluid side hole 420 may be, for instance, 1 mm, 2 mm, 3 mm, 4 mm, 5 mm, 6 mm, 7 mm, 8 mm, mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 0.2", 0.21", 0.22", 0.23", 0.24", 0.25", 0.26", 0.27", 0.28", 0.29", 0.3", 0.31", 0.32", 0.33", 0.34", 0.35", 0.36", 0.37", 0.38", 0.39", ½", ½", ¾", 1", 1¼", 1½", 1¾", 2", 3", 4", 5", 6", 7", 8", 9", 10" and the like. The distance between the drug fluid side hole and the inflation fluid side hole along the shaft 400 may be within any range of distances, including, for instance, 0.2"-10", 0.2"-0.39", 0.2"-0.4" or 0.3"-0.4".

The cutoff 422 is a virtual representation that the image is not to scale by showing that the entirety of the shaft would not fit in the page if presented to scale.

The distance from the distal end of the shaft to the center of the inflation fluid side hole 424 is the distance from the distal end of the shaft 120 to the center of the inflation hole 130. The distance from the distal end of the shaft to the center of the inflation fluid side hole 424 may be 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21", 2", 3", 4", or 5". The distance from the distal end of the shaft to the center of the inflation fluid side hole 424 may be within any range of distances from the distal end of the shaft, for instance, 0.3"-0.55", 0.3"-1.21", 0.3"-5", 0.8"-1.2", 0.8"-2", 0.8"-3", 0.6"-3", or 0.8"-4".

The distance from the distal end of the shaft to the center of the drug fluid side hole 426, is the distance from the distal end of the shaft 120 to the center of the drug fluid side hole 128. The distance from the distal end of the shaft to the center of the drug fluid side hole 424 may be 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21", 2", 3", 4", or 5". The distance from the distal end of the shaft to the center of the drug fluid side hole 426 may be within any range of distances from the distal end of the shaft, for instance, 0.3"-0.55", 0.3"-1.21", 0.3"-5", 0.8"-1.2", 0.8"-2", 0.8"-3", 0.6"-3", or 0.8"-4".

The drug fluid side hole 428 is a hole in the shaft 400, which provides open fluid access to the drug delivery lumen. The drug fluid side hole 428 may be an embodiment of the drug fluid side hole 128.

The inflation fluid side hole 430 is a hole in the shaft 400, which provides open fluid access to the inflation lumen. The inflation fluid side hole 430 may be an embodiment of the inflation fluid side hole 130.

The drainage aperture 432 is a hole in the shaft 400, which provides bladder fluid access from the bladder to the shaft 400, and eventually an external bladder fluid reservoir. The drainage aperture 432 may be an embodiment of the drainage aperture 132.

Figure 5:
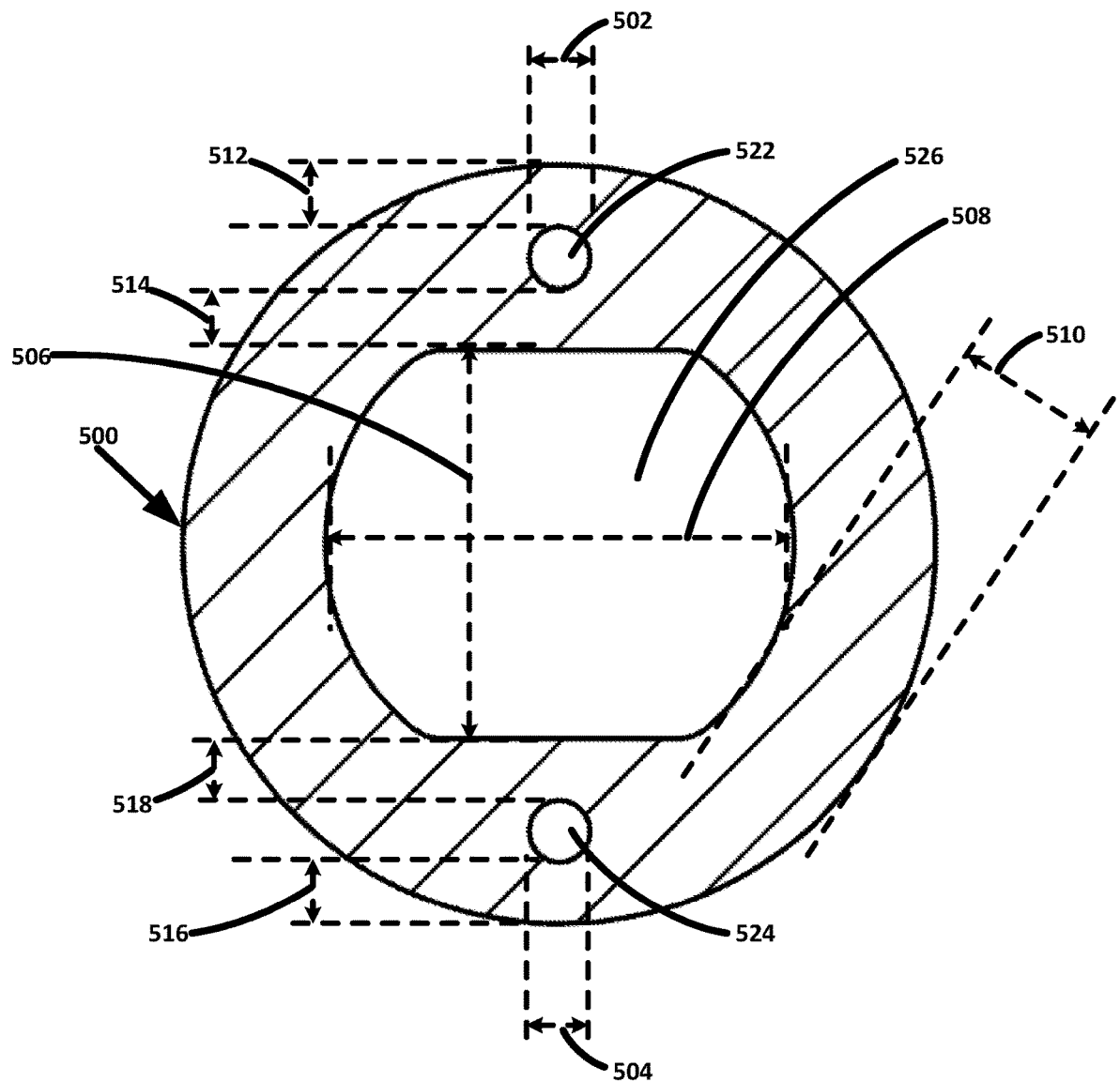
FIG. 5 shows a diagram of an embodiment of a cross sectional view of a shaft of the catheter system 100.

FIG. 5 shows a diagram of an embodiment of a cross sectional view of a shaft of the catheter system 100. The shaft of the catheter system 500 has a diameter of a drug delivery lumen 502, a diameter of an inflation lumen 504, a narrowest internal diameter width of a bladder fluid lumen 506, a widest diameter width of a bladder fluid lumen 508, a shortest distance between the interior of the bladder fluid lumen and the exterior of the shaft 510, a shortest distance between the external surface of the shaft and the interior of the drug delivery lumen 512, a distance between the internal surface of the drug delivery lumen and the interior surface of the bladder fluid lumen 514, a shortest distance between the external surface of the shaft and the interior of the inflation lumen 516, a distance between the internal surface of the drug delivery lumen and the interior surface of the inflation lumen 518, a drug delivery lumen 522, an inflation fluid lumen 524, and a bladder fluid lumen 526. In other embodiments, the shaft of a catheter system 500 may not have all of the elements or features listed and/or may have other elements or features instead of or in addition to those listed. The shaft 500 may be an embodiment of the shaft 120.

The diameter of a drug delivery lumen 502 is the diameter of a drug delivery lumen 522 within a shaft 500. The diameter of a drug delivery lumen 502 may be any diameter, including, for instance, a diameter of 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, and the like. The diameter of a drug delivery lumen 502 may have any internal diameter range of, for instance, 0.005"-0.02", 0.011"-0.0147", 0.01"-0.05", 0.01"-0.06", 0.02"-0.04", 0.02"-0.05", 0.03"-0.044", 0.04"-0.053", 0.02"-0.06", 0.02"-0.053", 0.2 mm-0.4 mm, 0.1 mm-0.5 mm, 0.27 mm-0.44 mm, 0.5 mm-0.8 mm, 0.5 mm-1.5 mm, 0.5 mm-1 mm, 0.7 mm-1 mm, 0.7 mm-1.5 mm, or 0.7 mm-1.6 mm.

The diameter of an inflation lumen 504 is the diameter of an inflation lumen 524 within a shaft. The diameter of an inflation lumen 504 is the diameter of an inflation lumen 524 within a shaft 500. The diameter of an inflation lumen 504 may be any diameter, including, for instance, a diameter of 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, and the like. The diameter of a drug delivery lumen 504 may be in a range of, for instance, 0.005"-0.02", 0.011"-0.0147", 0.01"-0.05", 0.01"-0.06", 0.02"-0.04", 0.02"-0.05", 0.03"-0.044", 0.04"-0.053", 0.02"-0.06", 0.02"-0.053", 0.2 mm-0.4 mm, 0.1 mm-0.5 mm, 0.27 mm-0.44 mm, 0.5 mm-0.8 mm, 0.5 mm-1.5 mm, 0.5 mm-1 mm, 0.7 mm-1 mm, 0.7 mm-1.5 mm, or 0.7 mm-1.6 mm.

The narrowest diameter width of a bladder fluid lumen 506 is the narrowest diameter width of the bladder fluid lumen 526 within the shaft 500. The narrowest diameter width of the bladder fluid lumen 506 may be any diameter width, for instance, 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.11", 0.12", 0.13", 0.14", 0.15", 0.16", 0.17", 0.18", 0.19", 0.2", 0.3", 0.4", 0.5", 0.6", 0.7", or 0.8". The narrowest diameter width of the bladder fluid lumen 506 may be within any range of diameter width, for instance, 0.08"-0.5", 0.07"-0.5", 0.08"-0.1", 0.07"-0.1", 0.07"-0.2", 0.09"-0.12", or 0.093"-0.118".

The widest diameter width of a bladder fluid lumen 508 is the widest diameter width of the bladder fluid lumen 526 within the shaft 500. The widest diameter width of a bladder fluid lumen 508 may be any diameter width, for instance, 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.101", 0.102", 0.103", 0.104", 0.105", 0.106", 0.107", 0.108", 0.109", 0.11", 0.11", 0.112", 0.113", 0.114", 0.115", 0.116", 0.117", 0.118", 0.119", 0.12", 0.13", 0.14", 0.15", 0.16", 0.17", 0.18", 0.19", 0.2", 0.3", 0.4", 0.5", 0.6", 0.7", or 0.8". The widest diameter width of the bladder fluid lumen 508 may be within any range of diameter width, for instance, 0.08"-0.5", 0.07"-0.5", 0.08"-0.1", 0.07"-0.1", 0.07"-0.2", 0.095"-0.2", 0.1"-0.2", 0.105"-0.2", 0.1"-0.12", 0.09"-0.12", or 0.099"-0.111".

The shortest distance between the interior of the bladder fluid lumen and the exterior of the shaft 510 is the shortest distance between the exterior of the shaft 500 and the interior of the bladder fluid lumen 526. The shortest distance between the interior of the bladder fluid lumen and the exterior of the shaft 510 may be any distance, for instance, 0.025", 0.026", 0.027", 0.028", 0.029", 0.03", 0.031", 0.032", 0.033", 0.034", 0.035", 0.036", 0.037", 0.038", 0.039", 0.04", 0.05", 0.06", 0.07", 0.08", 0.09", or 0.1". The shortest distance between the interior of the bladder fluid lumen and the exterior of the shaft 510 may be within a range of distances, for instance, 0.025"-0.04", 0.025"-0.1", 0.029"-0.035", or 0.025"-0.1".

The shortest distance between the external surface of the shaft and the interior of the drug delivery lumen 512 is the shortest distance between the external surface of the shaft 500 and the interior of the drug delivery lumen 522. The shortest distance between the external surface of the shaft and the interior of the drug delivery lumen 512 may be any distance, for instance, 0.005", 0.006", 0.007", 0.008", 0.009", 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, and the like. The shortest distance between the external surface of the shaft and the interior of the drug delivery lumen 512 may be within any range of distances, for instance, 0.005"-0.1", 0.005"-0.025", 0.005"-0.06", 0.011"-0.017", or 0.01"-0.02". The shortest distance between the external surface of the shaft and the interior of the drug delivery lumen 512 may be the same as the shortest distance between the external surface of the shaft and the interior of the inflation lumen 516 symmetrically about the bladder fluid lumen 126.

The distance between the internal surface of the drug delivery lumen and the interior surface of the bladder fluid lumen 514 is the distance between the internal surface of the drug delivery lumen 522 and the interior surface of the bladder fluid lumen 526. The distance between the internal surface of the drug delivery lumen and the interior surface of the bladder fluid lumen 514 may be any distance, for instance, 0.005", 0.006", 0.007", 0.008", 0.009", 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, and the like. The distance between the internal surface of the drug delivery lumen and the interior surface of the bladder fluid lumen 514 may be within any range of distances, for instance, 0.005"-0.1", 0.005"-0.025", 0.005"-0.06", 0.011"-0.017", or 0.01"-0.02". The distance between the internal surface of the drug delivery lumen and the interior surface of the bladder fluid lumen 514 may be the same as the distance between the internal surface of the inflation lumen 524 and the interior surface of the bladder fluid lumen 526 symmetrically about the bladder fluid lumen 526.

The shortest distance between the external surface of the shaft and the interior of the inflation lumen 516 is the shortest distance between the external surface of the shaft 500 and the interior of the inflation lumen 524. The shortest distance between the external surface of the shaft and the interior of inflation lumen 516 may be any distance, for instance, 0.005", 0.006", 0.007", 0.008", 0.009", 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, and the like. The shortest distance between the external surface of the shaft and the interior of the drug delivery lumen 512 may be within any range of distances, for instance, 0.005"-0.1", 0.005"-0.025", 0.005"-0.06", 0.011"-0.017", or 0.01"-0.02". The shortest distance between the external surface of the shaft and the interior of the drug delivery lumen 512 may be the same as the shortest distance between the external surface of the shaft and the interior of the inflation lumen 516 symmetrically about the bladder fluid lumen 126.

The distance between the internal surface of the drug delivery lumen and the interior surface of the bladder fluid lumen 518 is the distance between the internal surface of the inflation lumen 524 and the interior surface of the bladder fluid lumen 526. The distance between the internal surface of the inflation lumen and the interior surface of the bladder fluid lumen 518 may be any distance, for instance, 0.005", 0.006", 0.007", 0.008", 0.009", 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, and the like. The distance between the internal surface of the inflation lumen and the interior surface of the bladder fluid lumen 518 may be within any range of distances, for instance, 0.005"-0.1", 0.005"-0.025", 0.005"-0.06", 0.011"-0.017", or 0.01"-0.02". The distance between the internal surface of the inflation lumen and the interior surface of the bladder fluid lumen 518 may be the same as the distance between the internal surface of the drug delivery lumen and the interior surface of the bladder fluid lumen 526 symmetrically about the bladder fluid lumen 526.

The drug delivery lumen 522 is a channel within the shaft 500 for communicating drug containing fluids from a drug fluid input to a drug delivery balloon. The drug delivery lumen 522 may be an embodiment of drug delivery lumen 122.

The inflation fluid lumen 524 is a channel within the shaft 500 for communicating inflation fluids from an inflation fluid input to an inflation balloon. The inflation fluid lumen 524 may be an embodiment of inflation fluid lumen 124.

The bladder fluid lumen 526 is a lumen within the shaft 120 that allows fluid communication of bladder fluids between the bladder and an external bladder fluid reservoir. The bladder fluid lumen 526 may be an embodiment of the bladder fluid lumen 126.

Figure 6:
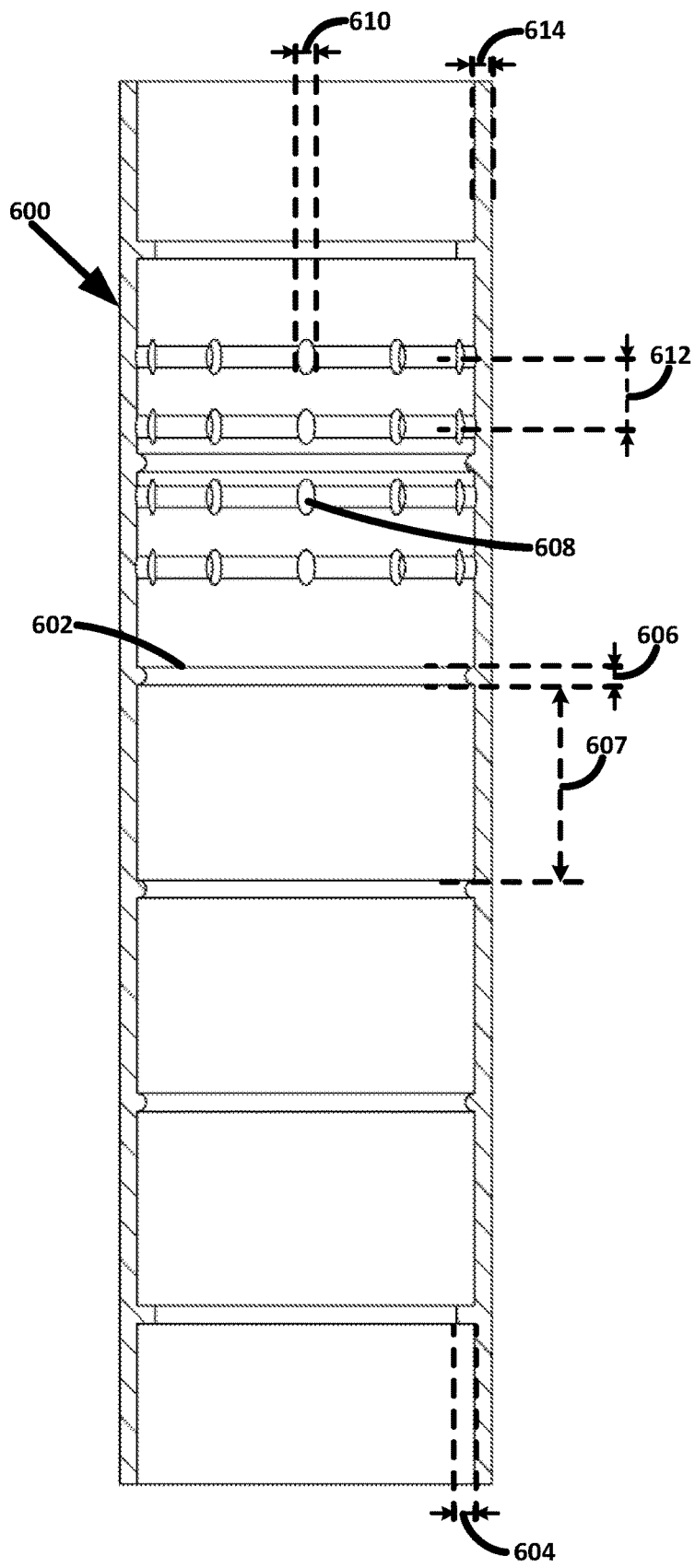
FIG. 6 shows a side view diagram of an embodiment of a drug delivery balloon of the catheter system 100 in a deflated state.

FIG. 6 shows a side view diagram of an embodiment of a drug delivery balloon of the catheter system 100 in a deflated state. The drug delivery balloon 600 may have ridges 602, a ridge height 604, a ridge width 606, a distance between ridges 607, holes 608, diameters of holes 610, distances between rows of holes 612, and a thickness of drug delivery balloon 614. In other embodiments, the drug delivery balloon 600 may not have all of the elements or features listed and/or may have other elements or features instead of or in addition to those listed. The drug delivery balloon 600 may be an embodiment of drug delivery balloon 150.

Ridges 602 are ridges within the balloons that provide support and prevent sticking of the layers of material to allow for drug delivery. The ridges 602 may be located along the circumference of the interior of the drug delivery balloon 600 with ridges 602 spaced every few distance increments along the length of the drug delivery balloon 600, such that the ridges may be concentric with the shaft.

The ridge height 604 is the height of the ridges 602. The raised ridge height 604 may be of any height, including, for instance, 0.005", 0.006", 0.007", 0.008", 0.009", 0.01", 0.011", 0.012", 0.013", 0.014", 0.04", 0.015", 0.016", 0.017", 0.018", 0.019", 0.02", 0.1 mm, 0.2 mm, 0.3 mm, 0.4 mm, 0.5 mm, 0.6 mm, 0.7 mm, 0.8 mm, 0.9 mm and the like. The raised ridge height 604 may fall into ranges of height, for instance, 0.008"-0.02", 0.009"-0.02", 0.005"-0.02", or 0.1 mm-0.9 mm.

The ridge width 606 is the width of a ridge 602. The ridge width 606 may be, for instance, 0.005", 0.006", 0.007", 0.008", 0.009", 0.01", 0.011", 0.012", 0.013", 0.014", 0.04", 0.015", 0.016", 0.017", 0.018", 0.019", 0.02", 0.1 mm, 0.2 mm, 0.3 mm, 0.4 mm, 0.5 mm, 0.6 mm, 0.7 mm, 0.8 mm, 0.9 mm and the like. The ridge width 604 may fall into ranges of width, for instance, 0.008"-0.02", 0.009"-0.02", 0.005"-0.02", or 0.1 mm-0.9 mm.

The distance between ridges 607 is the distance between ridges 602. The distance between ridges 607 may be, for instance, 0.07", 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.101", 0.102", 0.103", 0.104", 0.105", 0.106", 0.107", 0.108", 0.109", 0.11", 0.11", 0.112", 0.113", 0.114", 0.115", 0.116", 0.117", 0.118", 0.119", 0.12", 0.13", 0.14", 0.15", 0.16", 0.17", 0.18", 0.19", 0.2", 0.3", 0.4", 0.5", 0.6", 0.7", or 0.8". The distance between ridges 607 may be within any range of distances, for instance, 0.08"-0.5", 0.07"-0.5", 0.08"-0.1", 0.07"-0.1", 0.07"-0.2", 0.095"-0.2", 0.1"-0.2", 0.105"-0.2", 0.1"-0.12", 0.09"-0.12", or 0.099"-0.111".

The holes 608 are holes in the drug delivery balloon 600 through which drug fluids may flow. The holes 608 may be circular shaped or may be ovoid shape. The diameters or holes 610 are the minimum diameters (the minimum length across the hole along the surface of the shaft 120) of the holes 608. The diameters of holes 610 may be, for instance, 0.001", 0.01" 0.02", 0.03", 0.031", 0.032", 0.033", 0.034", 0.035", 0.036", 0.037", 0.038", 039", 0.04", 0.041", 0.042", 0.043", 0.044", 0.045", 0.046", 0.047", 0.048", 0.049", 0.05", 0.06", 0.07", 0.1 mm, 0.2 mm, 0.3 mm, 0.4 mm, 0.5 mm, 0.6 mm, 0.7 mm, 0.8 mm, 0.9 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.4 mm, 3.5 mm, 3.6 mm, 3.7 mm, 3.8 mm 3.9 mm, 4 mm, or ranges within 0.001"-0.1", 0.01"-0.1", 0.02"-0.05", 0.02"-0.07", 0.1 mm-4 mm, 0.1 mm-3 mm, or 0.1 mm-2 mm. The holes 608 may be arranged in circumferential rows along the circumference of the drug delivery balloon 600. The number of rows of holes may be, for instance, 1, 2, 3, 4, 5, 6, 7, 8, 9, 10, 11, 12, 13, 14, 15, 16, 17, 18, 19, 20 or 21 rows. The number of holes per row may be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 holes. The holes 608 may only be situated on the balloon in places where the holes will interaction with the bladder 105.

The distances between rows of holes 612 are the shortest distance between the center of a hole in one row and the center of a hole within the same plane parallel to the surface of the balloon (when the inflation balloon is deflated) in an adjacent row. The distances between rows of holes 612 may be, for instance, 0.03", 0.031", 0.032", 0.033", 0.034", 0.035", 0.036", 0.037", 0.038", 0.039", 0.04", 0.041", 0.042", 0.043", 0.044", 0.045", 0.046", 0.047", 0.048", 0.049", 0.05", 0.051", or 0.052". The distances between rows of holes 612 may be within ranges of distances, for instance, 0.03"-0.05", 0.035"-0.045", 0.01"-0.052", 0.01"-0.05", or 0.01"-0.2".

The thickness of drug delivery balloon 614 is the thickness of the membrane that forms the drug delivery balloon 600. The thickness of drug delivery balloon 614 may be, for instance 0.007", 0.008", 0.009", 0.01", 0.011", 0.012", 0.013", 0.014", 0.015", 0.2 mm, 0.21 mm, 0.22 mm, 0.23 mm, 0.24 mm, 0.25 mm, 0.254 m, 26 mm, 0.27 mm, and the like. The drug delivery balloon thickness 614 may be, for instance, in the ranges 0.005"-0.015", 0.009"-0.011", 0.008"-0.012", 0.2 mm-0.3 mm, and the like.

Figure 7:
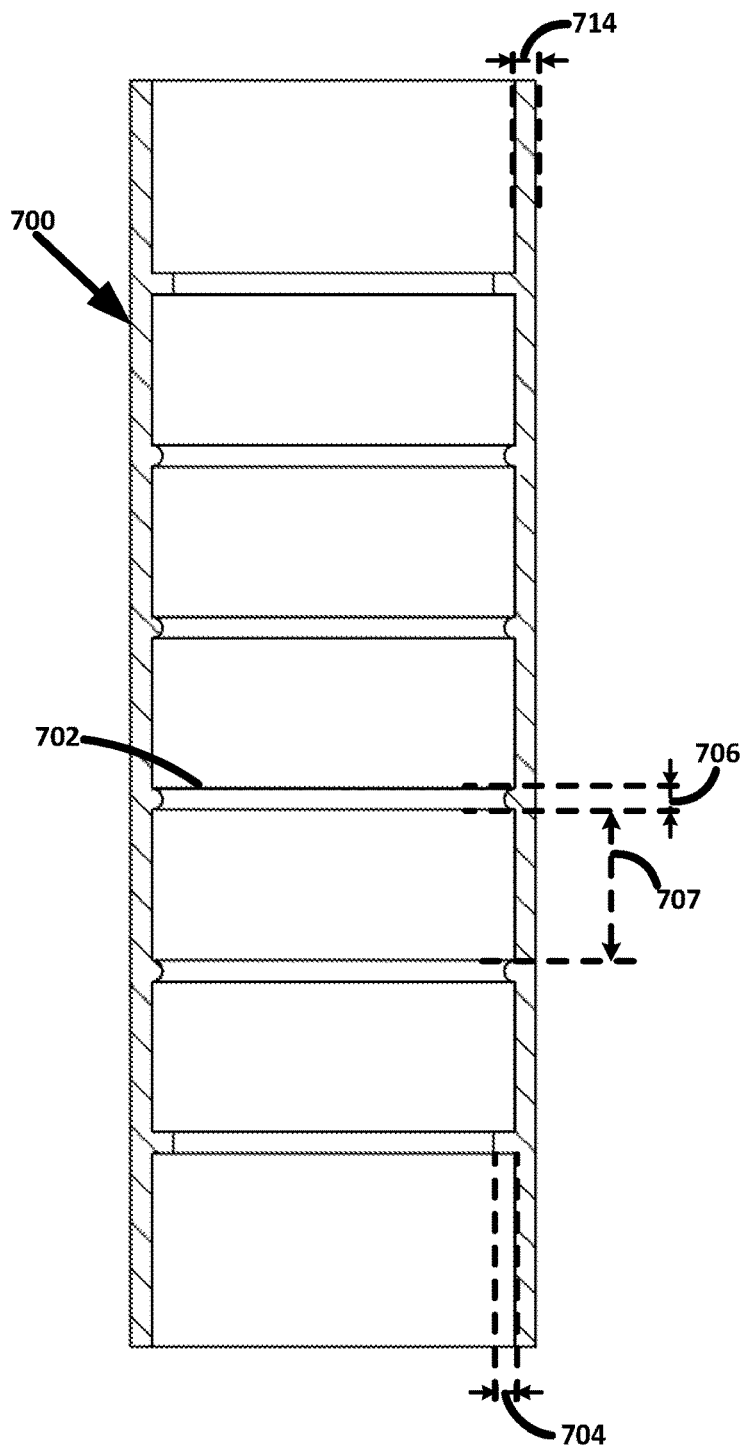
FIG. 7 shows a side view diagram of an embodiment of an inflation balloon of the catheter system 100 in a deflated state.

FIG. 7 shows a side view diagram of an embodiment of an inflation balloon of the catheter system 100 in a deflated state. The inflation balloon 700 may have ridges 702, a ridge height 704, a ridge width 706, a distance between ridges 707, and a thickness of inflation balloon 714. In other embodiments, the inflation balloon of a catheter system 700 may not have all of the elements or features listed and/or may have other elements or features instead of or in addition to those listed. The inflation balloon 700 may be an embodiment of the inflation balloon 140.

The ridges 702 are ridges within the inflation balloon 700 that provide support and prevent sticking of the layers of material to allow for inflation. The ridges 702 may be located along the circumference of the interior of the inflation balloon 700 with ridges 702 spaced every few distance increments along the length of the inflation balloon 700, such that the ridges may be concentric with the shaft.

The ridge height 704 is the height of the ridges 702. The raised ridge height 704 may be of any height, including, for instance, 0.005", 0.006", 0.007", 0.008", 0.009", 0.01", 0.011", 0.012", 0.013", 0.014", 0.04", 0.015", 0.016", 0.017", 0.018", 0.019", 0.02", 0.1 mm, 0.2 mm, 0.3 mm, 0.4 mm, 0.5 mm, 0.6 mm, 0.7 mm, 0.8 mm, 0.9 mm and the like. The raised ridge height 604 may fall into ranges of height, for instance, 0.008"-0.02", 0.009"-0.02", 0.005"-0.02", or 0.1 mm-0.9 mm.

The ridge width 706 is the width of a ridge 702. The ridge width 706 may be, for instance, 0.005", 0.006", 0.007", 0.008", 0.009", 0.01", 0.011", 0.012", 0.013", 0.014", 0.04", 0.015", 0.016", 0.017", 0.018", 0.019", 0.02", 0.1 mm, 0.2 mm, 0.3 mm, 0.4 mm, 0.5 mm, 0.6 mm, 0.7 mm, 0.8 mm, 0.9 mm and the like. The ridge width 604 may fall into ranges of width, for instance, 0.008"-0.02", 0.009"-0.02", 0.005"-0.02", or 0.1 mm-0.9 mm.

The distance between ridges 707 is the distance between ridges 702. The distance between ridges 707 may be, for instance, 0.07", 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.101", 0.102", 0.103", 0.104", 0.105", 0.106", 0.107", 0.108", 0.109", 0.11", 0.11", 0.112", 0.113", 0.114", 0.115", 0.116", 0.117", 0.118", 0.119", 0.12", 0.13", 0.14", 0.15", 0.16", 0.17", 0.18", 0.19", 0.2", 0.3", 0.4", 0.5", 0.6", 0.7", or 0.8". The distance between ridges 707 may be within any range of distances, for instance, 0.08"-0.5", 0.07"-0.5", 0.08"-0.1", 0.07"-0.1", 0.07"-0.2", 0.095"-0.2", 0.1"-0.2", 0.105"-0.2", 0.1"-0.12", 0.09"-0.12", or 0.099"-0.111".

The thickness of inflation balloon 714 is the thickness of the membrane that forms the drug delivery balloon 600. The thickness of drug delivery balloon 614 may be, for instance 0.007", 0.008", 0.009", 0.01", 0.011", 0.012", 0.013", 0.014", 0.015", 0.2 mm, 0.21 mm, 0.22 mm, 0.23 mm, 0.24 mm, 0.25 mm, 0.254 m, 26 mm, 0.27 mm, and the like. The thickness of inflation balloon 714 may be, for instance, in the ranges 0.005"-0.015", 0.009"-0.011", 0.008"-0.012", 0.2 mm-0.3 mm, and the like.

Figure 8:
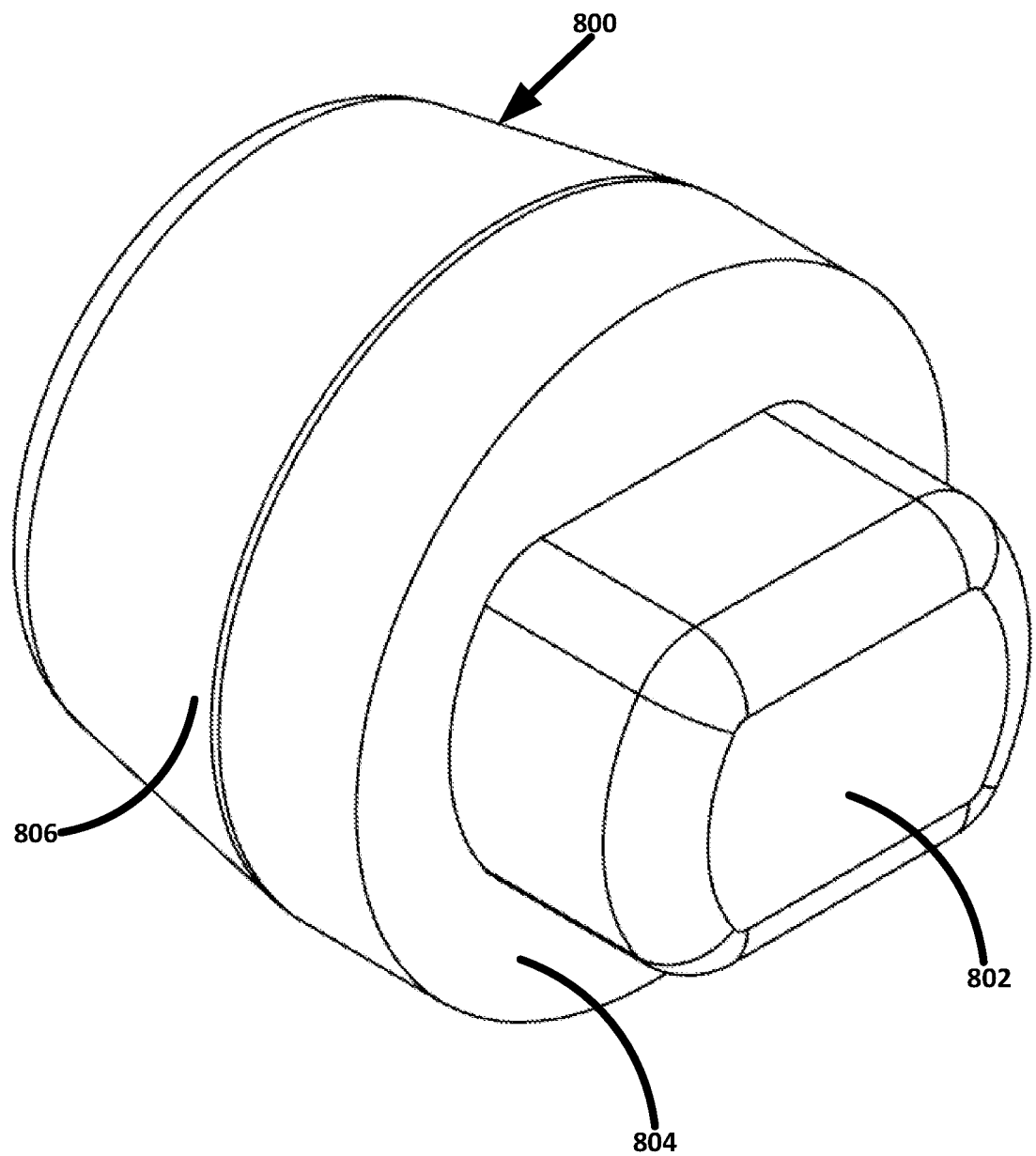
FIG. 8 shows a perspective view of an end cap of the catheter system 100.

FIG. 8 shows a perspective view of an end cap of the catheter system 100. The end cap 800 has a plug 802, a flat interface 804, and an angled exterior 806. In other embodiments, the end cap of a catheter system 800 may not have all of the elements or features listed and/or may have other elements or features instead of or in addition to those listed. The end cap 800 may be an embodiment of end cap 134.

The plug 802 is a plug, which penetrates and seals the bladder fluid lumen by pressure fit. The plug 802 may conform well enough to prevent flow of bladder drainage to the lumens. The end cap 800 may have additional plugs for the smaller drug delivery and inflation lumens or may simply abut them and rely on the snug fit of the plug to prevent slippage such that the distal edge of the shaft is flush with the end cap 800 and no fluids may enter from around the edges of the end cap 800. The plug 802 may have any depth, for instance, 0.05", 0.051", 0.052", 0.053", 0.054", 0.055", 0.056", 0.057", 0.058", 0.059", 0.06", 0.061", 0.062", 0.063", 0.064", 0.065", 0.066", 0.067", 0.068", 0.069", or 0.07". The plug 802 may have a depth within a range of depths, including 0.05"-0.07", 0.055"-0.065", or 0.059"-0.061".

The flat interface 804 is the flat area around the plug that creates a flush fit with the end of the shaft, preventing fluids in the bladder from entering the drug delivery and inflation lumens.

The angled exterior 806 is an exterior element of the end cap 800 that will be the first element to enter the body when using the catheter. Because the angled exterior 806 is the first element introduced, the angle provides a lead-in edge for easier and more comfortable insertion.

Figure 9:
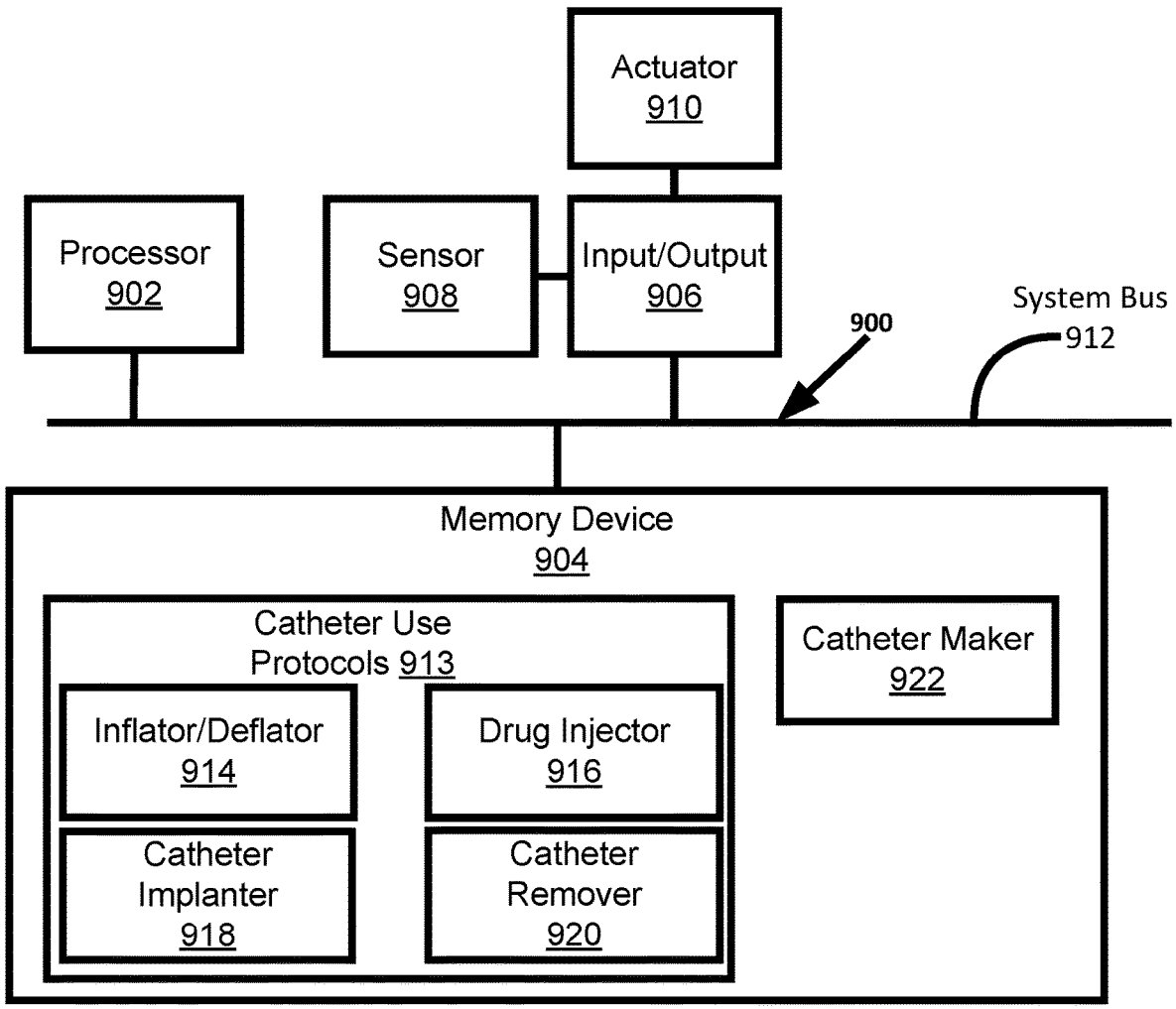
FIG. 9 shows a block diagram of an embodiment of a computer for use with the catheter system 100.

FIG. 9 shows a block diagram of an embodiment of a computer for use with the catheter system 100. The computer 900 may include a processor 902, a non-transitory memory device 904, an input output 906, a sensor 908, an actuator 910, a system bus 912, catheter use protocols 913, a balloon inflator/deflator 914, a drug injector 916, a catheter inserter/remover 918, and a catheter maker 920. In other embodiments, the computer for use with a catheter system 900 may not have all of the elements or features listed and/or may have other elements or features instead of or in addition to those listed. In an embodiment, the computer is a non-transitory computing medium.

The processor 902 is a device used to process commands stored in the memory device 904. The processor 902 may include any one of, some of, any combination of, or all of multiple parallel processors, a single processor, a system of processors having one or more central processors, a logic circuit, a hardwire and/or one or more specialized processors dedicated to specific tasks.

The non-transitory memory device 904 may include, for example, any one of, some of, any combination of, or all of a long term storage system, such as a hard drive; a short term storage system, such as a random access memory. The memory may include, for example, read-only memory ("ROM"), random access memory ("RAM"), erasable programmable read only memory ("EPROM"), electrically erasable programmable read only access memory ("EEPROM"), a dedicated state logic circuit, flash, non-volatile random access memory ("NVRAM"). In an embodiment, the memory device 904 may include a removable storage system such as a disk drive, floppy drive or a removable drive; and/or flash memory. The memory device 904 may include one or more machine-readable media that may store a variety of different types of information. The term machine-readable media may be used to refer to any non-transient medium capable of carrying information that is readable by a machine. One example of a machine-readable medium is a computer-readable medium. The memory device 904 may also store variables, intermediates, results, constants, and the like necessary to execute functions. For instance, the memory device 904 may store commands to be executed by the processor 902 in order to perform functions.

Functions to be executed by the processor 902 which may be stored in the memory 904 may include, for instance, catheter use protocols 913, and a catheter maker 922.

The catheter use protocols 913 are protocols for the regular operation and use of the catheter. The catheter use protocols 913 may include the balloon inflator/deflator 914, a drug injector 916, a catheter inserter 918, and a catheter remover 920.

The balloon inflator/deflator 914 is an executable module which, when executed by the processor 902, causes an inflation balloon to inflate or deflate by triggering the actuator 910 to add or remove inflation fluid. The sensor 908 may determine the pressure of the balloon, and the balloon inflator/deflator 914 may determine the extent to which the balloon must be deflated in response. The inflator/deflator 914 may execute steps of the embodiment of the method for using a catheter shown in FIG. 10.

The drug injector 916 is an executable module which, when executed by the processor 902, causes injection of drug fluids at a particular rate by triggering the actuator 910 to add or remove inflation fluid. The sensor 908 may determine the drug levels present in the system, and the drug injector 916 may determine the extent to which an actuator 910 must inject more drug fluid. The drug injector 916 may execute steps of the embodiment of the method for using a catheter shown in FIG. 10.

The catheter inserter/remover 918 is an executable module which, when executed by the processor 902, causes a catheter to be inserted in a patient's bladder or removed from a patient's bladder by triggering the actuator 910 to push the catheter into a body or remove the catheter from the body. The catheter inserter 918 may execute steps of the embodiment of the method for using a catheter shown in FIG. 10.

The catheter maker 920 is an executable module which, when executed by the processor 902, causes a catheter to be made by the actuator 910 with the aid of the sensor 908. The catheter maker 920 may execute steps in the methods for making catheters, including, for instance, the embodiment of a methods for making a catheter system shown in FIGS. 11, 12, 13, 14, 15, and 16.

The input/output device 906 is a device capable of communicatively coupling useful components to a computerized or hardwired system. The input/output device 906 may be one unit or may represent separate input and output devices. The output element of the input/output device 906 may include any one of, some of, any combination of, or all of a sensor 908, an actuator 910, display system, a speaker system, a connection or interface system to a sound system, an interface system to peripheral devices and/or a connection and/or a interface system to a computer system, intranet, and/or internet, and the like. The device output system may include a monitor and/or other output device.

The input element of the input/output device 902 may include connections and hardware for any of, some of, any combination of, or all of a sensor 908 actuator 910, a transceiver, a keyboard system, an interface to receive secured data, a mouse system, a track ball system, a track pad system, buttons on a handheld system, a scanner system, a microphone system, a touchpad system, and/or a connection and/or interface system to a computer system, intranet, and/or internet (e.g., IrDA, USB), and the like.

The sensor 908 is a device made to detect and measure physical characteristics and output a data stream. The sensor may be used to detect any of the quantities described in the embodiment of a chemical profile in FIG. 6. The sensor may also be used to detect a state in order to carry out the steps of the embodiments of methods of FIGS. 10, 11, 12, 13, 14, 15, and 16. For instance, the computer sensor 908 may be used to detect the presence of drug fluids, the completion of steps in the methods for making catheters and the like.

The actuator 910 is a device for generating a physical change. The actuator 3010 may take actions based on instructions received from the processor 3002, and may perform any of the steps in the embodiments of methods of FIGS. 10,11,12, 13, 14, 15, and 16.

The system communication bus 912 is a medium used to communicatively couple elements of the computer 900. The communication bus 912 may couple any, all of, or some of the processor 902, memory device 904, input/output device, 906, sensor 908, actuator 910, and any other components which may be coupled physically or communicatively to the computer 900.

Figure 10:
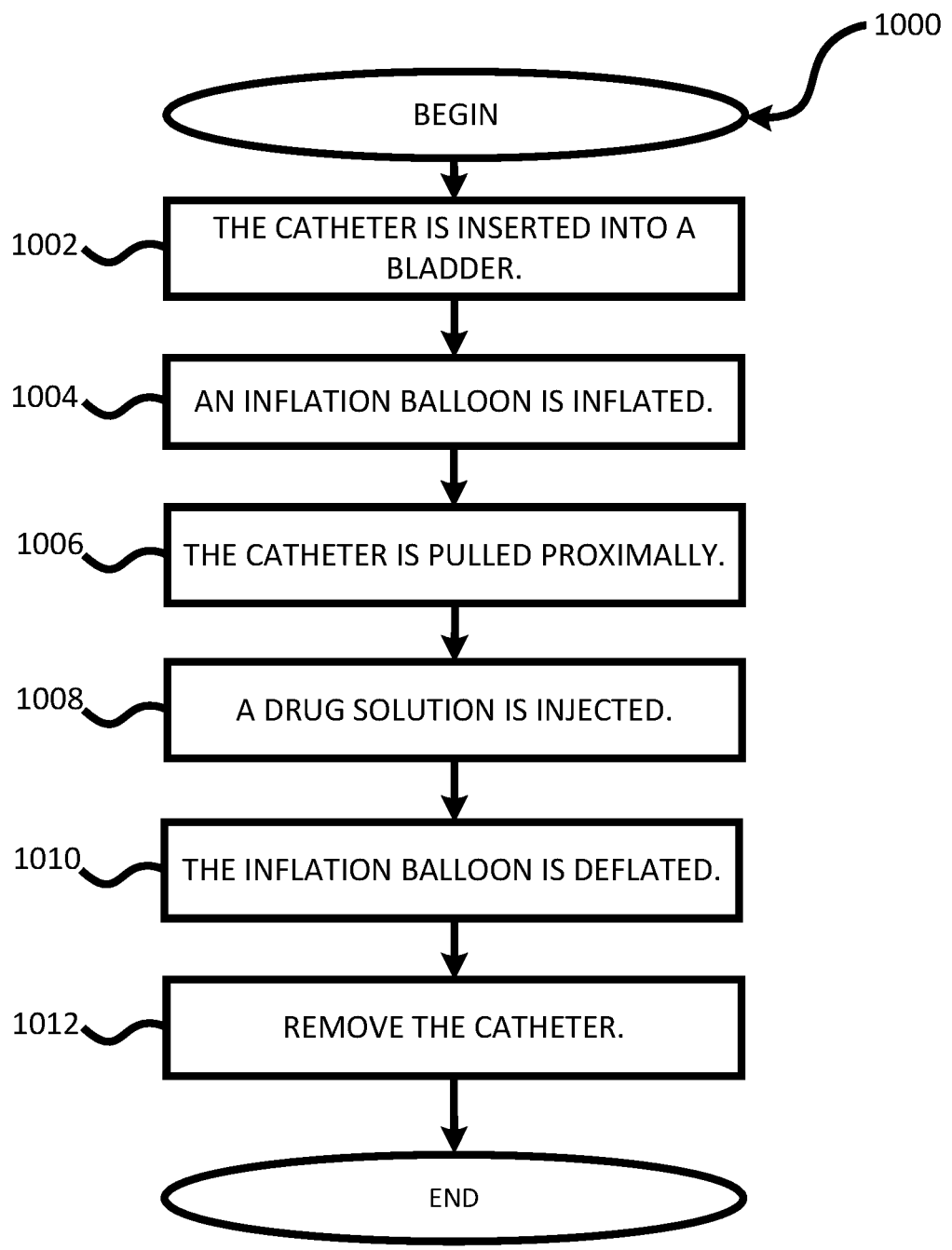
FIG. 10 shows a flowchart of an embodiment of a method for using the catheter system 100

FIG. 10 shows a flowchart of an embodiment of a method for using the catheter system 100. The method 1000 may include steps of insert the catheter 1002, inflate the inflation balloon 1004, pull the assembly 1006, inject drug solution 1008, deflate the inflation balloon 1010, and remove the catheter 1012.

In step 1002, the catheter 100 is inserted into a bladder 105. The catheter 100 may be inserted through the urethra, until the inflation balloon 140 is inside the bladder. When in the bladder, the catheter may be considered indwelling. A health care specialist typically inserts the catheter 100. The catheter is pushed through the urethra with the distal end of the catheter system 100 entering the urethra first until the inflation balloon is in the bladder.

In step 1004, an inflation balloon is inflated. The inflation balloon 140 may be inflated by a syringe, by a pressure generating device, or a computer aided pump via the inflation input.

In step 1006, the catheter 100 is pulled proximally in order to assure a tight fit with the balloon in the bladder.

In step 1008, a drug solution is injected. The drug may be injected using a syringe in the drug solution input 110, or alternatively, a computerized pump may regulate a consistent flow of drug fluids to the catheter system via the drug solution input 110. The drug solution injected may be different from the inflation fluid injected in step 1004. For instance, the drug fluid injected by a care provider may enter In step 1010, the inflation balloon 130 is deflated to prepare the catheter 100 for removal. A syringe or other vacuum generating device may be used to deflate the inflation balloon 140.

In step 1012, the catheter 100 is removed through the urethra.

In an embodiment, each of the steps of the method 1000 shown in FIG. 10 is a distinct step. In another embodiment, although depicted as distinct steps in FIG. 10, steps 1002-1012 may not be distinct steps. In other embodiments, the method shown in FIG. 10 may not have all of the above steps and/or may have other steps in addition to or instead of those listed above. The steps of the method shown in FIG. 10 may be performed in another order. Subsets of the steps listed above as part of the method shown in FIG. 10 may be used to form the subsets' own methods.

Figure 11:
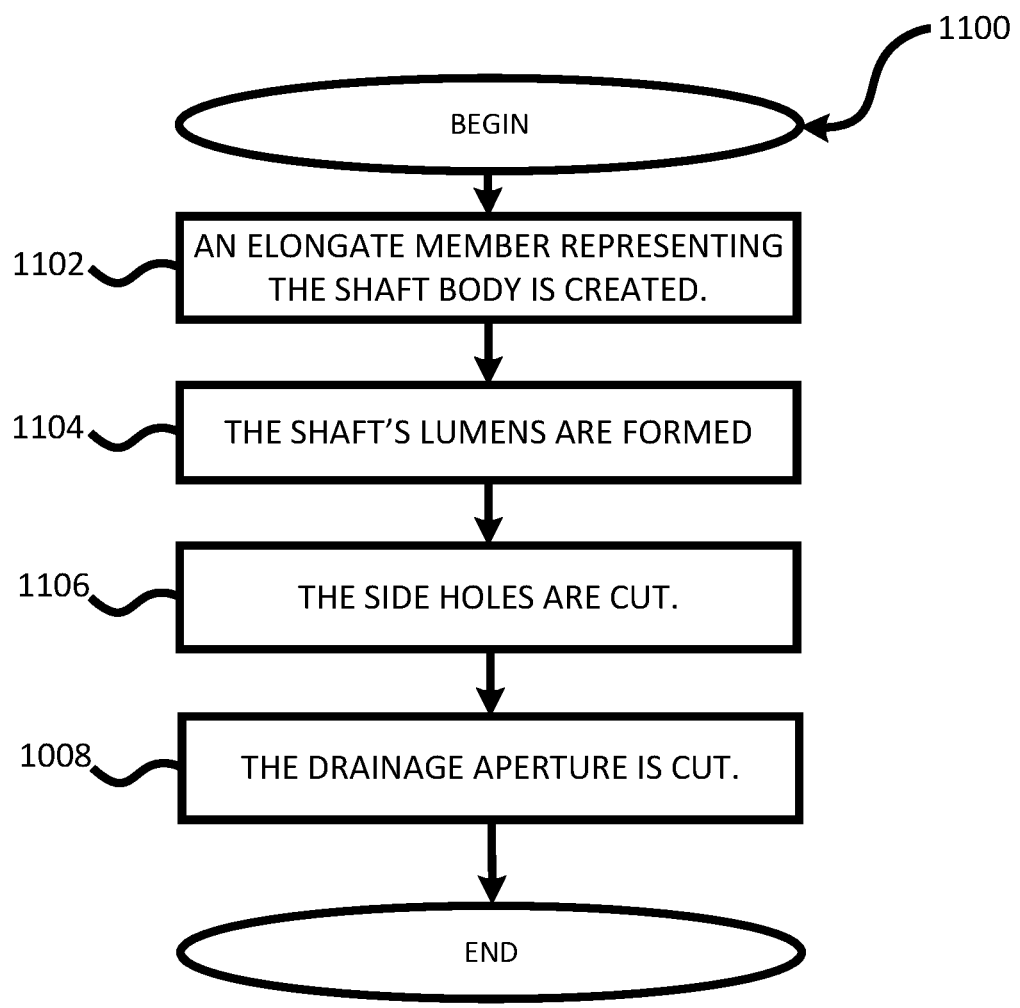
FIG. 11 shows a flowchart of an embodiment of a method for making a shaft 120 of the catheter system 100.

FIG. 11 shows a flowchart of an embodiment of a method for making a shaft 120 of the catheter system 100. The method 1100 may include steps of creating an elongate member 1102, extruding the lumens from the elongate member 1104, cutting the side holes 1106, and cutting the drainage aperture 1108.

In step 1102, an elongate member representing the unrefined shaft body 120 is created. The elongate member may be created by extrusion from a larger piece. The larger piece may be a blending of two-part silicone gumstock on a two roll mill to create medical grade silicone. The medical grade silicone may be formed into strips and fed into an extruder.

In step 1104, the shaft's lumens are formed. A pin and die tool may be created for each Foley catheter FR size that is required. The die may be created to form the cross section show in FIG. 5, the cross section including, for instance, the diameter of the drug delivery lumen 502, the diameter of an inflation lumen 504, a narrowest internal diameter of an inflation lumen 506, and a widest diameter width of a bladder fluid lumen 508. A variable speed screw feed may apply and maintain a determined pressure on the pin and die as the elongate member (representing the unrefined shaft body) may be extruded to simultaneously form the shaft body 120, the drug delivery lumen 124, and the bladder fluid lumen 126. A laser micrometer may monitor the outside diameter of the elongate member.

In step 1106, the side holes are cut. The drug fluid side hole 128 may be cut or skived on the opposite side of the shaft 120 from the inflation side hole 130. The respective drug fluid side hole 128 and the inflation side hole 130 may be cut deeply enough to reach the innermost surface of the respective interiors of each of the drug delivery lumen 122 and the inflation lumen 124.

In step 1108, the drainage aperture 132 is cut. The drainage aperture 132 may be cut or skived all the way through the shaft, through the bladder fluid lumen 126. The cut should not puncture the drug delivery lumen 122 and the inflation lumen 124. The resultant refined shaft body may be cured in a radiant heat oven.

In an embodiment, each of the steps of the method 1100 shown in FIG. 11 is a distinct step. In another embodiment, although depicted as distinct steps in FIG. 11, steps 1102-1108 may not be distinct steps. In other embodiments, the method shown in FIG. 11 may not have all of the above steps and/or may have other steps in addition to or instead of those listed above. The steps of the method shown in FIG. 11 may be performed in another order. Subsets of the steps listed above as part of the method shown in FIG. 11 may be used to form the subsets' own methods.

Figure 12:
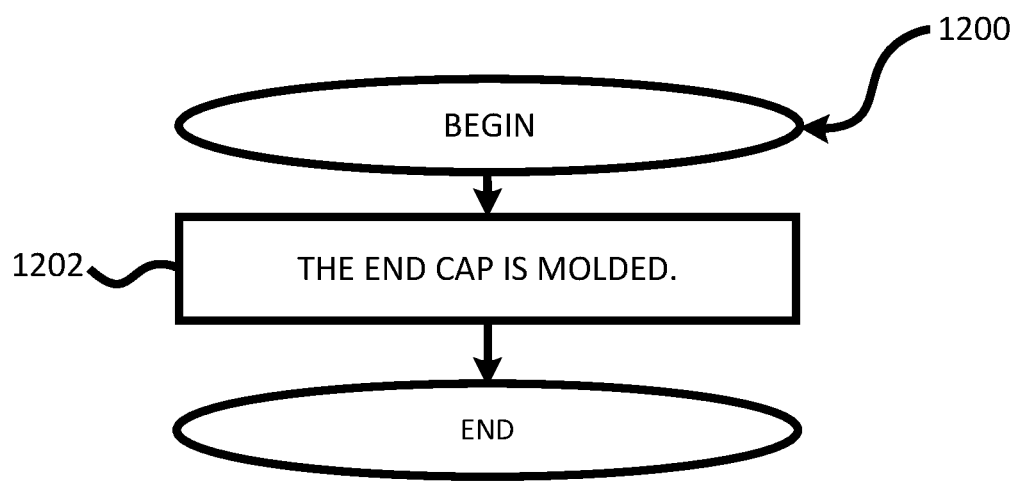
FIG. 12 shows a flowchart of an embodiment of a method for making an end cap 134 of the catheter system 100.

FIG. 12 shows a flowchart of an embodiment of a method for making an end cap 134 of the catheter system 100. The method 1200 may include a step of molding the end cap 1202.

In step 1202, the end cap is molded to include the plug 802, the flat interface 804, and the angled exterior 806. In an embodiment, the end cap 134 may be formed on the distal end of the shaft body 120 by placing the shaft body 120 into the end cap tool to mold the end cap 134 directly to the shaft body 120. In an embodiment, the inflation balloon 140 and the drug delivery balloon 150 are made before the end cap 134 is made.

In an embodiment, the step of the method 1200 shown in FIG. 12, although depicted as a single step in FIG. 12, step 1202 may not be a distinct step. In other embodiments, the method shown in FIG. 12 may have other steps in addition to or instead of the step listed above. The step of the method shown in FIG. 12 may be performed in another order with multiple moldings. Subsets of the step listed above as part of the method shown in FIG. 12 may be used to form the subsets' own methods.

Figure 13:
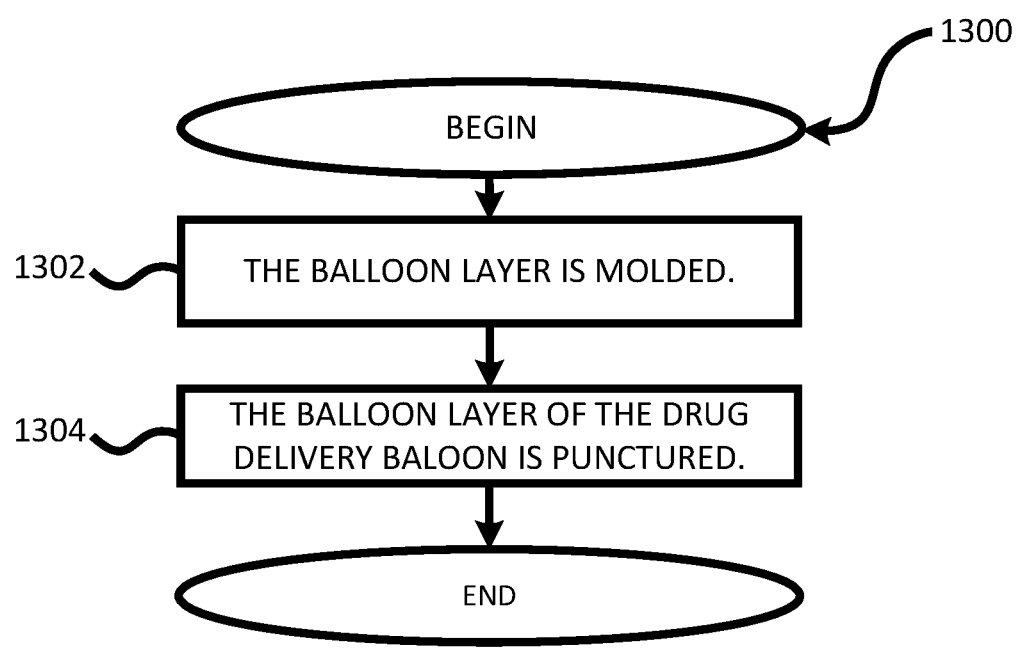
FIG. 13 shows a flowchart of an embodiment of a method for making a drug delivery balloon 150 of the catheter system 100.

FIG. 13 shows a flowchart of an embodiment of a method for making a drug delivery balloon 150 of the catheter system 100. The method 1300 may include steps of molding the balloon layer 1302 and optionally puncturing the balloon layer 1304.

In step 1302, the balloon layer is molded. The balloon layer of the drug delivery balloon 150 is molded to be cylindrical in shape with a hollow inside. The ridges 602 are also molded into balloon. In one embodiment, the holes 608 are molded into the balloon layer. In this embodiment, the drug delivery balloon 150 may be considered injection molded. In an alternative embodiment, the holes 608 may be punctured in a separate step. In this alternative embodiment, the drug delivery balloon 150 may be injection molded or blow molded. The drug delivery balloon 150 may be overmolded in place or molded separately and assembled as a secondary operation.

In step 1304, the balloon layer of the drug delivery balloon 150 is punctured to create the holes 608, only if the holes are not created by molding in step 1302. The holes 608 may be punched, perforated, or skived away from the balloon layer using a Murphy Eye Punch (+/−0.020").

In an embodiment, each of the steps of the method 1300 shown in FIG. 13 is a distinct step. In another embodiment, although depicted as distinct steps in FIG. 13, steps 1302-1304 may not be distinct steps. In other embodiments, the method shown in FIG. 13 may not have all of the above steps and/or may have other steps in addition to or instead of those listed above. The steps of the method shown in FIG. 13 may be performed in another order. Subsets of the steps listed above as part of the method shown in FIG. 13 may be used to form the subsets' own methods.

Figure 14:
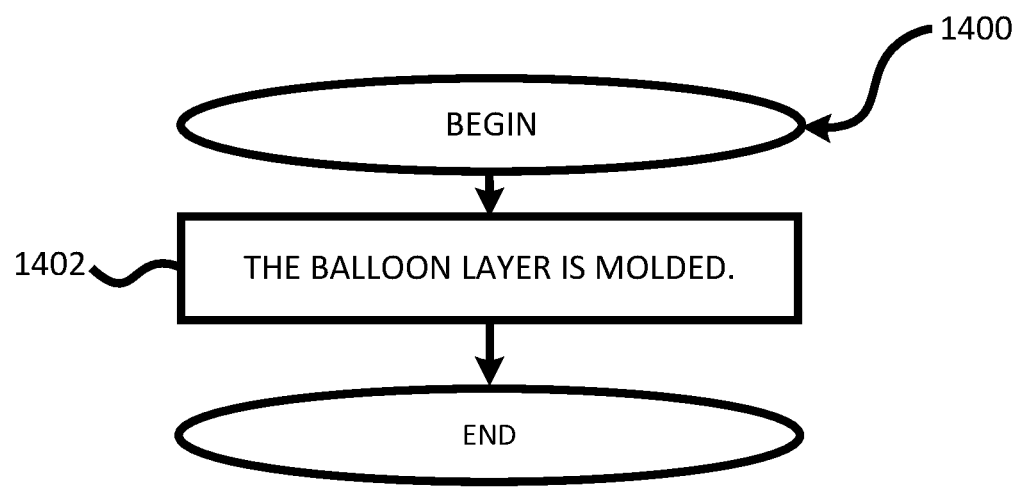
FIG. 14 shows a flowchart of an embodiment of a method for making an inflation balloon 140 of the catheter system 100.

FIG. 14 shows a flowchart of an embodiment of a method for making an inflation balloon 140 of the catheter system 100. The method 1400 may include a step of molding the balloon layer 1402.

In step 1402, the balloon layer is molded. The balloon layer of the inflation balloon 140 is molded to be cylindrical in shape with a hollow inside. The ridges 702 are also molded into balloon layer. The balloon layer may be molded using injection molding or blow molding methods. The inflation balloon 140 may be overmolded in place or molded separately and assembled separately as a secondary operation. In an embodiment, the inflation balloon 140 is made before the drug delivery balloon 150.

In an embodiment, the step of the method 1400 shown in FIG. 14, although depicted as a single step in FIG. 14, step 1402 may not be a distinct step. In other embodiments, the method shown in FIG. 14 may have other steps in addition to or instead of the step listed above. The step of the method shown in FIG. 14 may be performed in another order with multiple moldings. Subsets of the step listed above as part of the method shown in FIG. 14 may be used to form the subsets' own methods.

Figure 15:
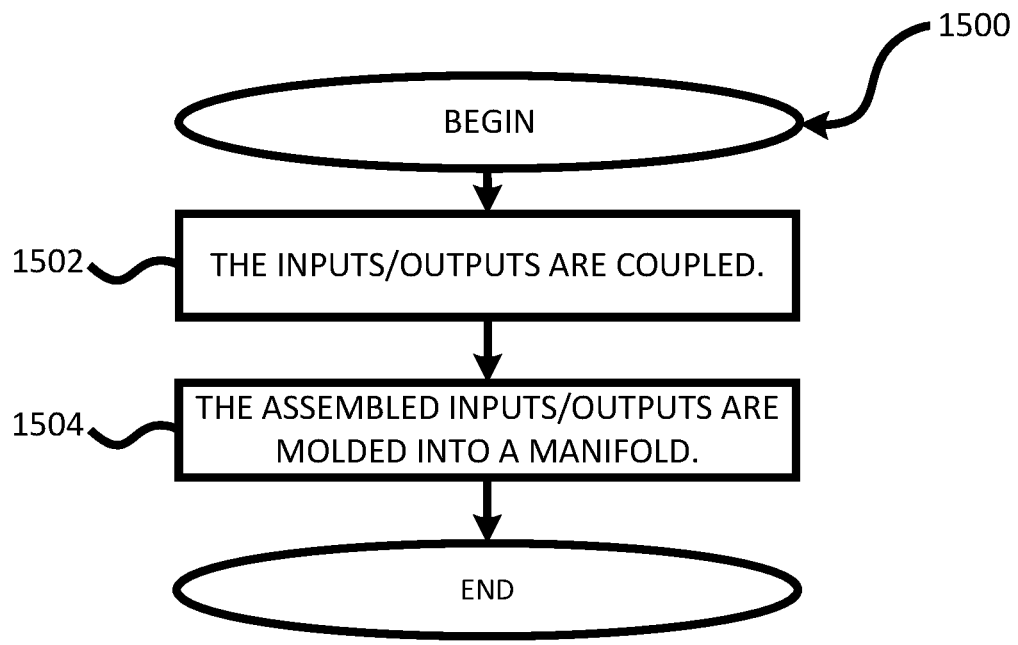
FIG. 15 shows a flowchart of an embodiment of a method for making the input manifold 102 of the catheter system 100.

FIG. 15 shows a flowchart of an embodiment of a method for making the input manifold 102 of the catheter system 100. The method 1500 may include steps of coupling the input/outputs 1502 and molding the manifold about the inputs 1504.

In step 1502, the inputs/outputs, including the drug fluid input 112, the inflation fluid input 110, and the bladder drainage output 114 are coupled. The inputs may be coupled in a single plane. In an embodiment, the input/outputs are coupled by the manifold molding of step 1504. In another embodiment, the input/outputs may remain separate and uncoupled. In another embodiment, an existing Foley trifurcation catheter with three inputs/outputs may be used. The inputs may be existing Luer-Lok fittings.

In step 1504, the assembled inputs/outputs are molded into a manifold. The manifold is molded with extensions from the input open so as to be in fluid communication with the lumens of the shaft 120 when the shaft 120 is coupled. The mold may be a one or more cavity steel mold for each FR Foley catheter size.

In an embodiment, each of the steps of the method 1500 shown in FIG. 15 is a distinct step. In another embodiment, although depicted as distinct steps in FIG. 15, steps 1502-1504 may not be distinct steps. In other embodiments, the method shown in FIG. 15 may not have all of the above steps and/or may have other steps in addition to or instead of those listed above. The steps of the method shown in FIG. 15 may be performed in another order. Subsets of the steps listed above as part of the method shown in FIG. 15 may be used to form the subsets' own methods.

Figure 16:
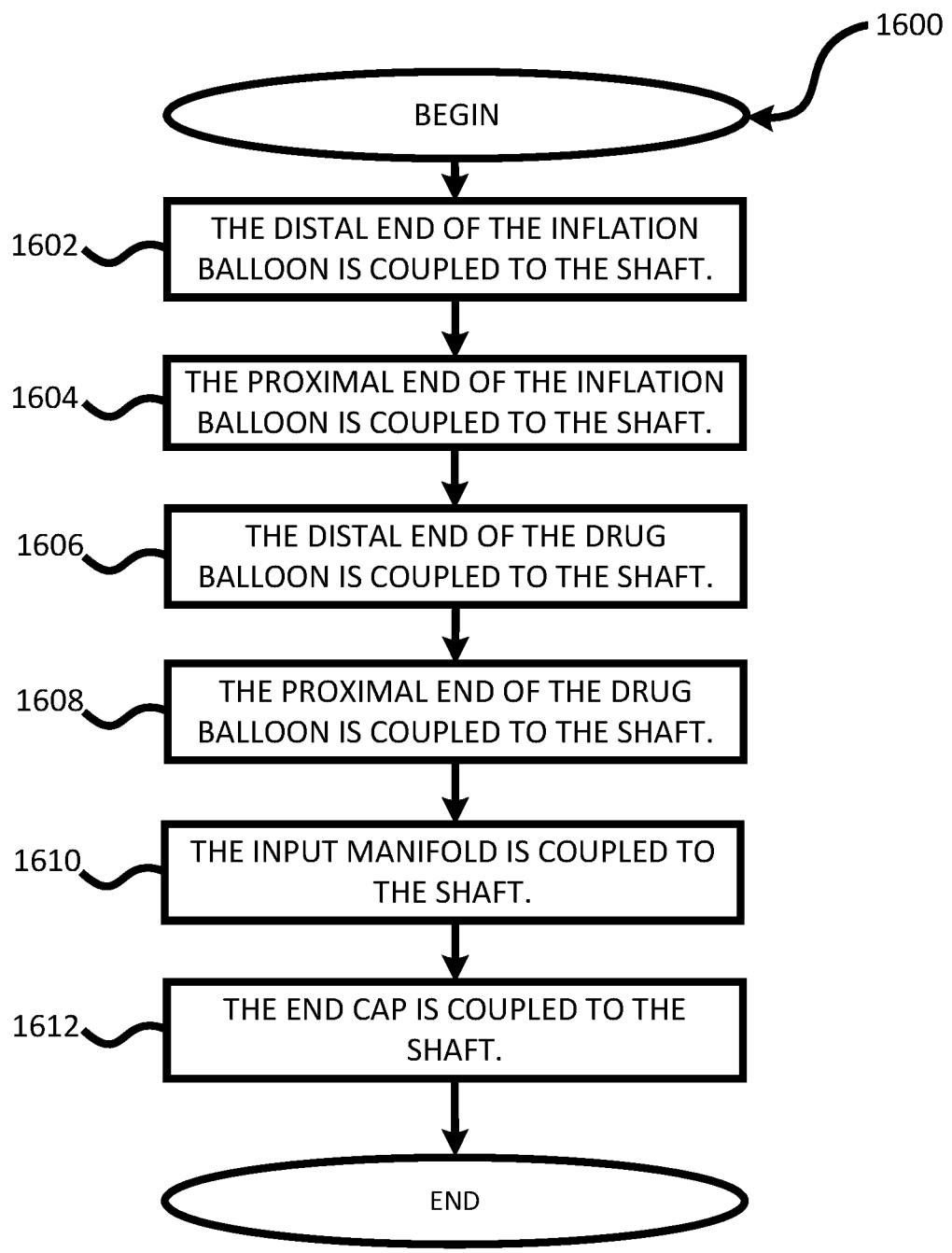
FIG. 16 shows a flowchart of an embodiment of a method for assembling the catheter system 100.

FIG. 16 shows a flowchart of an embodiment of a method for assembling the catheter system. The method 1600 may include steps of couple distal end of the inflation balloon to the shaft 1602, couple the proximal end of the inflation balloon to the shaft 1604, couple the distal end of the drug delivery balloon to the shaft 1606, couple the distal end of the drug delivery balloon 1608, couple the input manifold to the shaft 1610, couple the end cap to the shaft 1612.

In step 1602, the distal end of the inflation balloon 140 is coupled to the shaft 120. The coupling may occur at a distal inflation balloon coupling site 412. The distal balloon coupling site 412 may be between the distal end of the shaft 120 and the inflation side hole 130. The coupling may be accomplished by heat sealing the distal edge of the inflation balloon 140 to the shaft 120, polymer coating on top of the inflation balloon 140 and the shaft 120, or by applying adhesive to the distal edge of the inflation balloon 140 or shaft 120 and compressing the inflation balloon 140 and shaft 120 together.

In step 1604, the proximal end of the inflation balloon 140 is coupled to the shaft 120. The coupling may occur at the proximal inflation balloon coupling site 414. The proximal inflation balloon coupling site 414 may be between the drug fluid side hole 128 and the proximal end of the shaft 120. The coupling may be accomplished by heat sealing the proximal edge of the inflation balloon 140 to the shaft 120, polymer coating on top of the inflation balloon and the shaft, or by applying adhesive to the proximal edge of the inflation balloon 140 or shaft 120 and compressing the inflation balloon 140 and shaft 120 together. The proximal inflation balloon coupling site 414 may be a distance from the drug fluid side hole 128 when the inflation balloon 140 is inflated of, for instance, 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, or within a range of 0.005"-0.02", 0.011"-0.0147", 0.01"-0.05", 0.01"-0.06", 0.02"-0.04", 0.02"-0.05", 0.03"-0.044", 0.04"-0.053", 0.02"-0.06", 0.02"-0.053", 0.2 mm-0.4 mm, 0.1 mm-0.5 mm, 0.27 mm-0.44 mm, 0.5 mm-0.8 mm, 0.5 mm-1.5 mm, 0.5 mm-1 mm, 0.7 mm-1 mm, 0.7 mm-1.5 mm, or 0.7 mm-1.6 mm.

In step 1606, the distal end of the drug delivery balloon 150 is coupled to at least one of the shaft 120 or the inflation balloon 140. The coupling may occur at the distal drug balloon coupling site 410. The distal drug balloon coupling site 410 may be between the drug fluid side hole 128 and the inflation side hole 130 or may be between the inflation side hole 130 and the drainage aperture 132. The coupling may be accomplished by heat sealing the proximal edge of the drug delivery balloon 150 to the shaft 120 or inflation balloon 140, polymer coating on top of the drug delivery balloon 150 and the shaft 120, or by applying adhesive to the proximal edge of the drug delivery balloon 150 or shaft 120 and compressing the drug delivery balloon 150 and shaft 120.

In Step 1608, the proximal end of the drug delivery balloon 150 is coupled to the shaft 120. The coupling may occur at the proximal drug balloon coupling site 416. The coupling may be accomplished by heat sealing the proximal edge of the drug delivery balloon 150 to the shaft 120, polymer coating on top of the drug delivery balloon 150 and either the shaft 120, or by applying adhesive to the proximal edge of the drug delivery balloon 150 or the shaft 120 and compressing the drug delivery balloon 150 and the shaft 120.

In step 1610, the input manifold 102 is coupled to the proximal end of the shaft 120. The input manifold 102 should be situated in order to allow fluid communication between the input/outputs and the corresponding lumens in the shaft 120. When the input manifold 102 is coupled to the shaft, the drug fluid input 112 should be open to and in fluid communication with the drug delivery lumen 122, the inflation fluid input 110 should be open to and in fluid communication with the inflation lumen 124, and the bladder drainage output 114 should be open to and in fluid communication with the bladder fluid lumen 126. The input manifold 102 may be coupled to the shaft 120 using adhesive, a heat seal or by polymer coating the input manifold 102 with the shaft 120.

In step 1612, the end cap 132 is coupled to the shaft 120. The end cap 132 may be coupled to the shaft 120 using adhesive, heat seal or by polymer coating the end cap 132 to the shaft 120. In an alternative embodiment, the end cap 134 is molded directly onto the shaft body 120 using an end cap tool.

In another alternative embodiment, an existing shaft with three lumens may be used. In this alternative embodiment, the inflation balloon 140 may be overmolded or coupled to the shaft 120 and the drug delivery balloon 150 coupled to the exterior of the inflation balloon 150 and/or the shaft 120.

In still another alternative embodiment, a shaft 120 with three lumens and an existing inflation balloon 140 may be the starting point. In this instance, the method may include steps of coupling or overmolding the drug delivery balloon 150 to the exterior of the shaft 120 and/or the inflation balloon 140 such that the space between the interior of the drug delivery balloon 150 and the inflation balloon is in fluid communication with the drug delivery lumen 122.

In an embodiment, each of the steps of the method 1600 shown in FIG. 16 is a distinct step. In another embodiment, although depicted as distinct steps in FIG. 16, steps 1602-1612 may not be distinct steps. In other embodiments, the method shown in FIG. 16 may not have all of the above steps and/or may have other steps in addition to or instead of those listed above. The steps of the method shown in FIG. 16 may be performed in another order. Subsets of the steps listed above as part of the method shown in FIG. 16 may be used to form the subsets' own methods.

Figure 17:
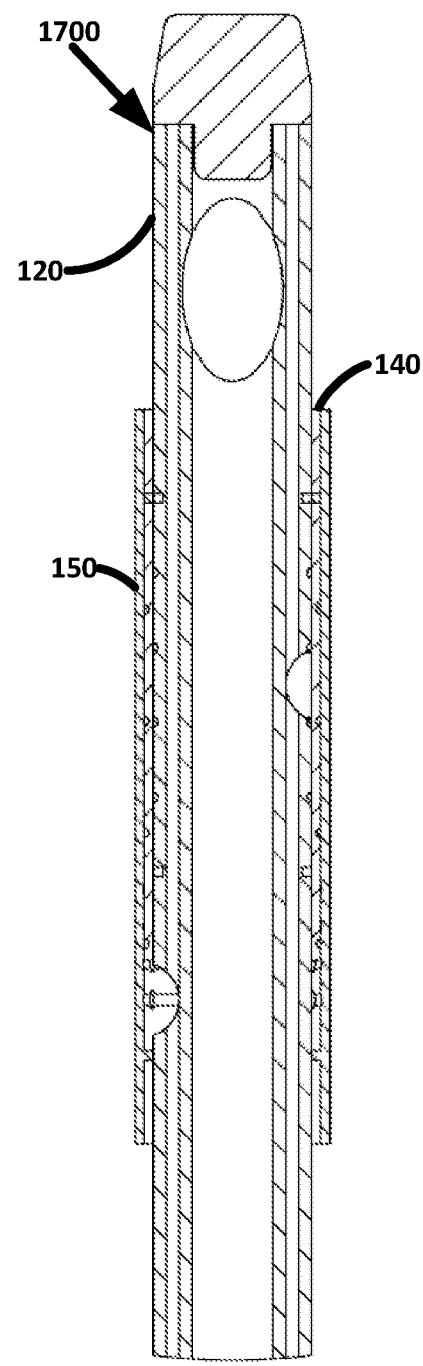
FIG. 17 shows an image of an embodiment of a distal portion of a catheter system 100 with a deflated inflation balloon 140.

FIG. 17 shows an image of an embodiment of a distal portion of a catheter system 100 with a deflated inflation balloon 140. The catheter system 1700 has a shaft 120, an inflation balloon 140, and a drug delivery balloon 150. In other embodiments, the catheter system 1700 may not have all of the elements or features listed and/or may have other elements or features instead of or in addition to those listed. The catheter system 1700 may be an embodiment of the catheter system 100.

Figure 18:
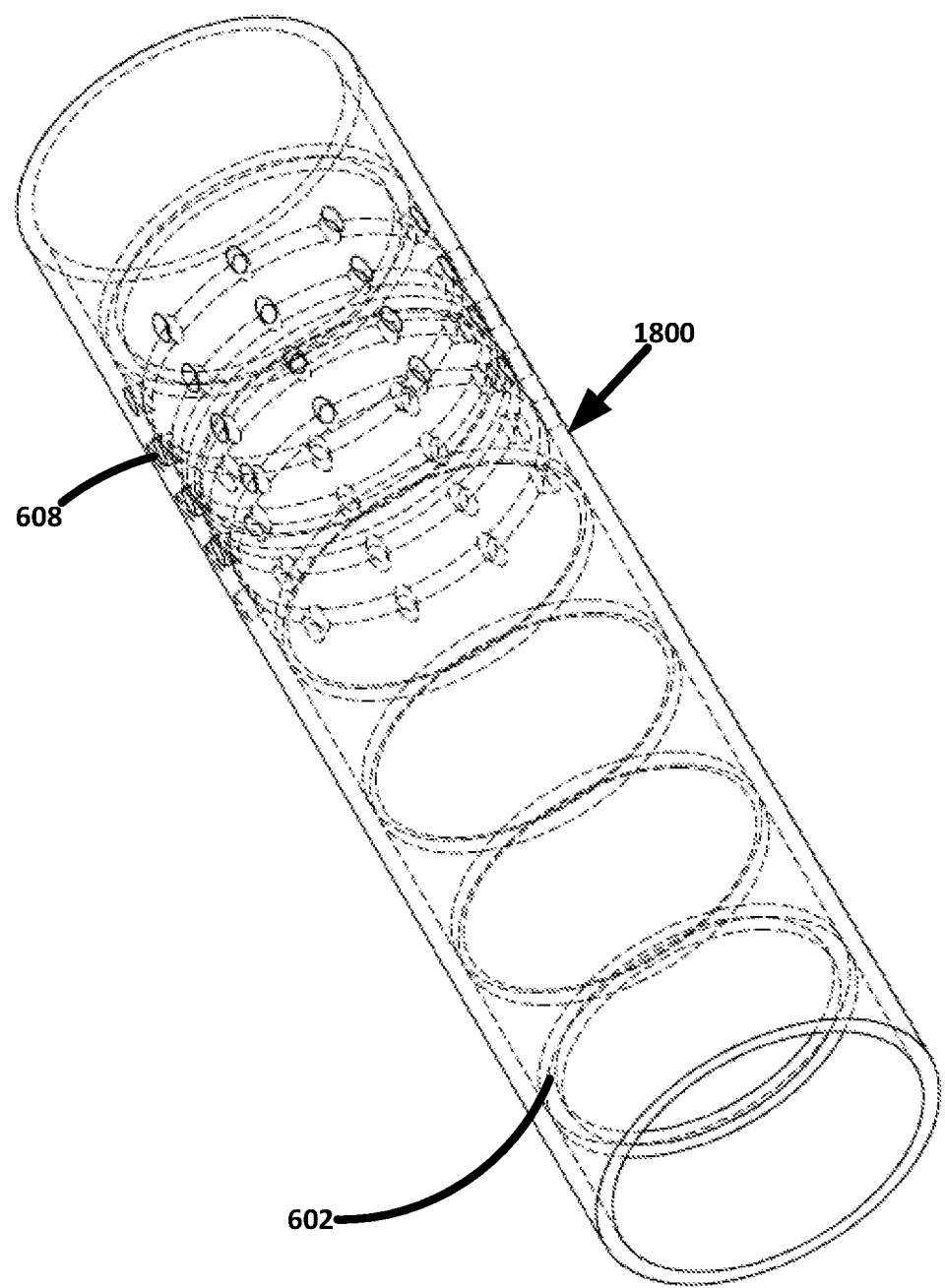
FIG. 18 shows a perspective view of an embodiment of a drug delivery balloon 150 of the catheter system 100.

FIG. 18 shows a perspective view of an embodiment of a drug delivery balloon 150 of the catheter system 100. The drug delivery balloon 1800 has ridges 602 and holes 608. In other embodiments, the drug delivery balloon 1800 may not have all of the elements or features listed and/or may have other elements or features instead of or in addition to those listed. The drug delivery balloon 1800 may be an embodiment of the drug delivery balloon 150.

Figure 19:
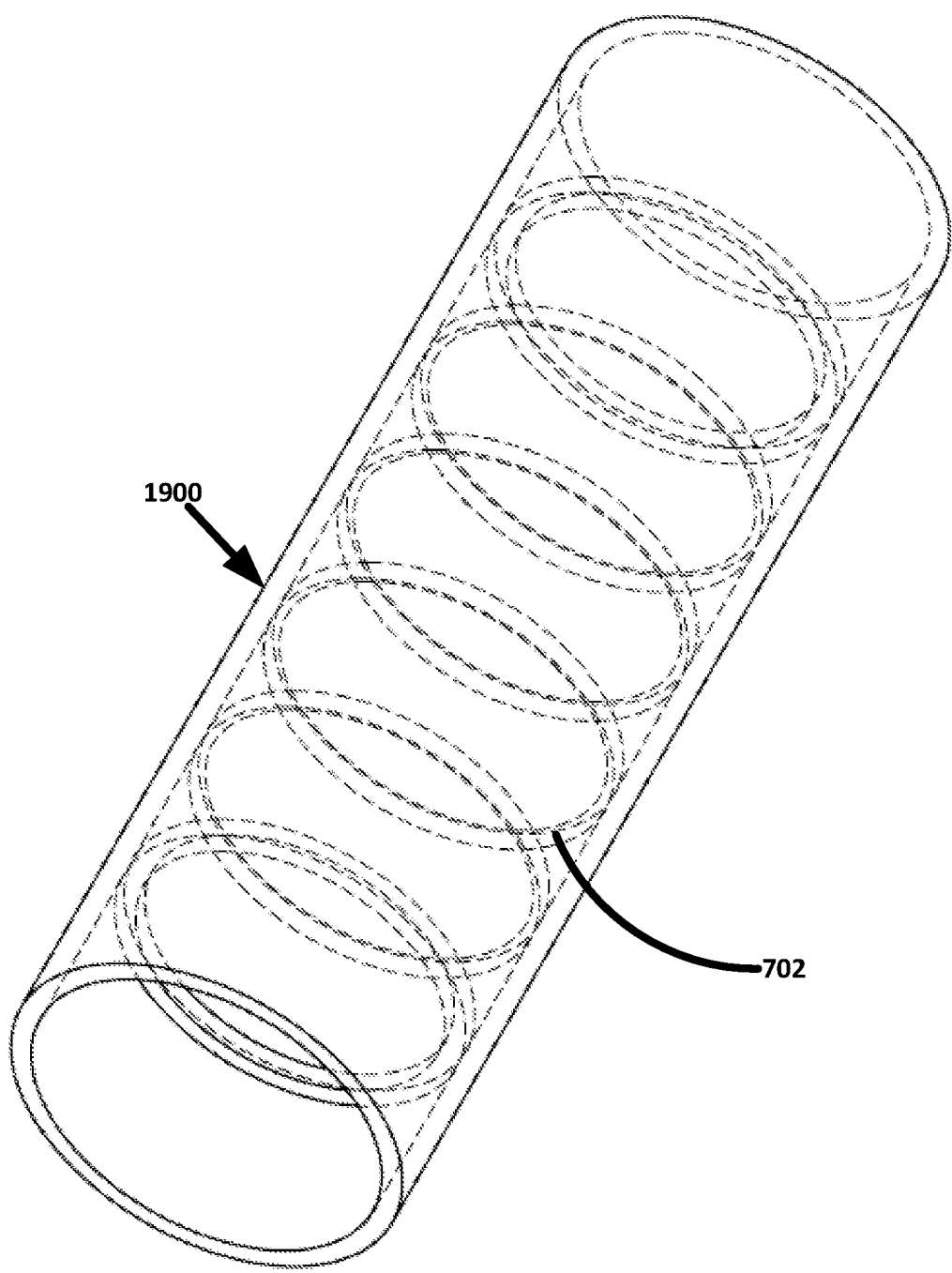
FIG. 19 shows a perspective view of an embodiment of an inflation balloon 140 of the catheter system 100.

FIG. 19 shows a perspective view of an embodiment of an inflation balloon 140 of the catheter system 100. The inflation balloon 1900 has ridges 702. The inflation balloon 1900 may be an embodiment of the inflation balloon 140. In other embodiments, inflation balloon 1900 may not have all of the elements or features listed and/or may have other elements or features instead of or in addition to those listed. The inflation balloon 1900 may be an embodiment of the inflation balloon 140.

Figure 20:
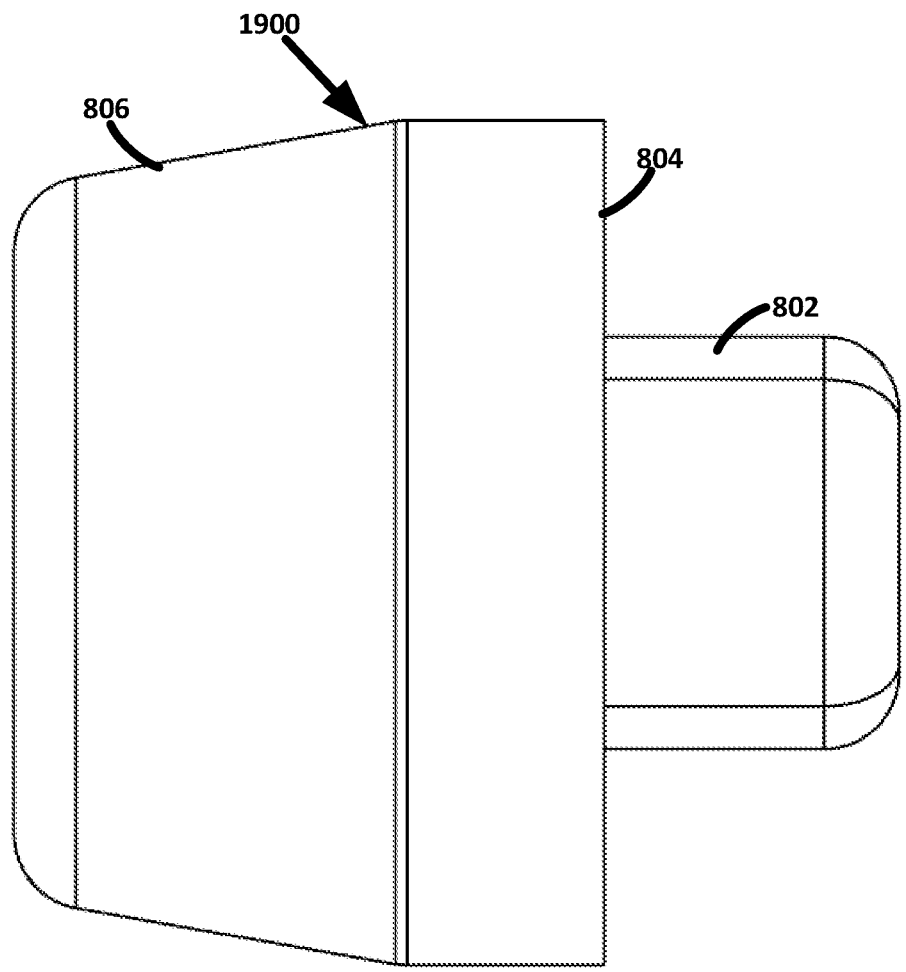
FIG. 20 shows a side view of an embodiment of an end cap 134 of the catheter system 100.

FIG. 20 shows a side view of an embodiment of an end cap 134 of the catheter system 100. The end cap 2000 has a plug 802 and a flat interface 804. The end cap 2000 may be an embodiment of the end cap 134. In other embodiments, end cap 2000 may not have all of the elements or features listed and/or may have other elements or features instead of or in addition to those listed. The end cap 2000 may be an embodiment of the end cap 134.

Figure 21:
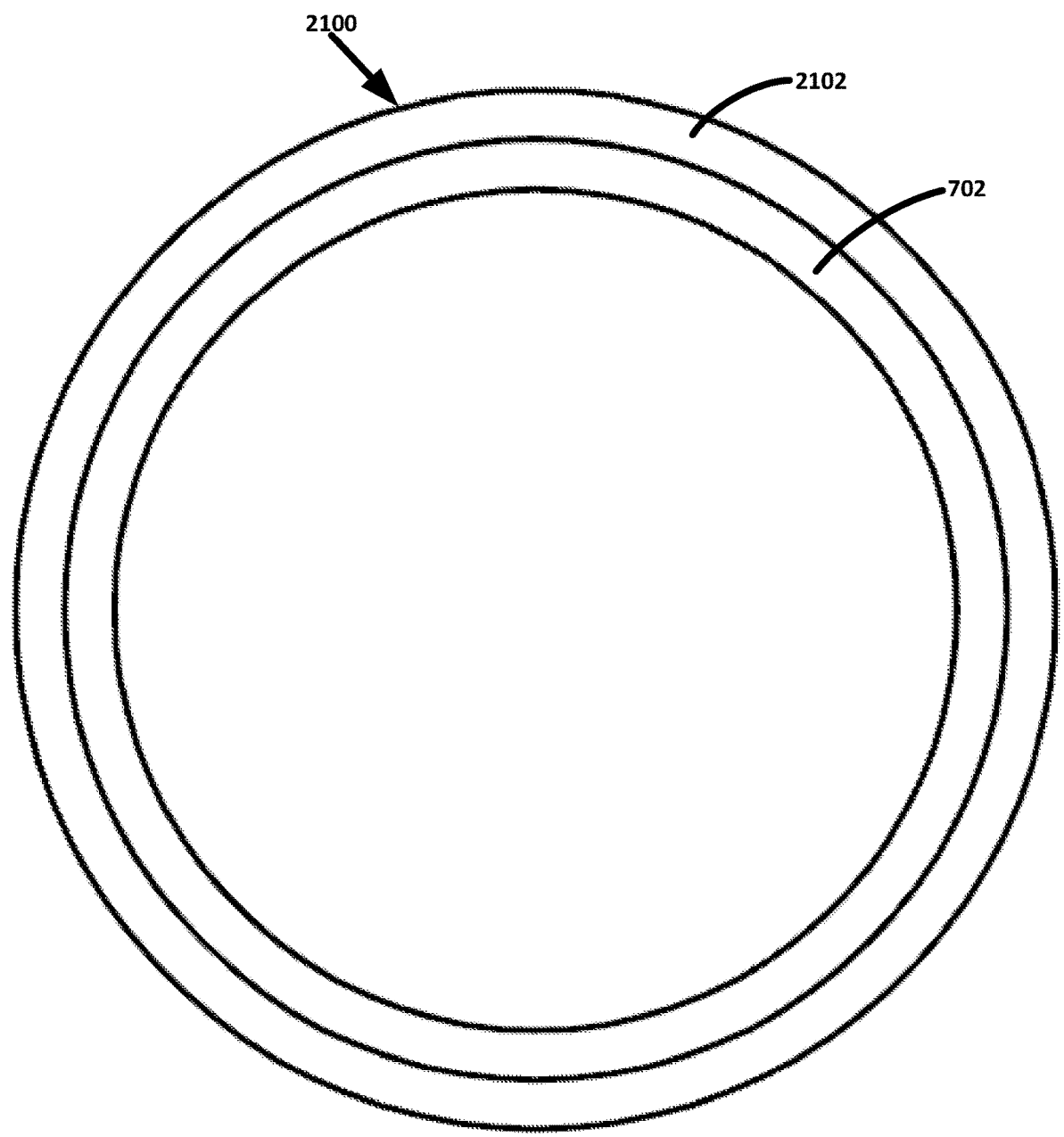
FIG. 21 shows a cross-sectional view of an embodiment of the inflation balloon 140.

FIG. 21 shows a cross-sectional view of an embodiment of an inflation balloon 140. The inflation balloon 2100 may have an exterior inflation balloon layer 2102 and ridges 702. The external inflation balloon layer 2102 is the outside layer of the inflation balloon 140. The ridges 702 are ridges within the inflation balloon 700 that provide support and prevent sticking of the layers of material to allow for inflation. In other embodiments, inflation balloon 2100 may not have all of the elements or features listed and/or may have other elements or features instead of or in addition to those listed. The inflation balloon 2100 may be an embodiment of the inflation balloon 140.

Figure 22:
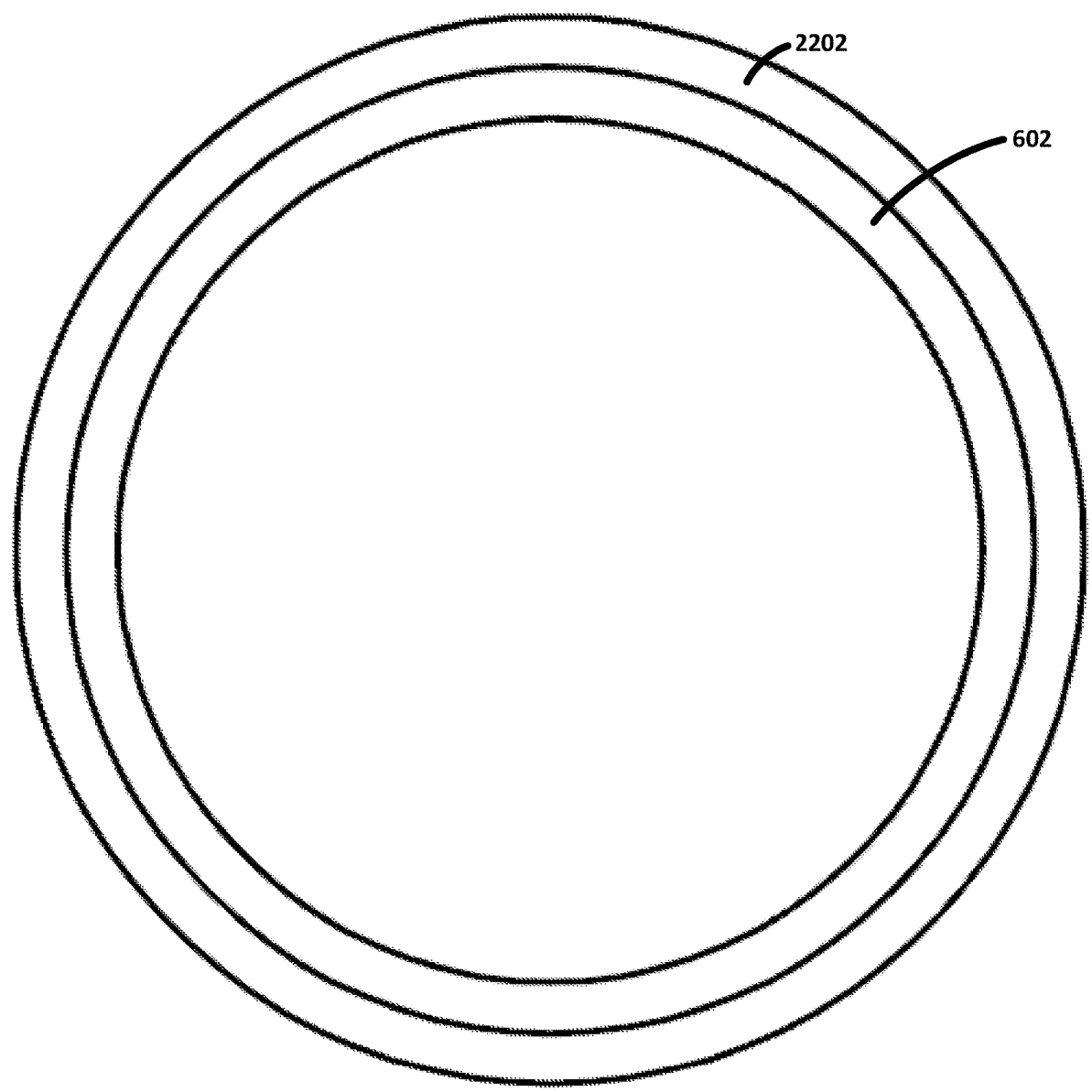
FIG. 22 shows a cross-sectional view of an embodiment of the drug delivery balloon 150.

FIG. 22 shows a cross-sectional view of an embodiment of a drug delivery balloon 150. The drug delivery balloon 2200 may have an exterior drug delivery balloon layer 2202 and ridges 602. The external drug delivery balloon layer 2202 is the outside layer of the drug delivery balloon 150.

Ridges 602 are ridges within the balloons that provide support and prevent sticking of the layers of material to allow for drug delivery. In other embodiments, drug delivery balloon 2200 may not have all of the elements or features listed and/or may have other elements or features instead of or in addition to those listed. The drug delivery balloon 2200 may be an embodiment of the drug delivery balloon 150.

Figure 23:
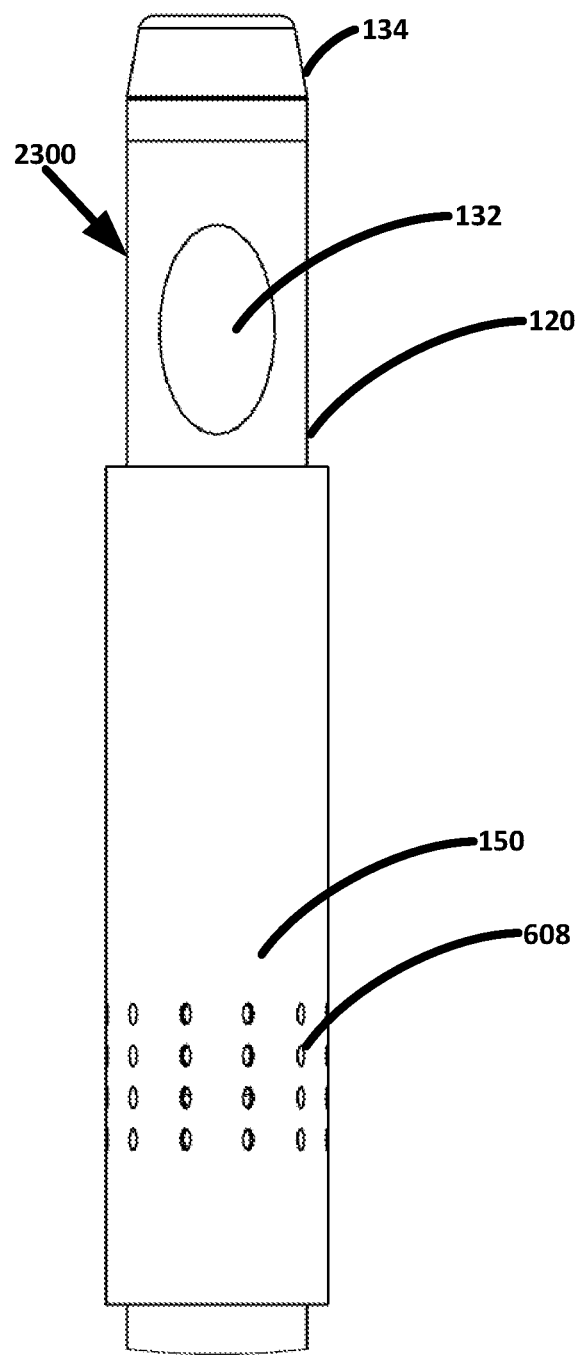
FIG. 23 shows an exterior view of an embodiment of a distal portion of the catheter 100.

FIG. 23 shows an exterior view of an embodiment of a distal portion of the catheter system 100. The catheter 2300 may have a shaft 120, a drainage aperture 132, a drug delivery balloon 150, an end cap 134, and holes 608. In other embodiments, catheter 2300 may not have all of the elements or features listed and/or may have other elements or features instead of or in addition to those listed. The catheter 2300 may be an embodiment of the catheter 100. The shaft 120 is an elongate, hollow body with a number of lumens and orifices for transfer of various fluids. The drainage aperture 132 is a hole in the shaft 120, which provides bladder fluid access from the bladder to the shaft 120, and eventually an external bladder fluid reservoir. The drug delivery balloon 150 is a balloon, which distributes drug fluids to the surfaces of the bladder 105. The end cap 134 is a cap, which abuts distal end of the shaft 120. The holes 608 are holes in the drug delivery balloon 600 through which drug fluids may flow.

Figure 24:
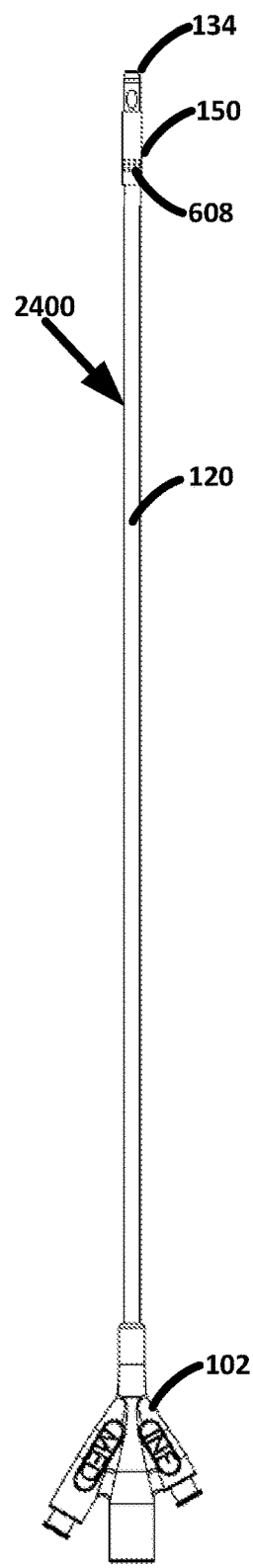
FIG. 24 shows an external view of an embodiment of the catheter system 100.

FIG. 24 shows an external view of an embodiment of the catheter system 100. The catheter system 2400 may have an input manifold 102, a shaft 120, and end cap 134, and a drug delivery balloon 150. In other embodiments, catheter 2400 may not have all of the elements or features listed and/or may have other elements or features instead of or in addition to those listed. The catheter 2400 may be an embodiment of the catheter 100. The input manifold 102 is a component that receives input fluids such as inflation and drug fluid from a source and depletes drainage from the bladder and deflating inflation fluids, received by the input manifold 102 from the shaft 120. The shaft 120 is an elongate, hollow body with a number of lumens and orifices for transfer of various fluids. The end cap 134 is a cap, which abuts the distal end of the shaft 120. The drug delivery balloon 150 is a balloon, which distributes drug fluids to the surfaces of the bladder 105.

Figure 25:
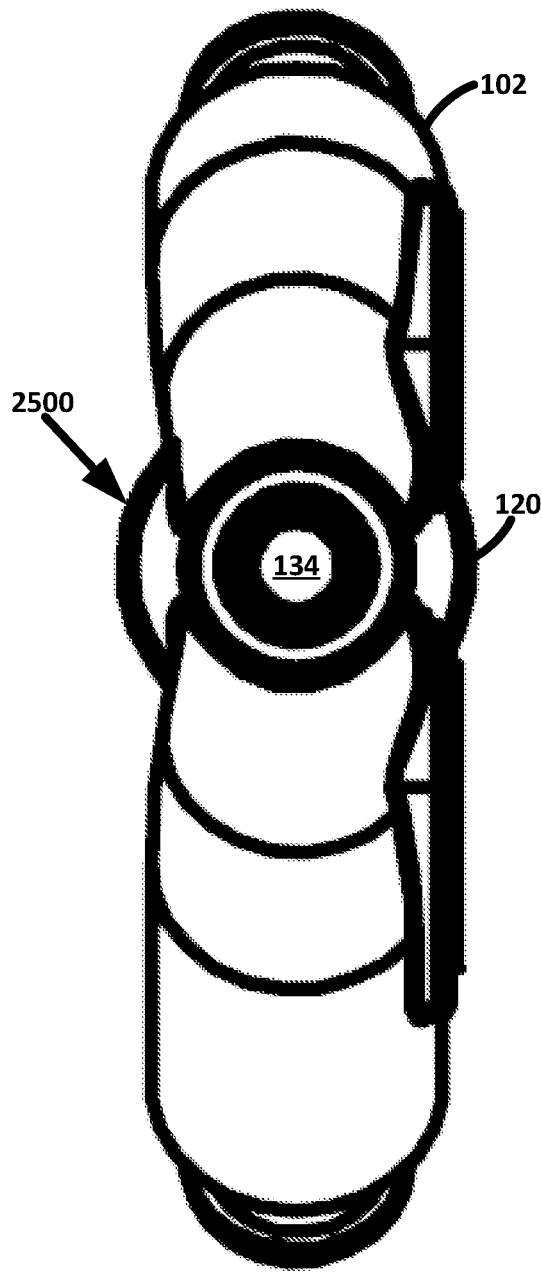
FIG. 25 shows an external, head-on view of an embodiment of a catheter 100 from the distal end of the catheter 100.

FIG. 25 shows and external heads on view of an embodiment of a catheter 100 from the distal end of the catheter 100. The catheter 2500 may have an input manifold 102 and a shaft 120. The input manifold 102 is a component that receives input fluids such as inflation and drug fluid from a source and depletes drainage from the bladder and deflating inflation fluids, received by the input manifold 102 from the shaft 120. The shaft 120 is an elongate, hollow body with a number of lumens and orifices for transfer of various fluids. In other embodiments, catheter 2500 may not have all of the elements or features listed and/or may have other elements or features instead of or in addition to those listed. The catheter 2500 may be an embodiment of the catheter 100.

Figure 26:
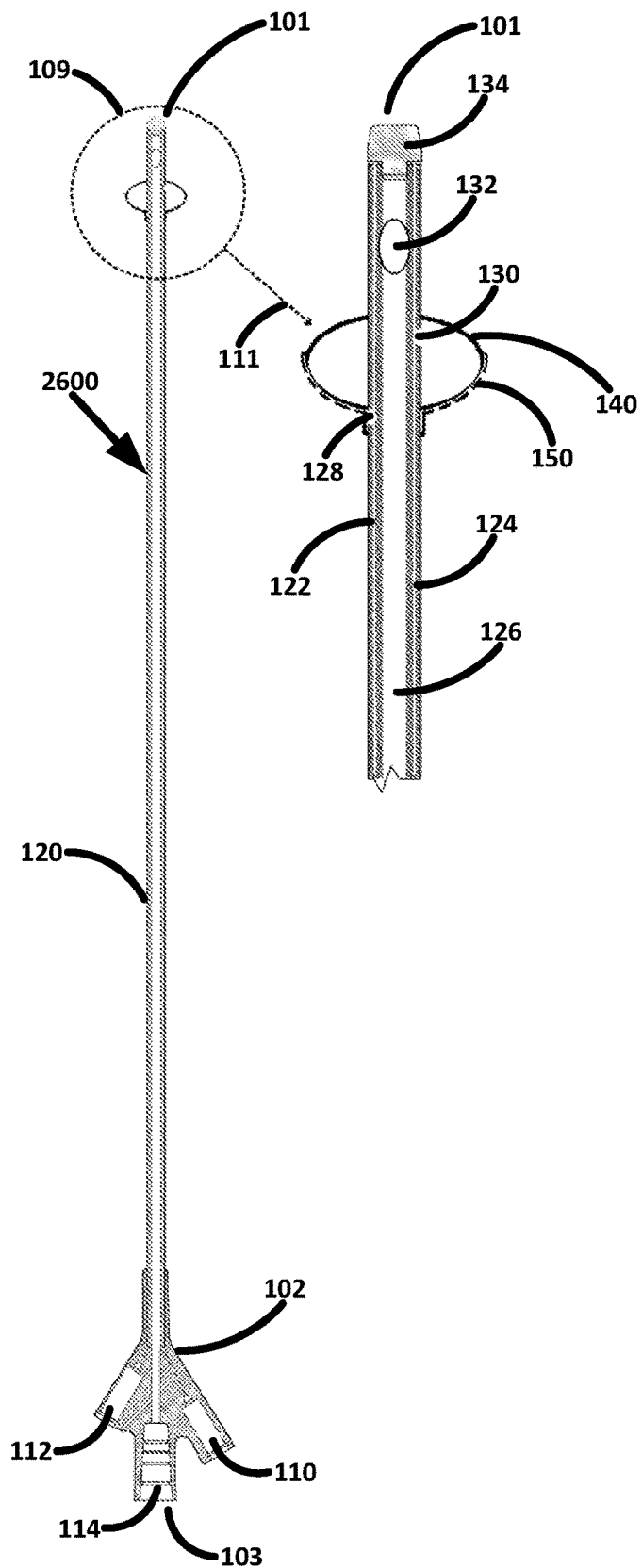
FIG. 26 shows an interior bisected view of an embodiment of a catheter 100 with an inflated inflation balloon that is not inserted into the bladder 105.

FIG. 26 shows an interior bisected view of an embodiment of a catheter 100 with an inflated inflation balloon that is not inserted into the bladder 105. The catheter system 2600 may have an input manifold 102, an inflation fluid input 110, a drug delivery fluid input 112, a bladder drainage output 114, a shaft 120, a drug delivery lumen 122, an inflation fluid lumen 124, a bladder fluid lumen 126, a drug fluid side hole 128, an inflation fluid side hole 130, a drainage aperture 132, an end cap 134, an inflation balloon 140, a drug delivery balloon 150, a distal side 101, a proximal side 103, a focus circle 109, and a zoom view of the focus circle 111. In other embodiments, catheter 2600 may not have all of the elements or features listed and/or may have other elements or features instead of or in addition to those listed. The catheter 2600 may be an embodiment of the catheter 100.

The input manifold 102 is a component that receives input fluids such as inflation and drug fluid from a source and depletes drainage from the bladder and deflating inflation fluids, received by the input manifold 102 from the shaft 120. The inflation fluid input 110 is an input and output, through which inflation fluid is added or removed for the purposes of inflating or deflating an inflation balloon. The drug fluid input 112 is an input, which receives drug fluids from a source. The bladder drainage output 114 is the output through which urinary bladder fluids and drainage are expelled from the catheter system. The shaft 120 is an elongate, hollow body with a number of lumens and orifices for transfer of various fluids. The drug delivery lumen 122 is a channel within the shaft 120 for communicating drug containing fluids from a drug fluid input 112 to a drug delivery balloon 150. The inflation lumen 124 is a channel within the shaft 120 for communicating inflation fluids from an inflation fluid input 110 to the inflation balloon 140. The bladder fluid lumen 126 is a lumen within the shaft 120 that allows fluid communication of bladder fluids between the bladder and an external bladder fluid reservoir. The drug fluid side hole 128 is a hole in the shaft 120, which provides open fluid access to the drug delivery lumen 122. The inflation fluid side hole 130 is a hole in the shaft 120, which provides open fluid access to the inflation lumen 124. The drainage aperture 132 is a hole in the shaft 120, which provides bladder fluid access from the bladder to the shaft 120, and eventually an external bladder fluid reservoir. The end cap 134 is a cap, which abuts the distal end of the shaft 120. The inflation balloon 140 is a balloon, which is inflated within the bladder to hold the catheter assembly system 100 in place by applying pressure on the bladder wall. The drug delivery balloon 150 is a balloon, which distributes drug fluids to the surfaces of the bladder 105. The distal direction 101 is a reference direction, which points towards the end of the catheter system 100 within the bladder. The distal direction 101 is towards the human body receiving the catheter and away from the location in the catheter system 100 where drug and inflation fluids are introduced in the input manifold 102. The proximal direction 103 is a reference direction, which points towards the end of the catheter system 100 with the input manifold. The proximal direction 103 points away from the human body receiving the catheter system 100 and towards the input manifold in the catheter system 100 where drug and inflation fluids are introduced. The proximal direction 103 is opposite the distal direction 101.

Alternatives and Extensions

The catheter system 100 may have an external porous membrane with prefilled drug solutions such that there is no need for a drug delivery balloon, drug fluid lumen or drug fluid input.

While various embodiments have been described above, it should be understood that the various embodiments have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with the claims' full scope of equivalents.

When a list has been presented in the detailed description, the list is intended to be non-exclusive. If a descriptive term is added to the end of or beginning of a list in the detailed description, the list may include all elements having been qualified by the descriptive term as well as none or some of the elements (including the last) having been qualified by the final descriptive term. If elements of a list in the detailed description are redundant or overlap, the redundancy and the overlapping imply nothing except potentially an attempt to disclose something to different audiences or describing similar or overlapping elements with different scopes, or possibly clerical error, and all elements should be considered independently.

Exemplary Claim Limitations (these are not Claims)

The following is a structured list of potential claim limitations in no particular order and no particular combination. The following claim limitations may be used in any combination, solitarily, or with omissions and are merely listed in an exemplary fashion. All combinations of these limitation are contemplated by this specification.

A catheter 100, comprising:
an input manifold 102, the input manifold 102 being coupled to a shaft 120 the input manifold 102 having at least three inputs/outputs, the inputs/outputs being:
  a drug fluid input 112, for receiving drug fluids, the drug fluid input 112 being internal to, and along the length of the input manifold 102, the drug fluid input 112 being coupled to a drug delivery lumen 122, the drug fluid input 112 being in fluid communication with the drug delivery lumen 122, the drug fluid input 112 configured to receive at least one or all of:
    a Luer taper configured device, one of:
      a Luer-Lok fitted device; or
      a Luer-Slip slipping fitted device;
    a syringe; or
    a line from a drug delivery reservoir;
    the drug fluid input 112 configured to received a tip with a diameter of at least one of 0.1", 0.9", 0.14", 1", 0.19", 1.10", 0.24", 0.25", 0.26", 11/32", 13/32", 16/32", 17/32", 5/8", 9/16", 13/16", 3/4", 29/32", 39/32", 9/8", 1.55 mm, 1.81 mm, 0.41 mm, 0.71 mm, 0.61 mm, 0.91 mm, 0.33 mm, 0.63 mm, 0.2 mm, or 0.41 mm;
  an inflation fluid input 110, for receiving and dispensing inflation fluids, the inflation fluid input 110 being internal to, and along the length of the input manifold 102, the inflation fluid input 110 being coupled to an inflation lumen 124, the inflation fluid input 110 being in fluid communication with the inflation lumen 124, the inflation fluid input 110 configured to receive at least one of:
    a Luer taper configured device, one, some or all of:
      a Luer-Lok fitted device; or
      a Luer-Slip slipping fitted device;
    a syringe; or
    a line from an inflation fluid reservoir;
    the inflation fluid input 110 configured to received a tip with a diameter of at least one of 0.1", 0.9", 0.14", 1", 0.19", 1.10", 0.24", 0.25", 0.26", 11/32", 13/32", 16/32", 17/32", 5/8", 9/16", 13/16", 3/4", 29/32", 39/32", 9/8", 1.55 mm, 1.81 mm, 0.41 mm, 0.71 mm, 0.61 mm, 0.91 mm, 0.33 mm, 0.63 mm, 0.2 mm, and 0.41 mm; and
  a bladder drainage output 114, for receiving drainage from the bladder, the bladder drainage output 114 being internal to, and along the length of the input manifold 102, the bladder drainage output 114 coupled to the bladder fluid lumen 126, the bladder drainage output 114 being in fluid communication with the bladder fluid lumen 126;
the shaft 120, the shaft being an elongate member, having at least three lumens, the at least three lumens including a drug delivery lumen 122, an inflation lumen 124, and a bladder fluid lumen 126, wherein the drug delivery 122 lumen does not contain an electronic wire, wherein the inflation lumen 124 does not contain electronic wire, wherein the bladder fluid lumen 126 does not contain an electronic wire,
the drug delivery lumen 122, the drug delivery lumen 122 being a channel within the shaft 120, the drug delivery lumen 122 transmitting drug fluids, the drug delivery lumen 122 being in fluid communication with the drug fluid input 112 and a drug fluid side hole 128, the drug delivery lumen 122 having a diameter of one of the following:
  0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.054", 0.056", 0.057", 0.058", 0.059", 0.06", 0.5 mm, 0.7 mm, 1 mm, 1.6 mm, 0.8 mm, 1.3 mm, 1.5 mm, or ranges of diameter of 0.005"-0.02", 0.011"-0.0147", 0.01"-0.05", 0.01"-0.06", 0.02"-0.04", 0.02"-0.05", 0.03"-0.044", 0.04"-0.053", 0.02"-0.06", 0.02"-0.053", 0.2 mm-0.4 mm, 0.1 mm-0.5 mm, 0.27 mm-0.44 mm, 0.5 mm-0.8 mm, 0.5 mm-1.5 mm, 0.5 mm-1 mm, 0.7 mm-1 mm, 0.7 mm-1.5 mm, or 0.7 mm-1.6 mm;
the inflation lumen 124, the inflation lumen 124 being a channel within the shaft 120, the inflation lumen 124 being in fluid communication with the inflation fluid input 110 and an inflation side hole 130, the inflation lumen 124 having a diameter of one of the following:
  0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.054", 0.056", 0.057", 0.058", 0.059", 0.06", 0.5 mm, 0.7 mm, 1 mm, 1.6 mm, 0.8 mm, 1.3 mm, 1.5 mm, or ranges of diameter of 0.005"-0.02", 0.011"-0.0147", 0.01"-0.05", 0.01"-0.06", 0.02"-0.04", 0.02"-0.05", 0.03"-0.044", 0.04"-0.053", 0.02"-0.06", 0.02"-0.053", 0.2 mm-0.4 mm, 0.1 mm-0.5 mm, 0.27 mm-0.44 mm, 0.5 mm-0.8 mm, 0.5 mm-1.5 mm, 0.5 mm-1 mm, 0.7 mm-1 mm, 0.7 mm-1.5 mm, or 0.7 mm-1.6 mm;
wherein the bladder fluid lumen 126 is on the opposite side of the shaft 120 of the drug delivery lumen 122; the bladder fluid lumen 126, the bladder fluid lumen 126 being a channel within the shaft 120, the bladder fluid lumen 126 being in fluid communication with a drainage aperture 132 and the bladder drainage output 114, the bladder fluid lumen 126 having an inconsistent diameter, the bladder fluid lumen 126 having a maximum diameter of one of 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.101", 0.102", 0.103", 0.104", 0.105", 0.106", 0.107", 0.108", 0.109", 0.11", 0.11", 0.112", 0.113", 0.114", 0.115", 0.116", 0.117", 0.118", 0.119", 0.12", 0.13", 0.14", 0.15", 0.16", 0.17", 0.18", 0.19", 0.2", 0.3", 0.4", 0.5", 0.6", 0.7", 0.8", or a range of 0.08"-0.5", 0.07"-0.5", 0.08"-0.1", 0.07"-0.1", 0.07"-0.2", 0.095"-0.2", 0.1"-0.2", 0.105"-0.2", 0.1"-0.12", 0.09"-0.12", or 0.099"-0.111", the bladder fluid lumen 126 having a minimum diameter of one of 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.11", 0.12", 0.13", 0.14", 0.15", 0.16", 0.17", 0.18", 0.19", 0.2", 0.3", 0.4", 0.5", 0.6", 0.7", 0.8", or a range of 0.08"-0.5", 0.07"-0.5", 0.08"-0.1", 0.07"-0.1", 0.07"-0.2", 0.09"-0.12", or 0.093"-0.118";

the drug fluid side hole 128 being a hole in the side of the shaft 120 which exposes the drug delivery lumen 122, the fluid side hole 128 being in fluid communication with the space between the interior of the drug delivery balloon 150 and the exterior of the inflation balloon 140, and the drug delivery lumen 122, the drug fluid side hole 128 having a diameter of 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", ⅛", ¼", 0.5", ¾", 1", 1.5", 2", or a range of 0.071"-0.091", 0.085"-0.1", 0.1 mm-2 mm, 0.2 mm-0.5 mm, 0.5 mm-1 mm, 0.1 mm-5 mm, 1 mm-10 mm, 5 mm-15 mm, 5 mm-34 mm, 10 mm-15 mm, 12 mm-34 mm, or 0.1 mm-34 mm, the drug fluid side hole 128 located proximally to an inflation fluid side hole 130 and distally of a proximal end of the shaft, the distance between the drug fluid side hole 128 and a distal edge of the shaft 120 being one of 1 mm, 2 mm, 3 mm, 4 mm, 5 mm, 6 mm, 7 mm, 8 mm, mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21", 2", 3", 4", or 5" or in a range of 0.25"-0.75", 0.5"-0.7", 0.5"-1", 0.25"-1.5", 0.1 mm-2 mm, 0.2 mm-0.5 mm, 0.5 mm-1 mm, 0.1 mm-5 mm, 1 mm-10 mm, 5 mm-15 mm, 5 mm-34 mm, 10 mm-15 mm, 12 mm-34 mm, or 0.1 mm-34 mm, 0.3"-0.55", 0.3"-1.21", 0.3"-5", 0.8"-1.2", 0.8"-2", 0.8"-3", 0.6"-3", or 0.8"-4", the drug fluid side hole 128 having a maximum depth of drug fluid side hole 406 of 0.06", 0.07", 0.071", 0.072", 0.073", 0.074", 0.075", 0.076", 0.077", 0.078", 0.079", 0.08", 0.081", 0.082", 0.083", 0.084", 0.085", 0.086", 0.087", 0.089", 0.09", 0.1", 0.15", 0.2", or from a range of 0.06"-0.1", 0.07"-0.2", 0.071"-0.1", 0.071"-0.089", 0.06"-0.2", 0.06"-3", or 0.06"-0.4";

the inflation side hole 130 being a hole in the side of the shaft 120 which exposes the inflation lumen 124, the inflation side hole 130 being in fluid communication with the space between the interior of the inflation balloon 140 and the shaft and the inflation lumen 124, the inflation side hole 130 having a diameter of 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", ⅛", ¼", 0.5", ¾", 1", 1.5", 2", or a range of 0.071"-0.091", 0.085"-0.1", 0.1 mm-2 mm, 0.2 mm-0.5 mm, 0.5 mm-1 mm, 0.1 mm-5 mm, 1 mm-10 mm, 5 mm-15 mm, 5 mm-34 mm, 10 mm-15 mm, 12 mm-34 mm, or 0.1 mm-34 mm, the inflation side hole 130 located distally of the drug fluid side hole 128 and proximally of the drainage aperture 132, the distance between the inflation fluid side hole 130 and the distal edge of the shaft 120 being one of 1 mm, 2 mm, 3 mm, 4 mm, 5 mm, 6 mm, 7 mm, 8 mm, mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, ¾", ½", 0.25", 0.26", 0.27", 0.28", 0.29", 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21", ¾", 1", 1¼", 1½", 1¾", 2", 3", 4", 5", 6", 7", 8", 9" or in a range of 0.3"-0.55", 0.3"-1.21", 0.3"-5", 0.8"-1.2", 0.8"-2", 0.8"-3", 0.6"-3", 0.8"-4"0.25"-0.75", 0.5"-0.7", 0.5"-1", 0.25"-1.5, or 0.25"-9", the inflation side hole 130 having a maximum depth of inflation side hole 408 of 0.06", 0.07", 0.071", 0.072", 0.073", 0.074", 0.075", 0.076", 0.077", 0.078", 0.079", 0.08", 0.081", 0.082", 0.083", 0.084", 0.085", 0.086", 0.087", 0.089", 0.09", 0.1", 0.15", 0.2", or within a range of 0.06"-0.1", 0.07"-0.2", 0.071"-0.1", 0.071"-0.089", 0.06"-0.2", 0.06"-3", or 0.06"-0.4";

the drainage aperture 132, being a hole in the shaft 120 which allows bladder fluids to escape from the bladder to the catheter 100, the drainage aperture 132 being in fluid communication with bladder fluids and the bladder fluid lumen 126, the drainage aperture 132 being a hole in the shaft 120, the drainage aperture 132 being between the distal end of the shaft 120 and the drug fluid side hole 128, the drainage aperture 132 having a diameter at the drainage aperture's 132 widest point along the shaft 120 of 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 0.07", 0.08", 0.09", 0.1", 0.11", 0.12", 0.13", 0.14", 0.15", 0.16", 0.17", 0.18", 0.19", 0.2", 0.21", 0.22", 0.23", 0.24", 0.25", 0.26", ⅛", ¼", 0.5", ¾", 1", 1.5", 2", or a range of 0.1 mm-2 mm, 0.2 mm-0.5 mm, 0.5 mm-1 mm, 0.1 mm-5 mm, 1 mm-10 mm, 5 mm-15 mm, 5 mm-34 mm, 10 mm-15 mm, 12 mm-34 mm, or 0.1 mm-34 mm, the drainage aperture 132 having a diameter at the drainage aperture's narrowest point along the shaft 120 of 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3.0 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 0.1", 0.11", 0.12", 0.13", 0.14", 0.15", 0.16", 0.17", 0.18", 0.19", 0.2", 0.21", 0.22", 0.23", 0.24", 0.25", 0.26", 0.27", 0.28", 0.29", 0.3", 0.31", 0.32", 0.4", ⅛", ¼", 0.5", ¾", 1", 1.5", 2", or a range of 0.1"-0.25", 0.1"-0.3", 0.1"-0.5", 0.1 mm-2 mm, 0.2 mm-0.5 mm, 0.5 mm-1 mm, 0.1 mm-5 mm, 1 mm-10 mm, 5 mm-15 mm, 5 mm-34 mm, 10 mm-15 mm, 12 mm-34 mm, or 0.1 mm-34 mm, the drainage aperture 132 has a distance from the distal end of the shaft to the distal end of the drainage aperture 418 being the distance from the distal end of the shaft to the drainage aperture 432, the distance from the distal end of the shaft to the distal end of the drainage aperture 418 being on of 0.07", 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.11", 0.12", 0.13", 0.14", 0.15", 0.16", 0.17", 0.18", 0.19", 0.2", 0.3", 0.4", 0.5", 0.6", 0.7", 0.8", or within a range of 0.07"-0.8", 0.07"-0.12", 0.07"-0.09", 0.07"-0.19", or 0.07"-0.1", the drainage aperture being a murphy eye; and, the end cap 134, being a cap coupled to the distal end of the shaft 120, the end cap 134 having a plug 802 to conform to the interior of the bladder fluid lumen 126, the plug having a depth of 0.05", 0.051", 0.052", 0.053", 0.054", 0.055", 0.056", 0.057", 0.058", 0.059", 0.06", 0.061", 0.062", 0.063", 0.064", 0.065", 0.066", 0.067", 0.068", 0.069", 0.07", or from a range of 0.05"-0.07", 0.055"-0.065", or 0.059"-0.061", the end cap 134 having a flat interface 804 which abuts and prevents flow from the ends of the drug delivery lumen 122 and the inflation fluid lumen 124 at the distal end of the shaft, the end cap further having an angled exterior 806 with a lead-in edge for easier catheter 100 insertion;

wherein the shortest distance between the interior of the bladder fluid lumen and the exterior of the shaft 510 being the shortest distance between the shaft 120 and the interior of the bladder fluid lumen 126, is 0.025", 0.026", 0.027", 0.028", 0.029", 0.03", 0.031", 0.032", 0.033", 0.034", 0.035", 0.036", 0.037", 0.038", 0.039", 0.04", 0.05", 0.06", 0.07", 0.08", 0.09", 0.1", or in a range of 0.025"-0.04", 0.025"-0.1", 0.029"-0.035", or 0.025"-0.1", the shortest distance between the external surface of the shaft and the interior of the drug delivery lumen 512, being the shortest distance between the external surface of the shaft 120 and the interior of the drug delivery lumen 122, the shortest distance between the external surface of the shaft and the interior of the drug delivery lumen 512 being 0.005", 0.006", 0.007", 0.008", 0.009", 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, or within a range of 0.005"-0.1", 0.005"-0.025", 0.005"-0.06", 0.011"-0.017", or 0.01"-0.02", the shortest distance between the external surface of the shaft and the interior of the drug delivery lumen 512 being the same as the shortest distance between the external surface of the shaft 500 and the interior of the inflation lumen 524 symmetrically about the bladder fluid lumen 126, the distance between the internal surface of the drug delivery lumen and the interior surface of the bladder fluid lumen 514 being the distance between the internal surface of the drug delivery lumen 522 and the interior surface of the bladder fluid lumen 526, the distance between the internal surface of the drug delivery lumen and the interior surface of the bladder fluid lumen 514 being 0.005", 0.006", 0.007", 0.008", 0.009", 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037" 0.044", 0.053", 0.06", 0.5 mm, 0.7 mm, 1 mm, 1.6 mm, 0.8 mm, 1.3 mm, 1.5 mm, or within a range of 0.005"-0.1", 0.005"-0.025", 0.005"-0.06", 0.011"-0.017", or 0.01"-0.02", the distance between the internal surface of the drug delivery lumen and the interior surface of the bladder fluid lumen 514 being the same as the distance between the internal surface of the inflation lumen 524 and the interior surface of the bladder fluid lumen 526 symmetrically about the bladder fluid lumen 526, a distance between the drug fluid side hole and inflation fluid side hole 420 being a distance along a line parallel with the longest length of the shaft 120 between drug fluid side hole 128 and the inflation side hole 130 as if the two were on the same side from the center of the inflation side hole 130 to the center of the drug fluid side hole 128, the distance between the drug fluid side hole and inflation fluid side hole 420 being 1 mm, 2 mm, 3 mm, 4 mm, 5 mm, 6 mm, 7 mm, 8 mm, mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, 41 mm, 42 mm, 43 mm, 44 mm, 45 mm, 46 mm, 47 mm, 48 mm, 49 mm, 50 mm, 0.2", 0.21", 0.22", 0.23", 0.24", 0.25", 0.26", 0.27", 0.28", 0.29", 0.3", 0.31", 0.32", 0.33", 0.34", 0.35", 0.36", 0.37", 0.38", 0.39", ¼", ½", ¾", 1", 1¼", 1½", 1¾", 2", 3", 4", 5", 6", 7", 8", 9", 10", or from a range of 0.2"-10", 0.2"-0.39" or 0.3"-0.4", the distance between the drug fluid side hole and the inflation side hole 420 being small enough for the drug delivery balloon 150 to appear substantially flush with the surface of the inflation balloon 130, the shaft 120 composed of a blending of two part silicone gumstock on a rolling mill to create medical grade silicone.

the inflation balloon 140, being a balloon which is coupled to the shaft 120 and inflates in order to keep the catheter 100 in place by pressure fit, the inflation balloon 140 having a ridge 602, the ridge 602 being for support to prevent a balloon membrane from sticking to the shaft

120, the ridge 602 having a height of 0.005", 0.006", 0.007", 0.008", 0.009", 0.01", 0.011", 0.012", 0.013", 0.014", 0.04", 0.015", 0.016", 0.017", 0.018", 0.019", 0.02", 0.1 mm, 0.2 mm, 0.3 mm, 0.4 mm, 0.5 mm, 0.6 mm, 0.7 mm, 0.8 mm, 0.9 mm, or within a range of 0.008"-0.02", 0.009"-0.02", 0.005"-0.02", or 0.1 mm-0.9 mm, the ridge 602 having a width of 0.005", 0.006", 0.007", 0.008" 0.009", 0.01", 0.011", 0.012", 0.013", 0.014", 0.04", 0.015", 0.016", 0.017", 0.018", 0.019", 0.02", 0.1 mm, 0.2 mm, 0.3 mm, 0.4 mm, 0.5 mm, 0.6 mm, 0.7 mm, 0.8 mm, 0.9 mm, or within a range of 0.008"-0.02", 0.009"-0.02", 0.005"-0.02", or 0.1 mm-0.9 mm, a distance between ridges 602 of 0.07", 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.101", 0.102", 0.103", 0.104", 0.105", 0.106", 0.107", 0.108", 0.109", 0.11", 0.11", 0.112", 0.113", 0.114", 0.115", 0.116", 0.117", 0.118", 0.119", 0.12", 0.13", 0.14", 0.15", 0.16", 0.17", 0.18", 0.19", 0.2", 0.3", 0.4", 0.5", 0.6", 0.7", 0.8", or within a range of 0.08"-0.5", 0.07"-0.5", 0.08"-0.1", 0.07"-0.1", 0.07"-0.2", 0.095"-0.2", 0.1"-0.2", 0.105"-0.2", 0.1"-0.12", 0.09"-0.12", or 0.099"-0.111", the inflation balloon 140 having a thickness of 0.007", 0.008", 0.009", 0.01", 0.011", 0.012", 0.013", 0.014", 0.015", 0.2 mm, 0.21 mm, 0.22 mm, 0.23 mm, 0.24 mm, 0.25 mm, 0.254 m, 26 mm, 0.27 mm, or within a range of 0.005"-0.015", 0.009"-0.011", 0.008"-0.012", 0.2 mm-0.3 mm, the inflation balloon 140 having a distal inflation balloon coupling site 412, the distal inflation balloon coupling site 412 being on the shaft 120 between the drainage fluid aperture 132 and the inflation fluid side hole 130, the distal inflation balloon coupling site 412 being a distance from the distal end of the shaft of 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1", 1.1", 1.2", 1.3", 1.4", 2", 3", 4", 5", or in a range of 0.3"-0.6", 0.3"-1", 0.3"-1.4", 0.55"-1", 0.6"-1", 0.6"-0.95", 0.6"-2", 0.6"-3", or 0.6"-4", the inflation balloon 140 having a proximal inflation balloon coupling site 414, the proximal inflation balloon coupling site 414 being on the shaft between the inflation fluid side hole 130 and the drug fluid side hole 128, the proximal inflation balloon coupling site 414 being a distance from the distal end of the shaft 120 of 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21", 2", 3", 4", 5", or in a range of 0.3"-0.55", 0.3"-1.21", 0.3"-5", 0.8"-1.2", 0.8"-2", 0.8"-3", 0.6"-3", or 0.8"-4", the proximal inflation balloon coupling site 414 being a distance from the drug fluid side hole 128 when the inflation balloon 140 is inflated, for instance, 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, or within a range of 0.005"-0.02", 0.011"-0.0147", 0.01"-0.05", 0.01"-0.06", 0.02"-0.04", 0.02"-0.05", 0.03"-0.044", 0.04"-0.053", 0.02"-0.06", 0.02"-0.053", 0.2 mm-0.4 mm, 0.1 mm-0.5 mm, 0.27 mm-0.44 mm, 0.5 mm-0.8 mm, 0.5 mm-1.5 mm, 0.5 mm-1 mm, 0.7 mm-1 mm, 0.7 mm-1.5 mm, or 0.7 mm-1.6 mm; and the drug delivery balloon 150, being a balloon which delivers drug fluid to patient, the drug deliver balloon 150 coupled to at least one of the shaft 120 and the inflation balloon 140, the drug delivery balloon 150 having the ridge 702, the ridge 702 being for support to prevent the balloon membrane from sticking to the shaft 120, the ridge 702 having a height of 0.005", 0.006", 0.007", 0.008", 0.009", 0.01", 0.011", 0.012", 0.013", 0.014", 0.04", 0.015", 0.016", 0.017", 0.018", 0.019", 0.02", 0.1 mm, 0.2 mm, 0.3 mm, 0.4 mm, 0.5 mm, 0.6 mm, 0.7 mm, 0.8 mm, 0.9 mm, or within a range of 0.008"-0.02", 0.009"-0.02", 0.005"-0.02", or 0.1 mm-0.9 mm, the ridge 602 having a width of 0.005", 0.006", 0.007", 0.008", 0.009", 0.01", 0.011", 0.012", 0.013", 0.014", 0.04", 0.015", 0.016", 0.017", 0.018", 0.019", 0.02", 0.1 mm, 0.2 mm, 0.3 mm, 0.4 mm, 0.5 mm, 0.6 mm, 0.7 mm, 0.8 mm, 0.9 mm, or within a range of 0.008"-0.02", 0.009"-0.02", 0.005"-0.02", or 0.1 mm-0.9 mm, the drug delivery balloon 150 having a distance between ridges 702 of 0.07", 0.071", 0.072", 0.073", 0.074", 0.075", 0.076", 0.077", 0.078", 0.079", 0.08", 0.081", 0.082", 0.083", 0.084", 0.085", 0.086", 0.087", 0.088", 0.089", 0.09", 0.091", 0.092", 0.093", 0.094", 0.095", 0.096", 0.097", 0.098", 0.099", 0.1", 0.101", 0.102", 0.103", 0.104", 0.105", 0.106", 0.107", 0.108", 0.109", 0.11", 0.11", 0.112", 0.113", 0.114", 0.115", 0.116", 0.117", 0.118", 0.119", 0.12", 0.13", 0.14", 0.15", 0.16", 0.17", 0.18", 0.19", 0.2", 0.3", 0.4", 0.5", 0.6", 0.7", 0.8", or within a range of 0.08"-0.5", 0.07"-0.5", 0.08"-0.1", 0.07"-0.1", 0.07"-0.2", 0.095"-0.2", 0.1"-0.2", 0.105"-0.2", 0.1"-0.12", 0.09"-0.12", or 0.099"-0.111", the drug delivery balloon 150 having a thickness of 0.007", 0.008", 0.009", 0.01", 0.011", 0.012", 0.013", 0.014", 0.015", 0.2 mm, 0.21 mm, 0.22 mm, 0.23 mm, 0.24 mm, 0.25 mm, 0.254 m, 26 mm, 0.27 mm, or within a range of 0.005"-0.015", 0.009"-0.011", 0.008"-0.012", 0.2 mm-0.3 mm, the drug delivery balloon 150 having a distal drug delivery balloon coupling site 410, the distal drug delivery balloon coupling site 410 being on the shaft 120 between the drug fluid side hole 128 and the drainage aperture 132 or on the inflation balloon 140, the distal drug fluid balloon coupling site 410 being a distance from the distal end of the shaft when the inflation balloon 140 is deflated, of 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1", 1.1", 1.2", 1.3", 1.4", 1", 2", 3", 4", 5", or in a range of 0.3"-0.6", 0.3"-0.5", 0.3"-0.4", 0.4"-0.6", 0.2"-0.6", 0.2"-1.4", 0.2"-5", or 0.55"-1.4", the drug delivery balloon 150 having a drug delivery proximal balloon coupling site 416, the drug delivery balloon proximal coupling site 416 being on the shaft between the drug fluid side hole 128 and the proximal end of the shaft 120, the drug balloon proximal coupling site 416 being a distance from the distal end of the shaft 120 of 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21", 2", 3", 4" or 5", or in a range of 0.3"-1.21", 0.3"-5", 0.55"-1", 0.6"-1", 0.6"-0.95", 0.6"-2", 0.6"-3", 0.6"-4", 0.8"-1.2", 0.8"-2", 0.8"-3", 0.6"-3", 0.8"-4", 0.55"-4", or 0.55"-5", the drug delivery balloon 150 at least partially covering the inflation balloon 140, the drug delivery balloon 150 covering a percentage of the surface area of the inflation balloon 140 of, 5%, 10%, 15%, 20%, 30%, 35%, 40%, 45%, 50%, 55%, 60%, 65%, 70%, 75%, 80%, 85%, greater than 5% but less than 95%, greater than 10% but less than 95%, greater than 15% but less than 80%, greater than 20% but less than 80%, greater than 20% but less than 70%, greater than 25% but less than 90%, less than 95%, less than 90%, less than 80%, less than 85%, less than 75%, less than 70%, less than 67%, less than 65%, less than 60%, less than 55%, less than 50%, less than 45%, less than 40%, less than 35%, less than 33%, less than 30%, less than 25%, or less than 20% surface area of the inflation balloon 140, the drug delivery balloon 150 having an interior diameter substantially the same as the exterior diameter of the inflation balloon 140 when the inflation balloon 140 is deflated, the inflation balloon having holes 608, the holes 608 for dispensing drug fluids from the drug balloon 150, the holes 608 having diameters 610 of 0.02", 0.03", 0.031", 0.032", 0.033", 0.034", 0.035", 0.036", 0.037", 0.038", 039", 0.04", 0.041", 0.042", 0.043", 0.044", 0.045", 0.046", 0.047", 0.048", 0.049", 0.05", 0.06", 0.07" 1 mm, 0.2 mm, 0.3 mm, 0.4 mm, 0.5 mm, 0.6 mm, 0.7 mm, 0.8 mm, 0.9 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.4 mm, 3.5 mm, 3.6 mm, 3.7 mm, 3.8 mm 3.9 mm, 4 mm, or ranges within 0.02"-0.05", 0.02"-0.07", 0.1 mm-4 mm, 0.1 mm-3 mm, or 0.1 mm-2 mm, the holes 608 being arranged in rows of holes, the rows of holes 608 having 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 holes, distances between the rows of holes 608 being 0.03", 0.031", 0.032", 0.033", 0.034", 0.035", 0.035", 0.036", 0.037", 0.038", 0.039", 0.04", 0.041", 0.042", 0.043", 0.044", 0.045", 0.046", 0.047", 0.048", 0.049", 0.05", 0.051", 0.052", or within a range of 0.03"-0.05", 0.035"-0.045", 0.01"-0.052", or 0.01"-0.05", the thickness of the drug delivery balloon 614 being 0.03", 0.031", 0.032", 0.033", 0.034", 0.035", 0.035", 0.036", 0.037", 0.038", 0.039", 0.04", 0.041", 0.042", 0.043", 0.044", 0.045", 0.046", 0.047", 0.048", 0.049", 0.05", 0.051", 0.052", or within a range of 0.03"-0.05", 0.035"-0.045", 0.01"-0.052", or 0.01"-0.05", the holes 608 being located on the proximal side of the drug delivery balloon 150, the holes 608 in the drug balloon 150 being at least partially exposed to the trigone area when implanted;
wherein the catheter 100 is composed at least in part of one of poly-vinyl chloride, polytetrafluoroethylene (also known as "PTFE" or "Teflon"), latex rubber, silicone, silicone-elastomer coated latex, hydrophilic polymer coated latex, silver alloy coated polymer, hydrogel, polyether block amide, nitinol, nylon, polyethylene terephthalate, thermoplastic elastomers, ethylene vinyl acetate, polyetheretherketone, polyethene, polypropylene, and polyurethane, wherein the catheter 100 is composed entirely of silicone, wherein the catheter 100 has three distinct and separate fluid lumens in the shaft, wherein the catheter 100 has a distal end facing a patient using the catheter, wherein the catheter 100 has a proximal end facing a physician and the input/outputs of the input array 102 when being inserted into a patient, wherein drug fluid channel elements, such as the drug fluid input 112, the drug delivery lumen 122, the drug fluid side hole 128, and the drug balloon 150, are all in fluid communication, wherein bladder fluid channel elements, such as the bladder fluid input 114, bladder fluid lumen 126, and drainage aperture 132, are all in fluid communication, wherein inflation fluid elements, such as the inflation input 110, the inflation fluid lumen 124, the inflation fluid side hole 130, and the space between the interior of the inflation fluid balloon 140 and the exterior of the shaft 120 are all in fluid communication, wherein the drug fluid channel elements are not in fluid communication with the bladder fluid channel elements or the inflation fluid channel elements, wherein the bladder fluid channel elements are not be in fluid communication with the drug fluid channel elements and the inflation fluid channel elements, wherein the inflation fluid channel elements are not in fluid communication with the drug fluid channel elements and the bladder fluid channel elements, wherein the inflation fluid and the drug fluid are not in fluid communication;

A method for using a catheter, comprising:
inserting the catheter 100 into a bladder 105, the insertion being via a urethra, first inserting a lead in-edge of an angled exterior 806 of the catheter 100, inserting the catheter 100 until the inflation balloon 140 enters the bladder 105 completely;
inflating the inflation balloon 140 to resist removal from the bladder 105;
pulling the catheter proximally to secure the catheter;
injecting a drug solution into the drug fluid input 112 or coupling a drug fluid pump system to the drug fluid input 112, injecting a drug fluid of the group lidocaine, bupivacaine, diazepam, oxybutlynin, flavoxate, dicyclomine, hyoscyamine sulfate, and tolterodine, injecting lidocaine at a concentration of 9 mg/cc, 10 mg/cc, 11 mg/cc, 12 mg/cc, 13 mg/cc, 14 mg/cc, 15 mg/cc, 16 mg/cc, 17 mg/cc, 18 mg/cc, 19 mg/cc, 20 mg/cc, 21 mg/cc, 22 mg/cc, 23 mg/cc, 24 mg/cc, 25 mg/cc, 26 mg/cc, 27 mg/cc, 28 mg/cc, 29 mg/cc, 30 mg/cc, 31 mg/cc, or within a range of concentrations of 9 mg/cc-15 mg/cc, 10 mg/cc-20 mg/cc, or 9 mg/cc-21 mg/cc, 9 mg/cc-31 mg/cc, injecting diazepam at a concentration of 1 mg/cc, 1.25 mg/cc, 2.5 mg/cc, 5 mg/cc, 6 mg/cc, or within a range of concentration of 1.25 mg/cc-2.5 mg/cc, 1.25 mg/cc-5 mg/cc, 1 mg/cc-5 mg/cc, or 1 mg/cc-6 mg/cc, wherein the drug fluid contains an anti-sposmadic, wherein the drug fluid contains valium, wherein the inflation solution is different from the drug solution, wherein the drug is delivered to a trigone area 107 via the drug delivery balloon 150;
deflating the inflation balloon to prepare to remove the catheter 100; and
removing the catheter 100 through the urethra.

A method for making a catheter, comprising:
making an end cap 134 by molding the end cap 134, the end cap 134 having features, including:

a plug 802, which conforms to the interior of the bladder fluid lumen 126, preventing liquid from escaping out the end of the bladder fluid lumen;

a flat interface 804, which conforms to a distal edge of a shaft 120; and an angled exterior 806 having a leading edge for easier and less painful insertion;

wherein the end cap 134 is formed separately of the shaft body, wherein the end cap 134 is formed by placing the shaft body 120 into an end cap tool to mold directly to the end cap 134.

making a shaft 120 by:
  forming an elongate member, the forming by feeding strips of a medical grade silicone through an extruder.
  creating a pin and die tool for each Foley catheter FR size that is required, the die created to cut as a cross section the lumens and lumen dimensions, including the diameter of the drug delivery lumen 502, the diameter of an inflation lumen 504, a narrowest internal diameter of an inflation lumen 506, a widest diameter width of a bladder fluid lumen 508
  using a variable speed screw feed to apply and maintain a determined pressure on the pin and die as the elongate member may be extruded to simultaneously form the shaft body 120, the drug delivery lumen 124, and the bladder fluid lumen 126;
  monitoring the outside diameter of the elongate member using a laser micrometer;
  cutting, punching, or skiving the elongate member to form a drainage aperture 132, a drug fluid side hole 128, and an inflation side hole 130, the fluid side hole 128 being cut distally with respect to the inflation side hole 130, the drug fluid side hole 128 being cut on an opposite side of the shaft 120 from the inflation side hole 130;
  curing the resultant shaft body 120 of medical silicone grade tubing with a radiant heat oven;
  using (alternatively) an existing blank to form an elongate member
  using (alternatively)
making an inflation balloon 140 by molding a cylindrical polymer sheet with ridges 702 interior to and circumferentially disposed about the inside of the cylindrical sheet, the inflation balloon 140 being overmolded in place or molded separately and assembled separately as a secondary operation, wherein the inflation balloon 140 is made before the drug delivery balloon 150;
making an inflation balloon 140 (alternatively) by overmolding the inflation balloon in place on the shaft body 120.
making a drug delivery balloon 150 by molding another cylindrical polymer sheet with ridges 602 interior to and circumferentially disposed about the inside of the another cylindrical sheet, and forming holes 608 for dispersing drug fluids from the drug delivery balloon 150 by one of the formation methods:
  making the holes 608 as part of the molding, piercing wherein the mold is configured to produce the holes 608 without added steps;
  puncturing the holes 608 using a hole-punching machine; or
  cutting or skiving away the holes 608 from the another cylindrical sheet;
  wherein any puncturing, cutting or skiving is performed with a Murphy Eye Punch (+/−0.020");
making an input array 102 by:
  coupling the input/outputs, including a drug fluid input 112, an inflation fluid input 110, and a bladder drainage output 114, allowing exposed fluid access of the drug fluid input 112, the inflation fluid input 110, and the bladder drainage output 114;
coupling the inflation balloon 140 to the shaft 120 by:
  coupling a distal end of the inflation balloon 140 to the shaft 120 at a distal inflation balloon coupling site 412, the distal inflation balloon coupling site 412 being between the drainage aperture 132 and the inflation side hole 130, the distal inflation balloon coupling site 412 being a distance from a distal end of the shaft 120 of 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1", 1.1", 1.2", 1.3", 1.4", 2", 3", 4", 5", or in a range of 0.3"-0.6", 0.3"-1", 0.3"-1.4", 0.55"-1", 0.6"-1", 0.6"-0.95", 0.6"-2", 0.6"-3", 0.6"-4", the proximal inflation balloon coupling site 414 being a distance from the drug fluid side hole 128 when the inflation balloon 140 is inflated of, 0.01", 0.011", 0.012", 0.013", 0.014", 0.015", 0.016", 0.017", 0.018", 0.019", 0.02", 0.021", 0.022", 0.023", 0.024", 0.025", 0.027", 0.03", 0.037", 0.044", 0.053", 0.06", 0.5 mm, 0.7 mm, 1 mm, 1.6 mm, 0.8 mm, 1.3 mm, 1.5 mm, or within a range of 0.005"-0.02", 0.011"-0.0147", 0.01"-0.05", 0.01"-0.06", 0.02"-0.04", 0.02"-0.05", 0.03"-0.044", 0.04"-0.053", 0.02"-0.06", 0.02"-0.053", 0.2 mm-0.4 mm, 0.1 mm-0.5 mm, 0.27 mm-0.44 mm, 0.5 mm-0.8 mm, 0.5 mm-1.5 mm, 0.5 mm-1 mm, 0.7 mm-1 mm, 0.7 mm-1.5 mm, or 0.7 mm-1.6 mm
  coupling a proximal end of the inflation balloon 140 to the shaft 120 at a proximal inflation balloon coupling site 414, the proximal inflation balloon coupling site 414 being between the inflation side hole 130 and the drug fluid side hole 128, the proximal inflation balloon coupling site 412 being a distance from a distal end of the shaft 120 of 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21", 2", 3", 4", 5", or in a range of 0.3"-0.55", 0.3"-1.21", 0.3"-5", 0.8"-1.2", 0.8"-2", 0.8"-3", 0.6"-3", or 0.8"-4";
  wherein the coupling of the inflation balloon 140 is effectuated by at least one of applying adhesive to either the inflation balloon 140 or the shaft 120 and compressing the balloon 140 against the shaft 120 at the location of the adhesive, by heat sealing the inflation balloon 140 to the shaft 120, or by placing the inflation balloon 140 on the shaft 120 and coating both the inflation balloon 140 and the shaft 120 with polymer;
coupling the drug delivery balloon 150 to the shaft 120 and optionally to the inflation balloon by:
  coupling a distal end of the drug delivery balloon 150 to the shaft 120 or the inflation balloon 140 at a distal drug delivery balloon coupling site on the distal drug delivery balloon 410b or distally on the shaft 410a, the distal inflation balloon coupling site 410 being between the drug fluid side hole 128 and the drainage aperture 132, the distal drug delivery balloon coupling site 410 being a distance from a distal end of the shaft 120 of 0.3", 0.31", 0.32", 0.33", 0.34", 0.35", 0.4", 0.41", 0.42", 0.43", 0.44", 0.45", 0.46", 0.47", 0.48", 0.49", 0.5", 0.51", 0.52", 0.53", 0.54", 0.55", 0.56", 0.57", 0.58", 0.59", 0.6", 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21", 2", 3", 4", 5" or within a range of 0.3"-0.55", 0.3"-1.21", 0.3"-5", 0.8"-1.2", 0.8"-2", 0.8"-3", 0.6"-3", or 0.8"-4"; and coupling a proximal end of the drug delivery balloon 150 to the shaft 120 or to the inflation balloon 140, at a proximal drug delivery balloon coupling site 416, the proximal drug delivery balloon coupling site 416 being between the drug side hole 128 and the proximal end of the shaft 120, the drug delivery balloon 150 covering a percentage of the inflation balloon 140 of 5%, 10%, 15%, 20%, 30%, 35%, 40%, 45%, 50%, 55%, 60%, 65%, 70%, 75%, 80%, 85%, greater than 5% but less than 95%, greater than 10% but less than 95%, greater than 15% but less than 80%, greater than 20% but less than 80%, greater than 20% but less than 70%, greater than 25% but less than 90%, less than 95%, less than 90%, less than 80%, less than 85%, less than 75%, less than 70%, less than 67%, less than 65%, less than 60%, less than 55%, less than 50%, less than 45%, less than 40%, less than 35%, less than 30%, less than 25%, or less than 20% when the inflation balloon 140 is inflated to a pressure of 2.5 atm, the rows of holes 608 of the drug balloon 150 covering a percentage of the surface area of the inflation balloon of 5%, 10%, 15%, 20%, 30%, 35%, 40%, 45%, 50%, 55%, 60%, 65%, 70%, 75%, 80%, 85%, greater than 5% but less than 95%, greater than 10% but less than 95%, greater than 15% but less than 80%, greater than 20% but less than 80%, greater than 20% but less than 70%, greater than 25% but less than 90%, less than 95%, less than 90%, less than 80%, less than 85%, less than 75%, less than 70%, less than 67%, less than 65%, less than 60%, less than 55%, less than 50%, less than 45%, less than 40%, less than 35%, less than 30%, less than 25%, or less than 20% when the inflation balloon 140 is inflated to a pressure of 2.5 atm, the proximal drug delivery balloon coupling site 416 being a distance from a distal end of the shaft 120 of 0.55", 0.56", 0.57", 0.58", 0.59", 0.6", 0.61", 0.62", 0.63", 0.64", 0.65", 0.66", 0.67", 0.68", 0.69", 0.7", 0.71", 0.72", 0.73", 0.74", 0.75", 0.76", 0.77", 0.78", 0.79", 0.8", 0.81", 0.82", 0.83", 0.84", 0.85", 0.86", 0.87", 0.88", 0.89", 0.9", 0.91", 0.92", 0.93", 0.94", 0.95", 0.96", 0.97", 0.98", 0.99", 1.1", 1.11", 1.12", 1.13", 1.14", 1.15", 1.16", 1.17", 1.18", 1.19", 1.2", 1.21" or within a range of distances 0.55"-1", 0.6"-1", 0.6"-0.95", 0.6"-2", 0.6"-3", 0.6"-4", 0.8"-1.2", 0.8"-2", 0.8"-3", 0.6"-3", 0.8"-4", or 0.55"-4", the area of the drug delivery balloons with the holes located on a proximal portion of the drug delivery balloon, the proximal portion of the balloon representing 5%, 10%, 15%, 20%, 30%, 35%, 40%, 45%, 50%, 55%, 60%, 65%, 70%, 75%, 80%, 85%, greater than 5% but less than 95%, greater than 10% but less than 95%, greater than 15% but less than 80%, greater than 20% but less than 80%, greater than 20% but less than 70%, greater than 25% but less than 90%, less than 95%, less than 90%, less than 80%, less than 85%, less than 75%, less than 70%, less than 67%, less than 65%, less than 60%, less than 55%, less than 50%, less than 45%, less than 40%, less than 35%, less than 30%, less than 25%, or less than 20% when the inflation balloon 140 is inflated to a pressure of 2.5 atm of the proximal surface area of the drug delivery balloon when inflated;

coupling the input array 102 with the shaft 120 on a proximal end of the shaft 120 by:
coupling the drug delivery lumen 122 with the drug fluid input 112 such that the drug delivery lumen 122 is in fluid communication with the drug fluid input 112;
coupling the inflation lumen 124 with the inflation fluid input 110 such that the inflation lumen 124 is in fluid communication with the inflation fluid input 110; and
coupling the bladder fluid lumen 126 with the bladder drainage output 114 such that the bladder fluid lumen 126 is in fluid communication with the bladder drainage output 114,
wherein the coupling is accomplished by heat seal, adhesive or by placing the input array 102 adjacent to the shaft 120 and coating both the input array 102 and the shaft 120 with polymer.

coupling the end cap 134 with the shaft 120 by placing the plug 802 of the end cap 134 in the bladder fluid lumen 126 at the distal end of the shaft, and optionally by coupling using an adhesive, a heat seal or by placing the end cap 134 and the shaft 120 adjacent to one another and coating both the end cap 134 and the shaft 120 with polymer.

What is claimed is:

1. A catheter, comprising:
a shaft including a distal end and a proximal end, the shaft including at least three lumens including
a drug delivery lumen in fluid communication with a drug fluid side hole in the shaft;
an inflation balloon coupled about perimeters of at least two positions on the shaft; and
a drug delivery balloon layer coupled circumferentially about a perimeter of at least one position of the inflation balloon, wherein the coupling between the drug delivery balloon layer and the inflation balloon at least partially defines a drug transfer space between an interior surface of the drug delivery balloon layer and a portion of an exterior surface of the inflation balloon, the drug transfer space in fluid communication with the drug delivery lumen via the drug fluid side hole,
wherein the drug transfer space includes a ridge extending between the interior surface of the drug delivery balloon layer and the exterior surface of the inflation balloon to maintain a minimum distance between a position of the interior surface of the drug delivery balloon layer and a position of the exterior surface of the inflation balloon.

2. The catheter of claim 1, further comprising:
an inflation space between an interior surface of the inflation balloon and the shaft, the inflation space in fluid communication with an inflation lumen of the at least three lumens via an inflation side hole,
wherein the drug transfer space and the inflation space are not in fluid communication.

3. The catheter of claim 2, further comprising:
an inflation space ridge that extends between the interior surface of the inflation balloon and the shaft.

4. The catheter of claim 1, the shaft further comprising:
a drainage aperture in communication with a bladder fluid lumen of the at least three lumens; and
an inflation side hole in communication with an inflation lumen of the at least three lumens,
wherein the drainage aperture is located distally of the inflation side hole along the shaft, the inflation side hole located distally of the drug fluid side hole.

5. The catheter of claim 4, wherein a distal position of the at least two positions is between the inflation side hole and the drainage aperture and a proximal position of the at least two positions is between the inflation side hole and the drug fluid side hole.

6. The catheter of claim 5, the drug delivery balloon layer comprising:
a proximal drug delivery balloon end coupled to one or more of the shaft and the inflation balloon proximally of the drug fluid side hole; and
a distal drug delivery balloon end, wherein the circumferential coupling about the perimeter of the at least one position of the inflation balloon is a coupling between the distal drug delivery balloon end and the inflation balloon.

7. The catheter of claim 6, further comprising:
bladder fluid channel elements, the bladder fluid channel elements including:
a bladder drainage output;
a bladder fluid lumen; and
a bladder fluid drainage aperture,
the bladder fluid channel elements all being in fluid communication;
inflation fluid elements, the inflation fluid elements including:
an inflation input;
the inflation lumen;
the inflation side hole; and
an inflation space between an interior of the inflation balloon and an exterior of the shaft,
the inflation fluid elements being in fluid communication; and
drug fluid channel elements, the drug fluid channel elements including:
a drug fluid input;
the drug delivery lumen;
the drug fluid side hole; and
the drug transfer space,
the drug fluid channel elements being in fluid communication,
wherein
the drug fluid channel elements are not in direct fluid communication with the bladder fluid channel elements and the inflation fluid elements,
the bladder fluid channel elements are not in direct fluid communication with the drug fluid channel elements and the inflation fluid elements, and
the inflation fluid elements are not in fluid communication with the drug fluid channel elements and the bladder fluid channel elements.

8. The catheter of claim 7, wherein the bladder fluid lumen has a non-uniform diameter width.

9. The catheter of claim 7, wherein the bladder fluid lumen has a narrower diameter width than a widest diameter width of the bladder fluid lumen when the narrower diameter width is collinear with a portion of one or more of the inflation lumen and the drug delivery lumen.

10. The catheter of claim 4, wherein none of the inflation lumen, drug delivery lumen, and the bladder fluid lumen contain an electronic wire.

11. The catheter of claim 1, the drug delivery balloon layer comprising:
holes to allow drug fluid in the drug transfer space to disperse from the drug transfer space.

12. The catheter of claim 11, wherein all of the holes are located proximally of an inflation side hole in the shaft that is adapted to communicate inflation fluid with the inflation balloon.

13. The catheter of claim 11, further comprising:
at least one other ridge between the interior surface of the drug delivery balloon layer and the exterior surface of the inflation balloon, wherein the holes are positioned between the ridge and the at least one other ridge.

14. A method for making a catheter, comprising:
forming at least three lumens in an interior of a shaft including a drug delivery lumen;
forming a drug fluid side hole through the shaft to the drug delivery lumen;
coupling an inflation balloon layer about perimeters of at least two axial positions on the shaft;
forming a ridge to be positioned between an exterior surface of the inflation balloon layer and an interior surface of a drug delivery balloon layer; and
coupling the drug delivery balloon layer circumferentially about a perimeter of at least one position of the inflation balloon layer coupled, wherein the coupling between the drug delivery balloon layer and the inflation balloon layer at least partially defines a drug transfer space between the interior surface of the drug delivery balloon layer and a portion of the exterior surface of the inflation balloon layer, the drug transfer space in fluid communication with the drug fluid side hole, wherein the ridge is adapted to maintain a minimum distance between a position of the interior surface of the drug delivery balloon layer and a position of the exterior surface of the inflation balloon layer.

15. The method of claim 14, further comprising:
forming an inflation side hole through the shaft to an inflation lumen of the at least three lumens, wherein the operation of forming of the drug fluid side hole forms the drug fluid side hole proximally along the shaft relative to the inflation side hole.

16. The method of claim 15, the operation of coupling an inflation balloon layer about perimeters of at least two axial positions on the shaft comprising:
coupling circumferentially a distal end of an inflation balloon to the shaft between a drainage aperture in the shaft and the inflation side hole; and
coupling circumferentially a proximal end of the inflation balloon to the shaft between the inflation side hole and the drug fluid side hole,
wherein the coupling circumferentially of the distal end of the inflation balloon to the shaft and the coupling circumferentially of the proximal end of the inflation balloon to the shaft at least partially defines an inflation space adapted to receive inflation fluid from the inflation side hole to inflate the inflation balloon layer.

17. The method of claim 16, further comprising:
coupling circumferentially a proximal end of the drug delivery balloon layer to the shaft at a position proximal to the drug fluid side hole, wherein the operation of coupling the drug delivery balloon layer includes coupling circumferentially a distal end of the drug delivery balloon layer a position on the inflation balloon distal to the proximal end of the inflation balloon.

18. The method of claim 17, wherein the coupling of the proximal end of the inflation balloon occurs before the coupling of the distal end of the drug delivery balloon layer.

19. A method of using a catheter, comprising:

introducing a distal end of a drug delivery catheter into a bladder, the catheter including a shaft including at least three lumens, the at least three lumens including a drug fluid lumen in communication with a side hole in the shaft;

inflating an inflation balloon of the drug delivery catheter by injecting inflation fluid into an inflation fluid input, causing the inflation fluid to travel through an inflation lumen of the at least three lumens within the shaft of the drug delivery catheter, through an inflation side hole to an interior of the inflation balloon; and injecting a drug fluid into the bladder by injecting a drug fluid into a drug fluid input, through a drug fluid lumen, through a drug delivery side hole, through a drug transfer space between an interior surface of a drug delivery balloon layer and an exterior surface of the inflation balloon, through holes in the drug delivery balloon layer to the bladder; and maintaining, by a ridge extending between the interior surface of the drug delivery balloon layer and the exterior surface of the inflation balloon, a minimum distance between the interior surface of the drug delivery balloon layer and the exterior surface of the inflation balloon, wherein the drug fluid and the inflation fluid are fluids of different composition and are not in fluid communication.

20. The method of claim 19, further comprising:

positioning the drug delivery catheter to expose the holes to a surface of a trigone area of the bladder, in order to deliver the drug fluid directly to the trigone area of the bladder.

* * * * *